(12) United States Patent
Nygren

(10) Patent No.: US 8,460,872 B2
(45) Date of Patent: Jun. 11, 2013

(54) QUANTIFICATION OF A MINORITY NUCLEIC ACID SPECIES

(75) Inventor: Anders Nygren, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 13/458,341

(22) Filed: Apr. 27, 2012

(65) Prior Publication Data

US 2012/0322072 A1    Dec. 20, 2012

Related U.S. Application Data

(60) Provisional application No. 61/480,686, filed on Apr. 29, 2011.

(51) Int. Cl.
*C12Q 1/68*    (2006.01)
(52) U.S. Cl.
USPC .......................................................... 435/6.1
(58) Field of Classification Search
None
See application file for complete search history.

(56) References Cited

U.S. PATENT DOCUMENTS

| | | | |
|---|---|---|---|
| 4,109,496 A | 8/1978 | Allemann et al. |
| 4,179,337 A | 12/1979 | Davis et al. |
| 4,458,066 A | 7/1984 | Caruthers et al. |
| 4,469,863 A | 9/1984 | Ts'o et al. |
| 4,522,811 A | 6/1985 | Eppstein et al. |
| 4,656,127 A | 4/1987 | Mundy |
| 4,676,980 A | 6/1987 | Segal et al. |
| 4,683,195 A | 7/1987 | Mullis et al. |
| 4,683,202 A | 7/1987 | Mullis |
| 4,851,331 A | 7/1989 | Vary et al. |
| 4,868,103 A | 9/1989 | Stavrianopoulos et al. |
| 4,873,316 A | 10/1989 | Meade et al. |
| 4,965,188 A | 10/1990 | Mullis et al. |
| 5,048,530 A | 9/1991 | Hurwitz |
| 5,075,212 A | 12/1991 | Rotbart |
| 5,118,937 A | 6/1992 | Hillenkamp et al. |
| 5,210,015 A | 5/1993 | Gelfand et al. |
| 5,272,071 A | 12/1993 | Chappel et al. |
| 5,283,317 A | 2/1994 | Saifer et al. |
| 5,487,972 A | 1/1996 | Gelfand et al. |
| 5,492,806 A | 2/1996 | Drmanac et al. |
| 5,525,464 A | 6/1996 | Drmanac et al. |
| 5,536,821 A | 7/1996 | Agrawal et al. |
| 5,541,306 A | 7/1996 | Agrawal et al. |
| 5,547,835 A | 8/1996 | Koster |
| 5,589,330 A | 12/1996 | Shuber |
| 5,605,798 A | 2/1997 | Koster |
| 5,614,622 A | 3/1997 | Iyer et al. |
| 5,631,169 A | 5/1997 | Lakowicz et al. |
| 5,637,683 A | 6/1997 | Usher et al. |
| 5,637,684 A | 6/1997 | Cook |
| 5,656,493 A | 8/1997 | Mullis et al. |
| 5,679,524 A | 10/1997 | Nikiforov et al. |
| 5,691,141 A | 11/1997 | Koster |
| 5,695,940 A | 12/1997 | Drmanac et al. |
| 5,700,922 A | 12/1997 | Cook |
| 5,717,083 A | 2/1998 | Cook et al. |
| 5,719,262 A | 2/1998 | Buchardt et al. |
| 5,720,928 A | 2/1998 | Schwartz |
| 5,739,308 A | 4/1998 | Kandimalla et al. |
| 5,739,314 A | 4/1998 | Roy et al. |
| 5,766,849 A | 6/1998 | McDonough et al. |
| 5,773,601 A | 6/1998 | Agrawal |
| 5,786,146 A | 7/1998 | Herman et al. |
| 5,834,189 A | 11/1998 | Stevens et al. |
| 5,849,483 A | 12/1998 | Shuber |
| 5,849,497 A | 12/1998 | Steinman |
| 5,849,542 A | 12/1998 | Reeve et al. |
| 5,849,546 A | 12/1998 | Sousa et al. |
| 5,851,770 A | 12/1998 | Babon et al. |
| 5,869,242 A | 2/1999 | Kamb |
| 5,876,934 A | 3/1999 | Duthie et al. |
| 5,886,165 A | 3/1999 | Kandimalla et al. |
| 5,891,625 A | 4/1999 | Buchardt et al. |
| 5,908,755 A | 6/1999 | Kumar et al. |
| 5,912,118 A | 6/1999 | Ansorge et al. |
| 5,928,906 A | 7/1999 | Koster et al. |
| 5,929,226 A | 7/1999 | Padmapriya et al. |
| 5,952,174 A | 9/1999 | Nikiforov et al. |
| 5,955,599 A | 9/1999 | Iyer et al. |
| 5,958,692 A | 9/1999 | Cotton et al. |
| 5,962,674 A | 10/1999 | Iyer et al. |
| 5,976,802 A | 11/1999 | Ansorge et al. |
| 5,977,296 A | 11/1999 | Nielsen et al. |
| 5,981,186 A | 11/1999 | Gabe et al. |
| 5,998,143 A | 12/1999 | Ellis et al. |
| 6,004,744 A | 12/1999 | Goelet et al. |

(Continued)

FOREIGN PATENT DOCUMENTS

| | | |
|---|---|---|
| EP | 264166 | 4/1988 |
| EP | 0401384 | 12/1990 |

(Continued)

OTHER PUBLICATIONS

Ding et al. (Proc Natl Acad Sci U S A. Mar. 18, 2003;100(6):3059-64. Epub Mar. 6, 2003).*
Anders et al. (Clin Chem. Oct. 2010;56(10):1627-35. Epub Aug. 20, 2010).*
Adinolfi et al., "Rapid detection of aneuploidies by microsatellite and the quantitative fluorescent polymerase chain reaction." Prenat Diagn. Dec. 1997;17(13):1299-311.
Agresti, Categorical Data Analysis, 2nd Ed. 2002. Wiley.
Altschul et al., "Basic local alignment search tool." J Mol Biol. Oct. 5, 1990;215(3):403-10.
Altschul et al., "Gapped BLAST and PSI-BLAST: a new generation of protein database search programs." Nucleic Acids Res. Sep. 1, 1997;25(17):3389-402.
Amicucci et al., Clin. Chem. 46:301-302, 2000.
Amir et al., Nature Genet. 23:185-88 (1999).
Anantha et al., "Porphyrin binding to quadrupled T4G4." Biochemistry. Mar. 3, 1998;37(9):2709-14.

(Continued)

*Primary Examiner* — Christopher M. Babic
(74) *Attorney, Agent, or Firm* — Grant Anderson LLP

(57) ABSTRACT

The technology relates in part to quantification of a minority nucleic acid species from a nucleic acid sample. In some embodiments, methods for determining the amount of fetal nucleic acid (e.g. absolute amount, relative amount) in a maternal sample are provided.

23 Claims, 17 Drawing Sheets

U.S. PATENT DOCUMENTS

| | | | |
|---|---|---|---|
| 6,013,431 A | 1/2000 | Soderlund et al. |
| 6,013,499 A | 1/2000 | Narumiya et al. |
| 6,017,702 A | 1/2000 | Lee et al. |
| 6,018,041 A | 1/2000 | Drmanac et al. |
| 6,024,925 A | 2/2000 | Little et al. |
| 6,043,031 A | 3/2000 | Koster et al. |
| 6,045,996 A | 4/2000 | Cronin et al. |
| 6,046,005 A | 4/2000 | Ju et al. |
| 6,087,095 A | 7/2000 | Rosenthal et al. |
| 6,107,037 A | 8/2000 | Sousa et al. |
| 6,110,684 A | 8/2000 | Kemper et al. |
| 6,117,992 A | 9/2000 | Iyer |
| 6,136,541 A | 10/2000 | Gulati |
| 6,140,053 A | 10/2000 | Koster |
| 6,140,054 A | 10/2000 | Wittwer et al. |
| 6,140,482 A | 10/2000 | Iyer et al. |
| 6,142,681 A | 11/2000 | Gulati |
| 6,143,496 A | 11/2000 | Brown et al. |
| 6,156,501 A | 12/2000 | McGall et al. |
| 6,183,958 B1 | 2/2001 | Stanton, Jr. |
| 6,194,144 B1 | 2/2001 | Koster |
| 6,194,180 B1 | 2/2001 | Joyce |
| 6,197,506 B1 | 3/2001 | Fodor et al. |
| 6,210,574 B1 | 4/2001 | Sammons et al. |
| 6,210,891 B1 | 4/2001 | Nyren et al. |
| 6,214,556 B1 | 4/2001 | Olek et al. |
| 6,214,560 B1 | 4/2001 | Yguerabide et al. |
| 6,223,127 B1 | 4/2001 | Berno |
| 6,225,625 B1 | 5/2001 | Pirrung et al. |
| 6,229,911 B1 | 5/2001 | Balaban et al. |
| 6,239,273 B1 | 5/2001 | Pease et al. |
| 6,251,638 B1 | 6/2001 | Umansky et al. |
| 6,258,538 B1 | 7/2001 | Koster et al. |
| 6,258,540 B1 | 7/2001 | Lo et al. |
| 6,297,028 B1 | 10/2001 | Taniguchi et al. |
| 6,326,174 B1 | 12/2001 | Joyce et al. |
| 6,368,834 B1 | 4/2002 | Senapathy et al. |
| 6,440,706 B1 | 8/2002 | Vogelstein et al. |
| 6,664,056 B2 | 12/2003 | Lo et al. |
| 6,723,513 B2 | 4/2004 | Lexow |
| 6,759,217 B2 | 7/2004 | Kopreski |
| 6,818,394 B1 | 11/2004 | O'Donnell-Maloney et al. |
| 6,884,586 B2 | 4/2005 | Van Ness et al. |
| 6,916,634 B2 | 7/2005 | Kopreski |
| 6,927,028 B2 | 8/2005 | Dennis et al. |
| 6,929,911 B2 | 8/2005 | Oefner et al. |
| 7,081,339 B2 | 7/2006 | Slepnev |
| 7,169,314 B2 | 1/2007 | Unger et al. |
| 7,244,567 B2 | 7/2007 | Chen et al. |
| 7,253,259 B2 | 8/2007 | Otagiri et al. |
| 7,285,422 B1 | 10/2007 | Little et al. |
| 7,468,249 B2 | 12/2008 | Xie et al. |
| 7,655,399 B2 * | 2/2010 | Cantor et al. ............ 435/6.12 |
| 7,709,262 B2 | 5/2010 | Cantor et al. |
| 7,785,798 B2 * | 8/2010 | Cantor et al. ............ 435/6.12 |
| 2001/0008615 A1 | 7/2001 | Little et al. |
| 2001/0051341 A1 | 12/2001 | Lo et al. |
| 2002/0006621 A1 | 1/2002 | Bianchi |
| 2003/0022207 A1 | 1/2003 | Balasubramanian et al. |
| 2003/0082600 A1 | 5/2003 | Olek et al. |
| 2003/0087276 A1 | 5/2003 | Kopreski |
| 2003/0096426 A1 | 5/2003 | Little et al. |
| 2003/0180748 A1 | 9/2003 | Braun et al. |
| 2003/0180779 A1 | 9/2003 | Lofton-Day et al. |
| 2003/0211483 A1 | 11/2003 | Schroeder et al. |
| 2003/0211522 A1 | 11/2003 | Landes et al. |
| 2004/0014105 A1 | 1/2004 | Schroeder et al. |
| 2004/0081993 A1 | 4/2004 | Cantor et al. |
| 2004/0115684 A1 | 6/2004 | Costa |
| 2004/0137470 A1 | 7/2004 | Dhallan |
| 2004/0203037 A1 | 10/2004 | Lo et al. |
| 2005/0009059 A1 | 1/2005 | Shapero et al. |
| 2005/0019762 A1 | 1/2005 | Olek |
| 2005/0037388 A1 | 2/2005 | Antonarakis et al. |
| 2005/0059003 A1 | 3/2005 | Enoki et al. |
| 2005/0064406 A1 | 3/2005 | Zabarovsky et al. |
| 2005/0064428 A1 | 3/2005 | Berlin |
| 2005/0069879 A1 | 3/2005 | Berlin |
| 2005/0079521 A1 | 4/2005 | Beaulieu et al. |
| 2005/0112590 A1 | 5/2005 | Boom et al. |
| 2005/0153316 A1 | 7/2005 | Jeddeloh et al. |
| 2005/0153347 A1 | 7/2005 | Shapero et al. |
| 2005/0164241 A1 | 7/2005 | Hahn et al. |
| 2005/0272070 A1 | 12/2005 | Ehrich et al. |
| 2005/0287592 A1 | 12/2005 | Kless |
| 2006/0019278 A1 | 1/2006 | Lo et al. |
| 2006/0094039 A1 | 5/2006 | Rosenfeld et al. |
| 2006/0160105 A1 | 7/2006 | Dhallan |
| 2006/0166228 A1 | 7/2006 | Page et al. |
| 2006/0210992 A1 | 9/2006 | van den Boom |
| 2006/0252068 A1 | 11/2006 | Lo et al. |
| 2006/0252071 A1 | 11/2006 | Lo et al. |
| 2007/0048755 A1 | 3/2007 | Di Fiore |
| 2007/0059707 A1 * | 3/2007 | Cantor et al. ............ 435/6 |
| 2007/0065823 A1 | 3/2007 | Dressman et al. |
| 2007/0111233 A1 | 5/2007 | Bianchi et al. |
| 2007/0202525 A1 | 8/2007 | Quake et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0275402 A1 | 11/2007 | Lo et al. |
| 2008/0070792 A1 | 3/2008 | Stoughton et al. |
| 2008/0096766 A1 | 4/2008 | Lee |
| 2008/0299562 A1 | 12/2008 | Oeth |
| 2008/0305479 A1 | 12/2008 | Van Den Boom |
| 2009/0026082 A1 | 1/2009 | Rothberg et al. |
| 2009/0029377 A1 | 1/2009 | Lo et al. |
| 2009/0061425 A1 | 3/2009 | Lo et al. |
| 2009/0111712 A1 | 4/2009 | VanDenBoom et al. |
| 2009/0142755 A1 | 6/2009 | Albitar |
| 2009/0202984 A1 | 8/2009 | Cantor |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0184046 A1 | 7/2010 | Klass et al. |
| 2010/0203529 A1 | 8/2010 | Kuslich et al. |
| 2010/0227320 A1 | 9/2010 | Fu |
| 2010/0240054 A1 | 9/2010 | Bischoff |
| 2010/0273165 A1 | 10/2010 | Ehrich et al. |
| 2010/0279295 A1 | 11/2010 | Roy et al. |
| 2011/0033851 A1 | 2/2011 | Rand |
| 2011/0151460 A1 | 6/2011 | Klass et al. |
| 2011/0177517 A1 | 7/2011 | Rava et al. |
| 2011/0178719 A1 | 7/2011 | Rabinowitz et al. |
| 2011/0201507 A1 | 8/2011 | Rava et al. |
| 2011/0212846 A1 | 9/2011 | Spier |
| 2011/0224087 A1 | 9/2011 | Quake et al. |
| 2011/0276277 A1 | 11/2011 | Lo et al. |
| 2011/0288780 A1 | 11/2011 | Rabinowitz et al. |
| 2012/0264618 A1 | 10/2012 | Nygren |
| 2012/0276542 A1 | 11/2012 | Nygren |

FOREIGN PATENT DOCUMENTS

| | | |
|---|---|---|
| EP | 1524321 | 4/2009 |
| WO | WO 91/06667 | 5/1991 |
| WO | WO 94/10300 | 5/1994 |
| WO | WO 97/35589 | 10/1997 |
| WO | WO 97/37041 | 10/1997 |
| WO | WO 98/20020 | 5/1998 |
| WO | WO 98/22489 | 5/1998 |
| WO | WO 98/39352 | 9/1998 |
| WO | WO 98/39474 | 9/1998 |
| WO | WO 98/54364 | 12/1998 |
| WO | WO 99/57318 | 5/1999 |
| WO | WO 00/52625 | 9/2000 |
| WO | WO 00/56746 | 9/2000 |
| WO | WO 00/66771 | 11/2000 |
| WO | WO 00/75372 | 12/2000 |
| WO | WO 01/14398 | 3/2001 |
| WO | WO 01/20039 | 3/2001 |
| WO | WO 01/25485 | 4/2001 |
| WO | WO 01/27326 | 4/2001 |
| WO | WO 01/27327 | 4/2001 |
| WO | WO 01/27329 | 4/2001 |
| WO | WO 01/29259 | 4/2001 |
| WO | WO 02/18616 | 3/2002 |
| WO | WO 02/086163 | 10/2002 |

| | | |
|---|---|---|
| WO | WO 03/000919 | 1/2003 |
| WO | WO 03/057909 | 7/2003 |
| WO | WO 03/062441 | 7/2003 |
| WO | WO 03/080863 | 10/2003 |
| WO | WO 2004/013284 | 2/2004 |
| WO | WO 2004/076653 | 9/2004 |
| WO | WO 2005/012578 | 2/2005 |
| WO | WO 2005/021793 | 3/2005 |
| WO | WO 2005/023091 | 3/2005 |
| WO | WO 2005/035725 | 4/2005 |
| WO | WO 2005035725 A2 * | 4/2005 |
| WO | WO 2005/040399 | 5/2005 |
| WO | WO 2005/098050 | 10/2005 |
| WO | WO 2006/056480 | 6/2006 |
| WO | WO 2006/097051 | 9/2006 |
| WO | WO 2007/016668 | 2/2007 |
| WO | WO 2007/028155 | 3/2007 |
| WO | WO 2007/132166 | 11/2007 |
| WO | WO 2007/140417 | 12/2007 |
| WO | WO 2007/147063 | 12/2007 |
| WO | WO 2008/098142 | 8/2008 |
| WO | WO 2008/103761 | 8/2008 |
| WO | WO 2008/103763 | 8/2008 |
| WO | WO 2008/118988 | 10/2008 |
| WO | WO 2008/157264 | 12/2008 |
| WO | WO 2009/032779 | 3/2009 |
| WO | WO 2009/032781 | 3/2009 |
| WO | WO 2009/046445 | 4/2009 |
| WO | WO 2009/091934 | 7/2009 |
| WO | WO 2009/114543 | 9/2009 |
| WO | WO 2010/004265 | 1/2010 |
| WO | WO 2010/033639 | 3/2010 |
| WO | WO 2010/115016 | 10/2010 |
| WO | WO 2011/034631 | 3/2011 |
| WO | WO 2011/087760 | 7/2011 |
| WO | WO 2011/092592 | 8/2011 |
| WO | WO 2011/142836 | 11/2011 |
| WO | WO 2011/143659 | 11/2011 |
| WO | WO 2012/149339 | 11/2012 |

OTHER PUBLICATIONS

Anders et al., Clin Chem, Oct. 2010, 56(10):1627-1635, Epub Aug. 20, 2010.
Anderson, S., "Shotgun DNA sequencing using cloned Dnase I-generated fragments," Nucl. Acids Res. 9:3015-3027 (1981).
Antonarakis et al., Am J Hum Genet. Mar. 1992;50(3):544-50.
Antonarakis et al., Nat Genet. Feb. 1993;3(2):146-50.
Aoki E. et al., "Methylation status of the p15INK4B gene in hematopoietic progenitors and peripheral blood cells in myelodysplastic syndromes", Leukemia 14(4):586-593 (2000).
Armour et al., "Measurement of locus copy number by hybridisation with amplifiable probes." Nucleic Acids Res. Jan. 15, 2000;28(2):605-9.
Armour et al., "The detection of large deletions or duplications in genomic DNA." Hum Mutat. Nov. 2002;20(5):325-37.
Asimakopoulos FA et al., "ABL 1 methylation is a distinct molecular event associated with clonal evolution of chronic myeloid leukemia" Blood 94(7):2452-2460 (1999).
Aston et al. (1999) Methods Enzymol. 303:55-73.
Aston et al. (1999) Trends Biotechnol. 17(7):297-302.
Ausubel et al., Current Protocols in Molecular Biology (Ausubel et al., eds., 1994).
Banerji et al., "A lymphocyte-specific cellular enhancer is located downstream of the joining region in immunoglobulin heavy chain genes." Cell. Jul. 1983;33(3):729-40.
Bartel et al., Biotechniques 14: 920-924 (1993).
Batey et al. (1992) Nucl. Acids Res. 20, 4515-4523.
Batey et al. (1996) Nucl. Acids Res. 24, 4836-4837.
Batzer et al., Nucleic Acid Res. 19:5081 (1991).
Beaucage & Caruthers, Tetrahedron Lett. 22: 1859-1862 (1981).
Beckman Coulter, Introduction to Capillary Electrophoresis, Beckman Coulter 1991.
Benson G. Tandem repeats finder: a program to analyze DNA sequences. Nucleic Acids Res. Jan. 15, 1999;27(2):573-80.
Bianchi, 'Fetal cells in the mother: from genetic diagnosis to diseases associated with fetal cell microchimerism', In: European Journal of Obstetrics & Gynecology and Reproductive Biology, Sep. 2000, vol. 92(I), pp. 103-108.
Boguski et al., "Identification of a cytidine-specific ribonuclease from chicken liver." J Biol Chem. Mar. 10, 1980;255(5):2160-3.
Boom et al. (1990, J. Clin. Microbiol. 28: 495-503.
Boom et al. (1991, J. Clin. Microbiol. 29: 1804-1811.
Boyer, L.A. et al. Polycomb complexes repress developmental regulators in murine embryonic stem cells. Nature 441, 349-53 (2006).
Braslavsky et al., "Sequence information can be obtained from single DNA molecules." Proc Natl Acad Sci U S A. Apr. 1, 2003;100(7):3960-4. Epub Mar. 21, 2003.
Brizot et al., "Maternal serum hCG and fetal nuchal translucency thickness for the prediction of fetal trisomies in the first trimester of pregnancy." Br J Obstet Gynaecol. Feb. 1995;102(2):127-32.
Bullinger et al., "Use of gene-expression profiling to identify prognostic subclasses in adult acute myeloid leukemia." N Engl J Med. Apr. 15, 2004;350(16):1605-16.
Burlingame et al. Anal. Chem. 70:647R-716R (1998).
Burnier et al., "Cell-derived microparticles in haemostasis and vascular medicine," Thromb Haemost 2009, 101:439-451.
Byrne et al., "Multiplex gene regulation: a two-tiered approach to transgene regulation in transgenic mice." Proc Natl Acad Sci U S A. Jul. 1989;86(14):5473-7.
Calame et al., "Transcriptional controlling elements in the immunoglobulin and T cell receptor loci." Adv Immunol. 1988;43:235-75.
Caliper LifeSciences, Products and Contract Services, LabChip GX 2010, printed from the internet on Mar. 15, 2011 (http://www.caliperl.com/products/labchip-gx.htm).
Camper et al., "Postnatal repression of the alpha-fetoprotein gene is enhancer independent." Genes Dev. Apr. 1989;3(4):537-46.
Chan et al. (2004) Clin. Chem. 50:88-92.
Chan et al., Oncogene 22:924-934 (2003).
Chang et al., "LIBSVM: a library for Support Vector Machines," 2001.
Chen et al., "Fluorescence energy transfer detection as a homogeneous DNA diagnostic method." Proc Natl Acad Sci U S A. Sep. 30, 1997;94(20):10756-61.
Chen et al., "Template-directed dye-terminator incorporation (TDI) assay: a homogeneous DNA diagnostic method based on fluorescence resonance energy transfer." Nucleic Acids Res. Jan. 15, 1997;25(2):347-53.
Cheson et al, "Report of the National Cancer Institute-sponsored workshop on definitions of diagnosis and response in acute myeloid leukemia" J Clin Oncol 8:813-819, 1990.
Cheung et al. (1994, J. Clin. Microbiol. 32: 2593-2597).
Chirgwin et al. (1979, Biochem. 18: 5294-5299.
Chitty, L. Br Med Bull 54:839-856 (1998).
Chiu et al., "Effects of blood-processing protocols on fetal and total DNA quantification in maternal plasma." Clin Chem. Sep. 2001;47(9):1607-1613.
Chiu et al., Lancet 360:998-1000, 2002.
Chomczynski and Mackey (1995, Anal. Biochem. 225: 163-164).
Chomczynski and Mackey (1995, Biotechniques 19: 942-945).
Chomczynski and Sacchi (1987, Analytical Biochem. 162: 156-159).
Chomczynski, (1993, Biotech. 15: 532-537).
Chow, K.C., et al., Mass Spectrometric detection of a SNP panel as an internal positive control for fetal DNA analysis in maternal plasma. Clin. Chem. 53, 141-142 (2007).
Chu et al, "A novel approach toward the challenge of accurately quantifying fetal DNA in maternal plasma," Prenatal Diagnosis, 2010; 30:1226-1229.
Colella et al. Biotechniques. Jul. 2003;35(1):146-50.
Costa et al., N. Engl. J. Med. 346:1502, 2002).
Costello et al., Restriction Landmark Genomic Scanning (RLGS): Analysis of CpG Islands in genomes by 2D Gel Electrophoresis, Methods in Molecular Biology, DNA Methylation, 2 Methods and Protocols, v.: 507, 2nd eds., pp. 131-148 (2000).
Cruikshank et al., "A lipidated anti-Tat antibody enters living cells and blocks HIV-1 viral replication." J. Acquired Immune Deficiency Syndromes and Human Retrovirology Mar. 1, 1997;14(3):193-203.
Current Protocols in Molecular Biology, John Wiley & Sons, N.Y., 6.3.1-6.3.6 (1989).
D'Alton., "Prenatal diagnostic procedures." Semin Perinatol. Jun. 1994;18(3):140-62.

Das, R. et al. Proc Natl Acad Sci U S A 103, 10713-6 (2006).
Davison., "Sedimentation of deoxyribonucleic acid isolated under low hydrodynamic shear." Nature. Mar. 26, 1960;185:918-20.
Davison., "The Effect of Hydrodynamic Shear on the Deoxyribonucleic Acid From T(2) and T(4) Bacteriophages." Proc Natl Acad Sci U S A. Nov. 1959;45(11):1560-8.
Dayie et al. (1998) J. Mag. Reson. 130, 97-101 (1998).
Dear, "One by one: Single molecule tools for genomics." Brief Funct Genomic Proteomic. Jan. 2003;1(4):397-416.
Deininger, P. L. "Random subcloning of sonicated DNA: application to shotgun DNA sequence analysis," Anal. Biochem. 129(1):216-223 (1983).
Dembo et al., 1994, Ann. Prob. 22: 2022-2039.
Ding C, Cantor CR (2003) A high-throughput gene expression analysis technique using competitive PCR and matrix-assisted laser desorption ionization time-of-flight MS. Proc Natl Acad Sci U S A 100:3059-3064.
Donis-Keller et al., Nucl. Acids Res. 4:2527-2537 (1977).
Donis-Keller., "Phy M: an RNase activity specific for U and A residues useful in RNA sequence analysis." Nucleic Acids Res. Jul. 25, 1980;8(14):3133-42.
Dupont JM, Tost J, Jammes H, and Gut IG. Anal Biochem, Oct. 2004; 333(1): 119-27.
Eads et al., Cancer Res. 59:2302-2306, 1999.
Eckhardt, F. et al. Nat Genet 38, 1378-85 (2006.
Edlund et al., "Cell-specific expression of the rat insulin gene: evidence for role of two distinct 5' flanking elements." Science. Nov. 22, 1985;230(4728):912-6.
Egger et al., "Reverse transcription multiplex PCR for differentiation between polio- and enteroviruses from clinical and environmental samples." J Clin Microbiol. Jun. 1995;33(6):1442-7.
Ehrich et al., "Noninvasive detection of fetal trisomy 21 by sequencing of DNA in maternal blood: a study in a clinical setting," Reports of Major Impact, American Journal of Obstetrics and Gyenocology, Mar. 2011, 205e1-205e11.
Ehrich et al., A new method for accurate assessment of DNA quality after bisulfite treatment, Nucl. Acids Res. (2007) 35(5): e29 1-8.
Ehrich M, et al. (2005) Quantitative high-throughput analysis of DNA methylation patterns by base specific cleavage and mass spectrometry. Proc Natl Acad Sci U S A 102:15785-15790.
Ehrich M, et al. (2008) Cytosine methylation profiling of cancer cell lines. Proc Natl Acad Sci U S A 105:4844-48.
Eiben et al., "First-trimester screening: an overview." J Histochem Cytochem. Mar. 2005;53(3):281-3.
Ernani et al., Agilent's SureSelect Target Enrichment System: Bringing Cost and Process Efficiency to Next-Generation Sequencing Product Note, Agilent Technologies, Mar. 16, 2009.
Eva and Aaronson, Nature, 316:273-275, 1985.
Fajkusova L. et al., "Detailed Mapping of Methylcytosine Positions at the CpG Island Surrounding the Pa Promoter at the bcr-abl Locus in CML Patients and in Two Cell Lines, K562 and BV173" Blood Cells Mol. Dis. 26(3):193-204 (2000).
Fan et al., "Noninvasive diagnosis of fetal aneuploidy by shotgun sequencing DNA from maternal blood." Proc Natl Acad Sci U S A. Oct. 21, 2008;105(42):16266-71. Epub Oct. 6, 2008.
Fan et al., "Working Set Selection Using the Second Order Information for Training SVM" Journal of Machine Learning Research 6 (2005) 1889-1918.
Feinberg., "Methylation meets genomics." Nat Genet. Jan. 2001;27(1):9-10.
Ferguson-Smith, "Placental mRNA in maternal plasma: Prospects for fetal screening", PNAS vol. 100, No. 8, 4360-4362 Apr. 15, 2003.
Fournie et al. (1986 Anal. Biochem. 158: 250-256).
Frommer et al. (Proc. Natl. Acad. Sci. USA 89:1827-1831, 1992.
Futreal, P.A. et al. Nat Rev Cancer 4, 177-83 (2004).
Gardiner-Garden et al., "CpG islands in vertebrate genomes." J Mol Biol. Jul. 20, 1987;196(2):261-82.
Gebhard C, Schwarzfischer L, Pham TH, Andreesen R, Mackensen A, Rehli M (2006) Rapid and sensitive detection of CpG-methylation using methyl-binding (MB)-PCR. Nucleic Acids Res 34:e82.
Gebhard C, Schwarzfischer L, Pham TH, Schilling E, Klug M, Andreesen R, Rehli M (2006) Genomewide profiling of CpG methylation identifies novel targets of aberrant hypermethylation in myeloid leukemia. Cancer Res 66:6118-6128).
Giles et al., "Acute myeloid leukemia." Hematology Am Soc Hematol Educ Program. 2002:73-110.
Go et al. Clin Chem. Dec. 2007;53(12):2223-4.
Goeddel, Gene Expression Technology: Methods in Enzymology 185, Academic Press, San Diego, CA (1990).
Gonzalgo & Jones, Nucleic Acids Res. 25:2529-2531, 1997.
Gottesman, S., Gene Expression Technology: Methods in Enzymology, Academic Press, San Diego, California 185: 119-129 (1990).
Grompe et al., Proc. Natl. Acad. Sci. USA 86: 5855-5892 (1989.
Grompe., "The rapid detection of unknown mutations in nucleic acids." Nat Genet. Oct. 1993;5(2):111-7.
Grunau et al., "Bisulfite genomic sequencing: systematic investigation of critical experimental parameters." Nucleic Acids Res. Jul. 1, 2001;29(13):E65-5.
Gupta et al., "Use of specific endonuclease cleavage in RNA sequencing." Nucleic Acids Res. Jun. 1977;4(6):1957-78.
Haase et al., Methods in Virology, pp. 189-226, 1984.
Haddow, et al., "Screening of maternal serum for fetal Down's syndrome in the first trimester", In: The New England Journal of Medicine, Apr. 2, 1998, Vol.338(14), pp. 955-961.
Hage & Tweed, J. Chromatogr. B Biomed. Sci. Appl. Oct. 10; 699 (1-2): 499-525 (1997.
Hahn et al., (2011) Placenta 32 Suppl: S17-S20.
Hahner et al., "Matrix-assisted laser desorption/ionization mass spectrometry (MALDI) of endonuclease digests of RNA." Nucleic Acids Res. May 15, 1997;25(10):1957-64.
Hames and Higgins eds., Nucleic Acid Hybridization: A Practical Approach, IRL Press, 1985.
Hannish, J. and M. McClelland, "Activity of DNA modification and restriction enzymes in KGB, a potassium glutamate buffer," Gene Anal. Tech 5:105-107 (1988).
Harris et al., "Single-molecule DNA sequencing of a viral genome." Science. Apr. 4, 2008;320(5872)106-9.
Hart et al., J.Biol.Chem., 269:62-65, 1994.
Hasan et al., Nucl. Acids Res. 24:2150-2157 (1996.
Heegaard, J Mol. Recognit. Winter; 11(1-6): 141-8 (1998).
Hennig et al (2007) J. Am. Chem. Soc. 129, 14911-14921.
Herman et al. Proc. Nat. Acad. Sci. USA 93:9821-9826, 1996.
Hershey, A. D. and Burgi, E. J. Mol. Biol, 2:143-152 (1960.
Hill, Craig, "Gen-Probe Transcription-Mediated Amplification: System Principles," Jan. 1996 httl://www.gen-probe.com/pdfs/tma__whiteppr.pdf.
HiSeq 2000 Sequencing System Specification Sheet, Illumina Inc. 2010.
Homer, J. et al., Prenat Diagn 23:566-571 (2003).
Hook, E. B. Lancet 2:169-172 (1981).
Hromandnikova, et al., "Quantification of Fetal and Total Circulatory DNA in Maternal Plasma Samples Before and After Size Fractionation by Agarose Gel Electrophoresis,"DNA and Cell Biology, vol. 25, No. 11, 2006, pp. 635-640.
Hu, D. G. et al., "Aneuploidy detection in single cells using DNA array-based comparative genomic hybridization", Mol Hum Reprod 10: 283-289, (2004).
Huang et al., "Mechanism of ribose 2'-group discrimination by an RNA polymerase." Biochemistry. Jul. 8, 1997;36(27):8231-42.
Hulten et al., "Rapid and simple prenatal diagnosis of common chromosome disorders: advantages and disadvantages of the molecular methods FISH and QF-PCR." Reproduction. Sep. 2003;126(3):279-97.
Hunkapiller et al., "A microchemical facility for the analysis and synthesis of genes and proteins." Nature. Jul. 12-18, 1984;310(5973)105-11.
Hyrup et al., "Peptide nucleic acids (PNA): synthesis, properties and potential applications." Bioorg Med Chem. Jan. 1996;4(1):5-23.
Imai et al. , 1992, J. Virol. Methods 36: 181-184).
Imamura et al., "Prenatal diagnosis of adrenoleukodystrophy by means of mutation analysis." Prenat Diagn. Mar. 1996;16(3):259-61.
Innis et al., PCR Protocols: A Guide to Methods and Applications, Innis et al., eds, 1990.
Issa., "CpG island methylator phenotype in cancer." Nat Rev Cancer. Dec. 2004;4(12):988-93.

Iverson et al., 1981, Prenat. Diagn. 9: 31-48.
Iwabuchi et al., Oncogene 8: 1693-1696 (1993.
Jing et al. (1998) Proc Natl Acad Sci USA. 95(14):8046-51.
Johansen et al., "An investigation of methods for enriching trophoblast from maternal blood." Prenat Diagn. Oct. 1995;15(10):921-31.
Jurinke, C., et al., "MALDI-TOF mass spectrometry: a versatile tool for high-performance DNA analysis." Mol. Biotechnol. 26, 147-164 (2004.
Kalinina et al., "Nanoliter scale PCR with TaqMan detection." Nucleic Acids Res. May 15, 1997;25(10):1999-2004.
Kaneko et al., Gut 52:641-646 (2003).
Karlin et al., "Methods for assessing the statistical significance of molecular sequence features by using general scoring schemes." Proc Natl Acad Sci U S A. Mar. 1990;87(6):2264-8.
Kent, "BLAT—the BLAST-like alignment tool." Genome Res. Apr. 2002;12(4):656-64.
Kessel et al., "Murine developmental control genes." Science. Jul. 27, 1990;249(4967):374-9.
Kidd JM et al. Mapping and sequencing of structural variation from eight human genomes. Nature. May 1, 2008;453 (7191):56-64).
Kriegler, Gene Transfer and Expression: A Laboratory Manual (1990).
Kristensen et al., "PCR-Based Methods for Detecting Single-Locus DNA Methylation Biomarkers in Cancer Diagnostics, Prognostics, and Response to Treatement", Clinical Chemistry, Washington DC, vol. 55, No. 8., Aug. 1, 2009, pp. 1471-1483.
Kuchino et al., "Enzymatic RNA sequencing." Methods Enzymol. 1989;180:154-63.
Kuhn et al., "DNA Helicases" Cold Spring Harb Symp Quant Biol. 1979;43 Pt 1:63-7.
Kulkarmi et al., "Global DNA methylation patterns in placenta and its association with maternal hypertension in pre-eclampsia," (2011) DNA Cell Biol. 30(2):79-84.
Kumps et al., "RMeseuarlcthi aprtilcelex Amplicon Quantification (MAQ), a fast and efficient method for the simultaneous detection of copy number alterations in neuroblastoma," BMC Genomics 2010, 11:298, pp. 1-10.
Lai et al. (1999) Nat Genet. 23(3):309-13.
Laird, P.W. Nature Reviews Cancer 3, 253-266 (2003).
Larkin et al., "Clustal W and Clustal X version 2.0." Bioinformatics. Nov. 1, 2007;23(21):2947-8. Epub Sep. 10, 2007.
Lee et al., Fetal Nucleic Acids in Maternal Plasma, In: Fetal and Maternal Medicine Review, 2006, vol. 17,(2), pp. 125-137.
Lee Ti, et al. (2006) Control of developmental regulators by Polycomb in human embryonic stem cells. Cell 125:301-313).
Leung et al., "An efficient algorithm for identifying matches with errors in multiple long molecular sequences." J Mol Biol. Oct. 20, 1991;221(4):1367-78.
Li et al. Nucl. Acids Res. 23:4495-4501 (1995).
Li et al., "Size separation of circulatory DNA in maternal plasma permits ready detection of fetal DNA polymorphisms." Clin Chem. Jun. 2004;50(6):1002-11. Epub Apr. 8, 2004.
Li et al., "Targeted mutation of the DNA methyltransferase gene results in embryonic lethality." Cell. Jun. 12, 1992;69(6):915-26.
Li, Y., et al., Genotyping fetal paternally inherited SNPs by MALDI-TOF MS using cell-free fetal DNA in maternal plasma: Influence of size fractionation. Electrophoresis 27, 3889-3896 (2006).
Lingbeek, M.E., Bruggeman, S.W. & van Lohuizen, M. Cell 118, 409-18 (2004).
Little, et al. Nat Med 3:1413-6 (1997.
Litz C. E. et al., "Methylation status of the major breakpoint cluster region in Philadelphia chromosome negative leukemias" Leukemia 6(1):35-41 (1992.
Liu et al., "Quantification of regional DNA methylation by liquid chromatography/tandem mass spectrometry", Analytical Biochemistry, Academic Press Inc, New York, vol. 391, No. 2, Aug. 15, 2009, pp. 106-113.
Liu et al., "The ribosomal small-subunit protein S28 gene from *Helianthus annuus* (asteraceae) is down-regulated in response to drought, high salinity, and abscisic acid," American Journal of Botany, vol. 90, No. 4., Apr. 1, 2003, pp. 526-531.
Lo et al. (Nat Med. Feb. 2007;13(2):218-23).
Lo et al., "Maternal Plasma DNA Sequencing Reveals the Genome-Wide Genetic and Mutational Profile of the Fetus," Prenatal Diagnosis, Science Translational Medicine, Dec. 8, 2010, vol. 2, Issue 61, 1-13 Lo et al. (2010).
Lo et al., "Presence of fetal DNA in maternal plasma and serum." Lancet. Aug. 16, 1997;350(9076):485-7.
Lo et al., "Quantitative analysis of fetal DNA in maternal plasma and serum: implications for noninvasive prenatal diagnosis." Am J Hum Genet. Apr. 1998;62(4):768-75.
Lo et al., Clin. Chem. 45:1747-1751, 1999.
Lo et al., Clin. Chem. 45:184-188, 1999.
Lo et al., N. Engl. J. Med. 339:1734-1738, 1998).
Lo, "Recent advances in fetal nucleic acids in maternal plasma." J Histochem Cytochem. Mar. 2005;53(3):293-6.
Lun et al., "Microfluidics digital PCR reveals a higher than expected fraction of fetal DNA in maternal plasma." Clin Chem. Oct. 2008;54(10):1664-72. Epub Aug. 14, 2008.
Lun et al., "Noninvasive prenatal diagnosis of monogenic diseases by digital size selection and relative mutation dosage on DNA in maternal plasma," PNAS, vol. 105, No. 50, Dec. 16, 2008, pp. 19920-19925.
Madura et al., J. Biol. Chem. 268: 12046-12054 (1993).
Majlessi et al., Nucleic Acids Research, 26(9):2224-2229, (1998).
Malik et al., "Polyethylene glycol (PEG)-modified granulocyte-macrophage colony-stimulating factor (GM-CSF) with conserved biological activity." Exp Hematol. Sep. 1992;20(8):1028-35.
Mann et al., "Development and implementation of a new rapid aneuploidy diagnostic service within the UK National Health Service and implications for the future of prenatal diagnosis." Lancet. Sep. 29, 2001;358(9287)1057-61.
Mann, K. Methods Mol Med 92:141-156 (2004).
Mao and Williamson (1999) Nucl. Acids Res. 27, 4059-4070.
Marais et al., EMBO J. 14: 3136-3145 (1995).
Marais et al., J. Biol. Chem. 272: 4378-4383 (1997.
Margulies et al., "Genome sequencing in microfabricated high-density picolitre reactors." Nature. Sep. 15, 2005;437(7057):376-80. Epub Jul. 31, 2005.
Mason et al., EMBO J. 18: 2137-2148 (1999.
McClelland, M. et al., "A single buffer for all restriction endonucleases," Nucl. Acids Res. 16:364 (1988).
McConnell, H. M. et al., Science 257: 1906-1912 (1992)).
Meller A. 2007 Clin Chem 53: 1996-2001.
Metzker M Nature Rev 11:31-46 (2010).
Meyers & Miller, CABIOS 4:11-17 (1989).
Mito, Y., Henikoff, J.G. & Henikoff, S. Nat Genet 37, 1090-7 (2005.
Molecular Cloning of PCR Products, Unit 15.4, Current Protocols in Molecular Biology, (2001 John Wiley & Sons, Inc.) 15.4.1-15.4.11, Supplement 56.
Moudrianakis E. N. and Beer M. Proc Natl Acad Sci USA. Mar. 1965; 53:564-71.
Mouliere et al., "High Fragmentation Characterizes Tumour-Derived Circulating DNA," PLoS ONE, Sep. 2011, vol. 6, Issue 9, e23438, 1-10.
Nakamaye et al., Nucl. Acids Res. 23:9947-9959(1988).
Nakano et al. "Single-molecule PCR using water-in-oil emulsion;" Journal of Biotechnology 102 (2003) 117-124.
Needham-VanDevanter et al., "Characterization of an adduct between CC-1065 and a defined oligodeoxynucleotide duplex." Nucleic Acids Res. Aug. 10, 1984;12(15):6159-68.
Needleman et al., "A general method applicable to the search for similarities in the amino acid sequence of two proteins." J Mol Biol. Mar. 1970;48(3)444-453.
Ng et al. , 2003, Proc. Natl. Acad. Sci. USA 100 : 4748-4753.
Ng et al., 2002, Clin. Chem. 48: 1212-1217.
Nicolaides et al., "One-stop clinic for assessment of risk of chromosomal defects at 12 weeks of gestation." J Matern Fetal Neonatal Med. Jul. 2002;12(1):9-18.
Nicolaides, K. H. et al., Prenat Diagn 22:308-315 (2002)).
Nicolaidis et al., "Origin and mechanisms of non-disjunction in human autosomal trisomies." Hum Reprod. Feb. 1998;13(2):313-9.

Nishizuka et al., "Proteomic profiling of the NCI-60 cancer cell lines using new high-density reverse-phase lysate microarrays." Proc Natl Acad Sci U S A. Nov. 25, 2003;100(24):14229-34. Epub Nov. 17, 2003.

Nolte, "Branched DNA signal amplification for direct quantitation of nucleic acid sequences in clinical specimens." Adv Clin Chem. 1998;33:201-35.

Nosaka, K. et al., "Increasing methylation of the CDKN2A gene is associated with the progression of adult T-cell leukemia", Cancer Res. 60(4):1043-1048 (2000).

Nygren et al., "Quantification of Fetal DNA by Use of Methylation-Based DNA Discrimination," Clinical Chemistry, 56:10, pp. 1627-1635.

Oefner, P. J. et al., "Efficient random subcloning of DNA sheared in a recirculating point-sink flow system," Nucl. Acids Res. 24(20):3879-3886 (1996).

Oeth et al., "Qualitative and quantitative genotyping using single base primer extension coupled with matrix-assisted laser desorption/ionization time-of-flight mass spectrometry (MassARRAY)." Methods Mol Biol. 2009;578:307-43.

Oeth, P. et al., (iPLEX™ Assay: Increased Plexing Efficiency and Flexibility for MassARRAY® System through single base primer extension with mass-modified Terminators. SEQUENOM Application Note (2005).

Ohm, J.E. et al. A stem cell-like chromatin pattern may predispose tumor suppressor genes to DNA hypermethylation and heritable silencing. Nat Genet 39, 237-42 (2007).

Ohtsuka et al., J. Biol. Chem. 260:2605-2608 (1985).

Okano et al., "DNA methyltransferases Dnmt3a and Dnmt3b are essential for de novo methylation and mammalian development." Cell. Oct. 29, 1999;99(3):247-57.

Old RW, "Candidate epigenetic biomarkers for non-invasive prenatal diagnosis of Down syndrom," Reprod Biomed. Online 2007, vol. 15, No. 2, pp. 227-235.

Olek et al., "A modified and improved method for bisulphite based cytosine methylation analysis." Nucleic Acids Res. Dec. 15, 1996;24(24):5064-6.

Oligonucleotides and Analogues, A Practical Approach, F. Eckstein, editor, IRL Press, Oxford, 1991.

Orita et al., Proc. Natl. Acad. Sci. U.S.A 86: 27776-2770 (1989.

Osborne, et al., Curr. Opin. Chem. Biol.1(1): 5-9 (1997.

Oudejans et al., 2003, Prenatal Diagnosis 23: 111-116.

Padilla et al., "Efficient synthesis of nucleic acids heavily modified with non-canonical ribose 2'-groups using a mutantT7 RNA polymerase (RNAP)." Nucleic Acids Res. Mar. 15, 1999;27(6)1561-3.

Palomaki et al., "Maternal serum screening for Down syndrome in the United States: a 1995 survey." Am J Obstet Gynecol. May 1997;176(5):1046-51.

Pandya et al., "Screening for fetal trisomies by maternal age and fetal nuchal translucency thickness at 10 to 14 weeks of gestation." Br J Obstet Gynaecol. Dec. 1995;102(12):957-62.

Patel, D. J., Curr. Opin. Chem. Biol. Jun;1(1): 32-46 (1997).

Paulin, R. et al. in Nucleic Acids Res. 26:5009-5010, 1998.

Pearson & Reanier, J. Chrom. 255: 137-149 (1983).

Pearson, 1988, Proc. Natl. Acad. Sci. USA 85(5): 2444-2448.

Perry-O'Keefe et al., "Peptide nucleic acid pre-gel hybridization: an alternative to southern hybridization." Proc Natl Acad Sci U S A. Dec. 10, 1996;93(25):14670-5.

Pertl et al., "Rapid molecular method for prenatal detection of Down's syndrome." Lancet. May 14, 1994;343(8907)1197-8.

Peters et al., "Noninvasive Prenatal Diagnosis of a Fetal Microdeletion Syndrome," New England Journal of Medicine, Nov. 10, 2011, pp. 1847-1848.

Petersen and Mikkelsen. Cytogenet Cell Genet. 2000;91(1-4):199-203.

Pinkert et al., Genes Dev. 1: 268-277 (1987).

Poon et al., 2000, Clin. Chem. 46: 1832-1834.

Poon et al., "Differential DNA methylation between fetus and mother as a strategy for detecting fetal DNA in maternal plasma." Clin Chem. Jan. 2002;48(1):35-41.

Porter et al., Biochemistry 34: 11963-11969 (1995).

Qu et al., "Analysis of drug-DNA binding data." Methods Enzymol. 2000;321:353-69.

Queen et al., "Immunoglobulin gene transcription is activated by downstream sequence elements." Cell. Jul. 1983;33(3):741-8.

Radding., "Homologous pairing and strand exchange in genetic recombination." Annu Rev Genet. 1982;16:405-37.

Randen et al., "Prenatal genotyping of RHD and SRY using maternal blood," VOX SANGUINIS, vol. 85, No. 4, Nov. 2003, pp. 300-306.

Rashtchian (1994, PCR Methods Applic. 4: S83-S91).

Rivas, G., and Minton, A. P., Trends Biochem Sci Aug;18(8): 284-7 (1993).

Robertson et al., Nature Rev. Genet. 1:11-19 (2000).

Robinson M. D. and T. P. Speed. "A comparison of Affymetrix gene expression arrays." BMC Bioinformatics 8:449 (2007).

Rojo et al., "Cusativin, a new cytidine-specific ribonuclease accumulated in seeds of *Cucumis sativus* L." Planta. 1994;194(3):328-38.

Rollins et al., "Large-scale structure of genomic methylation patterns." Genome Res. Feb. 2006;16(2):157-63. Epub Dec. 19, 2005.

Romero and Rotbard, Diagnostic Molecular Biology: Principles and Applications, pp. 401-406; Pershing et al, eds., Mayo Foundation, Rochester, Minn., 1993.

Roschke et al., "Karyotypic complexity of the NCI-60 drug-screening panel." Cancer Res. Dec. 15, 2003;63(24):8634-47.

Rosenberg, H. S. and Bendich, A. J. Am. Chem. Soc. 82:3198-3201 (1960).

Rossolini et al., Mol. Cell. Probes 8:91-98 (1994).

Sadri & Hornsby (Nucl. Acids Res. 24:5058-5059, 1996.

Saito et al., Lancet 356:1170, 2000.

Sambrook et al., Molecular Biology: A laboratory Approach, Cold Spring Harbor, N. Y. 1989.

Sanchez et al, "Effects of Sulpiride on Prolactin and mRNA Levels of Steroid 5a-reductase Isozymes in Adult Rat Brain," Neurochem Res (2008) 33:820-825.

Santoro, S. W. and Joyce, G. F. "A general purpose RNA-cleaving DNA enzyme," Proc. Natl. Acad. Sci. USA 94:4262-4266 (1997.

Sargent et al., Meth. Enz. 152:432 (1988)).

Schlesinger et al., "Polycomb-mediated methylation on Lys27 of histone H3 pre-marks genes for de novo methylation in cancer." Nat Genet. Feb. 2007;39(2):232-6. Epub Dec. 31, 2006.

Schouten et al., "Relative quantification of 40 nucleic acid sequences by multiplex ligation-dependent probe amplification." Nucleic Acids Res. Jun. 15, 2002;30(12):e57.

Schriefer, L. A. et al., "Low pressure DNA shearing: a method for random DNA sequence analysis," Nucl. Acids Res. 18:7455-7456 (1990.

Schuler GD, Sequence mapping by electronic PCR., Genome Res. May 1997;7(5):541-50.

Scott et al. (2004) J. Am. Chem. Soc. 126, 11776-11777.

Sekizawa et al., Clin. Chem. 47:2164-2165, 2001.

Sheffield et al., "Identification of novel rhodopsin mutations associated with retinitis pigmentosa by GC-clamped denaturing gradient gel electrophoresis." Am J Hum Genet. Oct. 1991;49(4):699-706.

Silverman et al., "Methylation inhibitor therapy in the treatment of myelodysplastic syndrome." Nat Clin Pract Oncol. Dec. 2005;2 Suppl 1:S12-23.

Simoncsits et al., "New rapid gel sequencing method for RNA." Nature. Oct. 27, 1977;269(5631):833-6.

Singer et al., Biotechniques 4:230, 1986.

Sjolander & Urbaniczk, Anal. Chem. 63: 2338-2345 (1991.

Slater et al., "Rapid, high throughput prenatal detection of aneuploidy using a novel quantitative method (MLPA)." J Med Genet. Dec. 2003;40(12):907-12.

Smith et al., "Identification of common molecular subsequences." J Mol Biol. Mar. 25, 1981;147(1):195-7.

Smith et al., "Single-step purification of polypeptides expressed in *Escherichia coli* as fusions with glutathione S-transferase." Gene. Jul. 15, 1988;67(1):31-40.

Snijders et al., "Assembly of microarrays for genome-wide measurement of DNA copy number." Nat Genet. Nov. 2001;29(3):263-4.

Snijders et al., "First-trimester ultrasound screening for chromosomal defects." Ultrasound Obstet Gynecol. Mar. 1996;7(3):216-26.

Snijders et al., "UK multicentre project on assessment of risk of trisomy 21 by maternal age and fetal nuchal-translucency thickness at 10-14 weeks of gestation. Fetal Medicine Foundation First Trimester Screening Group." Lancet. Aug. 1, 1998;352(9125):343-6.
Soni et al., "Progress toward ultrafast DNA sequencing using solid-state nanopores." Clin Chem. Nov. 2007;53(11):1996-2001. Epub Sep. 21, 2007.
Sousa et al., "A mutant T7 RNA polymerase as a DNA polymerase." EMBO J. Sep. 15, 1995;14(18):4609-21.
Spetzler et al, Enriching for Rare Subpopulations of Circulating Microvesicles by the Depletion of Endothelial-and Leukocyte-Derived Microvesicles, CARIS Life Sciences, Carisome Posters, Papers, Abstracts and Presentations, American Academy of Cancer Research (AACR 2011).
Stanssens et al., "High-throughput MALDI-TOF discovery of genomic sequence polymorphisms." Genome Res. Jan. 2004;14(1):126-33.
Staunton et al., "Chemosensitivity prediction by transcriptional profiling." Proc Natl Acad Sci U S A. Sep. 11, 2001;98(19):10787-92.
Strathdee, et al., Am. J. Pathol. 158:I121-1127 (2001).
Strohmeier, Fred, "A New High-Performance Capillary Electrophoresis Instrument," 10-19, Hewlett-Packard Journal, Jun. 1995.
Szabo et al., Curr. Opin. Struct. Biol. 5: 699-705 (1995).
Takai et al., Proc. Natl. Acad. Sci. U.S.A. 99:3740-3745, 2002).
Tang et al. (2002) Analytical Chemistry 74, 226-331.
The Cancer Test, Cell Free DNA, 2007, Health Screen Inc. printed from the internet on Mar. 20, 2011 (http://www.thecancertest.com/science-of-cell-free-dna/).
The Human Genome, T. Strachan, BIOS Scientific Publishers, 1992.
The World Health Organization histological typing of lung tumours, Am J Clin Pathol 1982; 77:123-136.
Thorstenson, Y.R. et al., "An Automated Hydrodynamic Process for Controlled, Unbiased DNA Shearing," Genome Research 8:848-855 (1998).
Tolbert and Williamson (1996) J. Am. Chem. Soc. 118, 7929-7940.
Tolbert and Williamson (1997) J. Am. Chem. Soc. 119, 12100-12108.
Tong et al., "Noninvasive Prenatal Detection of Fetal Trisomy 18 by Epigenetic Allelic Ratio Analysis in Maternal Plasma: Theoretical and Empirical Considerations," Clinical Chemistry 52:12, pp. 2149-2202.
Tooke N and Pettersson M. IVDT. Nov. 2004; 41.
Tost et al., Nucl. Acids Res. 37:e50 (2003).
Toyota et al., "Methylation profiling in acute myeloid leukemia." Blood. May 1, 2001;97(9):2823-9.
Toyota et al., Cancer Res. 59:2307-12, 1999.
Tungwiwat et al., "Non-invasive fetal sex determination using a conventional nested PCR analysis of fetal DNA in maternal plasma," Clinica Chimica Acta, vol. 334, No. 1-2, Aug. 2003, pp. 173-177.
Tynan et al., "Fractional DNA quantification by massively parallel shotgun sequencing-implications for fetal fraction measurement in maternal plasma," (Sequenom MME) ASHG Poster, 2011.
Uhlmann, K. et al. Electrophoresis 23:4072-4079 (2002.
Valk et al., "Prognostically useful gene-expression profiles in acute myeloid leukemia." N Engl J Med. Apr. 15, 2004;350(16):1617-28.
Valk-Lingbeek et al., "Stem cells and cancer; the polycomb connection." Cell. Aug. 20, 2004;118(4):409-18.
Van der Schoot, C.E., et al., Real-time PCR of bi-allelic insertion/deletion polymorphisms can serve as a reliable positive control for cell-free fetal DNA in non-invasive prenatal genotyping [abstract] Blood 102, 93a (2003).
Veltman et al., "High-throughput analysis of subtelomeric chromosome rearrangements by use of array-based comparative genomic hybridization." Am J Hum Genet. May 2002;70(5):1269-76. Epub Apr. 9, 2002.
Venter et al., "The sequence of the human genome." Science. Feb. 16, 2001;291(5507):1304-51.
Verbeck et al. in the Journal of Biomolecular Techniques (vol. 13, Issue 2, 56-61).
Verma et al., "Rapid and simple prenatal DNA diagnosis of Down's syndrome." Lancet. Jul. 4, 1998;352(9121):9-12.
Vincenet et al., "Helicase-Dependent isothermal DNA Amplification,"EMBO reports 5(8):795-800 (2004).
Vire et al., "The Polycomb group protein EZH2 directly controls DNA methylation." Nature. Feb. 16, 2006;439(7078):871-4. Epub Dec. 14, 2005.
Vogelstein et al., "Digital PCR." Proc Natl Acad Sci U S A. Aug. 3, 1999;96(16):9236-41.
Volkerding et al. Clin Chem 55:641-658 (2009).
Vu et al. "Symmetric and asymmetric DNA methylation in the human IGF2-H19 imprinted region," Genomics, Mar. 1;64(2):132-143. (2000).
Wada et al., "Codon usage tabulated from the GenBank genetic sequence data." Nucleic Acids Res. May 11, 1992;20 Suppl:2111-8.
Wald and Hackshaw, Prenat Diagn 17(9):821-829 (1997).
Wang, H. et al. BMC Genomics 7, 166 (2006.
Wapner et al., "First-trimester screening for trisomies 21 and 18." N Engl J Med. Oct. 9, 2003;349(15):1405-13.
Waterman et al., 1980, J. Mol. Biol. 147: 195-197.
Weber et al., Oncogene 19: 169-176 (2000.
Weisenberger, D.J. et al. Nat Genet 38, 787-93 (2006.
White et al., "Detecting single base substitutions as heteroduplex polymorphisms." Genomics. Feb. 1992;12(2):301-6.
Widschwendter, M. et al. Epigenetic stem cell signature in cancer. Nat Genet 39, 157-8 (2007).
Wilkinson, In situ Hybridization, Wilkinson ed., IRL Press, Oxford University Press, Oxford 1998.
Winoto et al., "A novel, inducible and T cell-specific enhancer located at the 3' end of the T cell receptor alpha locus." EMBO J. Mar. 1989;8(3):729-33.
Xiong & Laird, Nucleic Acids Res. 25:2532-2534, 1997.
Yamada et al. (Genome Research 14:247-266, 2004).
Yan et al., "A novel diagnostic strategy for trisomy 21 using short tandem repeats," Electrophoresis 2006, 27,416-422.
Zahra S, et al, Plasma microparticles are not elevated in fresh plasma from patients with gynaecologicalmalignancy-An observational study, Gynecol Onco, Oct. 2011;123(1):152-156.
Zervos et al., Cell 72:223-232 (1993.
Zhao et al., (2010) Pretat Diag 30(8):778-782.
Zheng et al., "Nonhematopoietically Derived DNA is Shorter than Hematopoietically Derived DNA in Plasma: A Transplantation Model," Clin Chem 58:2, Nov. 3, 2011.
Zhong et al., Am. J. Obstet. Gynecol. 184:414-419, 2001).
Zhong et al., Prenat. Diagn. 20:795-798, 2000.
Zimmermann Lecturer, et al., 'Serum parameters and nuchal translucency in first trimester screening for fetal chromosomal abnormalities', In: BJOG: An International Journal of Obstetrics & Gynaecology, 1996, vol. I03(1O), pp. 1009-1014.
Zimmermann, B. et al., Clin Chem 48:362-363 (2002).
Zuker "Mfold web server for nucleic acid folding and hybridization prediction," Nucleic Acids Res. 31(13), 3406-3415.
Supplementary European Search Report dated: Jul. 14, 2011 for European Application No. EP 09720284 filed: Mar. 10, 2009 based on internation application No. PCT/US2009/036683.
Extended European Search Report dated: Apr. 19, 2012 in European Application No. EP 09815148 filed: Sep. 16, 2009.
Extended European Search Report dated Jan. 4, 2012 in European Application No. EP10817598.5 filed: Mar. 18, 2010.
International Preliminary Report on Patentability dated: Sep. 3, 2009 in International Application No. PCT/US2008/54468 filed on Feb. 20, 2008.
International Search Report and Written Opinion dated: Sep. 23, 2008 in International Application No. PCT/US2008/54468 filed on Feb. 20, 2008.
International Preliminary Report on Patentability dated: Feb. 18, 2010 in International Application No. PCT/US2008/54470 filed on Feb. 20, 2008.
International Search Report and Written Opinion dated: Aug. 18, 2008 in International Application No. PCT/US2008/54470 filed on Feb. 20, 2008.
International Preliminary Report on Patentability dated: Dec. 30, 2009 in International Application No. PCT/US2008/066791 filed on Jun. 12, 2008.
International Search Report and Written Opinion dated: Dec. 22, 2008 in International Application No. PCT/US2008/066791 filed on Jun. 12, 2008.

International Preliminary Report on Patentability, mailed on Sep. 23, 2010 in International application No. PCT/US2009/036683 filed on: Mar. 10, 2009 and published as WO 09/114543 on Sep. 17, 2009.

Invitation to Pay Additional Fees and Partial International Search Report mailed on: Dec. 28, 2009 in International application No. PCT/US2009/036683 filed on: Mar. 10, 2009 and published as WO 09/114543 on Sep. 17, 2009.

International Search Report and Written Opinion, mailed on Feb. 24, 2010 in International application No. PCT/US2009/036683 filed on: Mar. 10, 2009 and published as WO 09/114543 on Sep. 17, 2009.

International Preliminary Report on Patentability mailed on: Mar. 31, 2011 in International Application No. PCT/US2009/057215 filed on Sep. 16, 2009 and published as: WO 10/033639 on Mar. 25, 2010.

International Search Report and Written Opinion mailed on: Dec. 29, 2010 in International Application No. PCT/US2009/057215 filed on Sep. 16, 2009 and published as: WO 10/033639 on Mar. 25, 2010.

International Preliminary Report on Patentability dated: Mar. 29, 2012 in International Application No. PCT/US2010/027879 filed on Mar. 18, 2010.

International Search Report and Written Opinion mailed on: Dec. 30, 2010 in International Application No. PCT/US2010/027879 filed on Mar. 18, 2010.

International Preliminary Report on Patentability dated: Jul. 5, 2012 in International Application No. PCT/US2010/061319 filed on Dec. 20, 2010.

International Search Report and Written Opinion dated: Sep. 21, 2011 in International Application No. PCT/US2010/061319 filed on Dec. 20, 2010.

International Search Report and Written Opinion dated: Jan. 10, 2013 in International Application No. PCT/US2012/035479 filed on Apr. 27, 2012.

Office Action dated: Oct. 28, 2010 in U.S. Appl. No. 12/401,493, filed Mar. 10, 2009 and published as: 2009/0317817 on: Dec. 24, 2009.

Office Action dated: Jul. 19, 2011 in U.S. Appl. No. 12/401,493, filed Mar. 10, 2009 and published as: 2009/0317817 on: Dec. 24, 2009.

Office Action dated: Jun. 15, 2012 in U.S. Appl. No. 12/561,241, filed Sep. 16, 2009.

Office Action dated: Sep. 24, 2012 in U.S. Appl. No. 13/458,036, filed Apr. 27, 2012 and published as: 2012/0264618 on: Oct. 18, 2012.

Office Action dated: Mar. 18, 2013 in U.S. Appl. No. 12/401,493 filed on: Mar. 10, 2009 and published as: 2009/0317817 on: Dec. 24, 2009.

Office Action dated: Feb. 27, 2013 in U.S. Appl. No. 12/561,241 filed on: Sep. 16, 2009.

Office Action dated: Apr. 5, 2013 in U.S. Appl. No. 13/495,975 filed on: Jun. 13, 2012.

Office Action dated: Apr. 5, 2013 in U.S. Appl. No. 13/517,532 filed on: Jun. 13, 2012.

Office Action dated: Apr. 12, 2013 in U.S. Appl. No. 12/727,198 filed on: Mar. 18, 2010.

Office Action dated: Jan. 28, 2013 in U.S. Appl. No. 13/457,978 filed on: Apr. 27, 2012 and published as: 2012/0276542 on: Oct. 1, 2012.

Office Action dated: Feb. 6, 2013 in U.S. Appl. No. 13/458,036 filed on: Apr. 27, 2012 and published as: 2012/0264618 on: Oct. 18, 2012.

International Search Report and Written Opinion dated: Apr. 5, 2013 in International Application No. PCT/US2012/043388 filed on Jun. 20, 2012 and published as: WO/2012/177792 on Dec. 27, 2012.

* cited by examiner

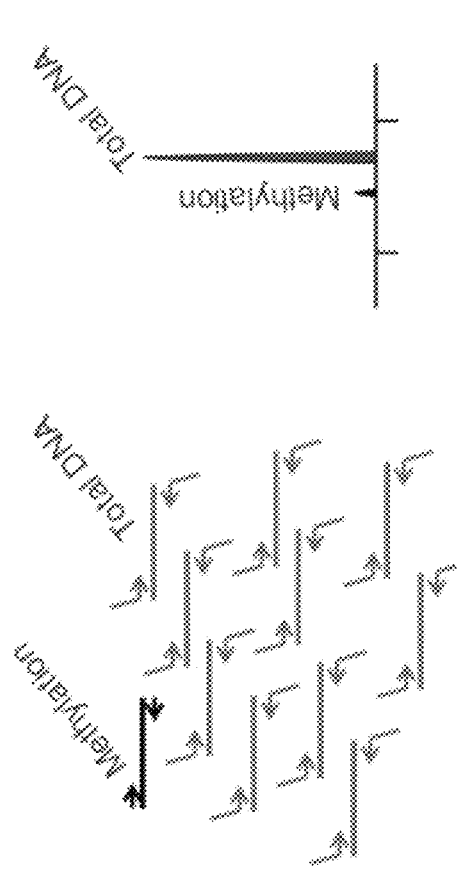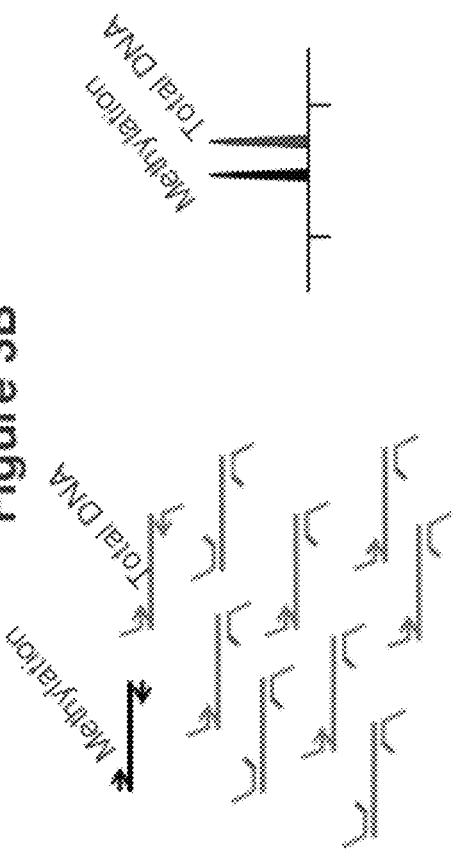

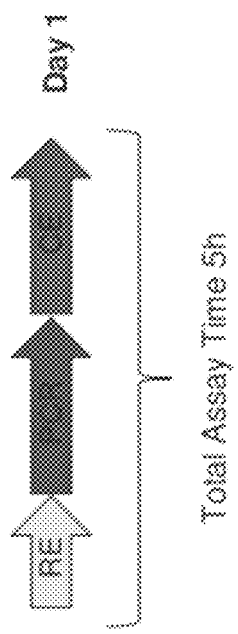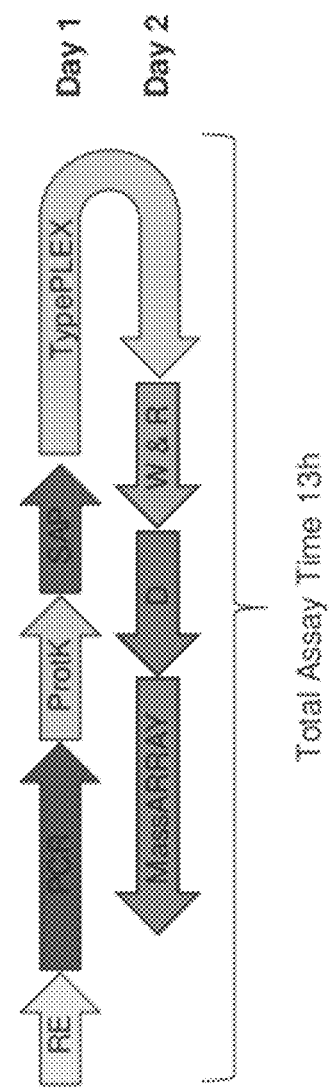

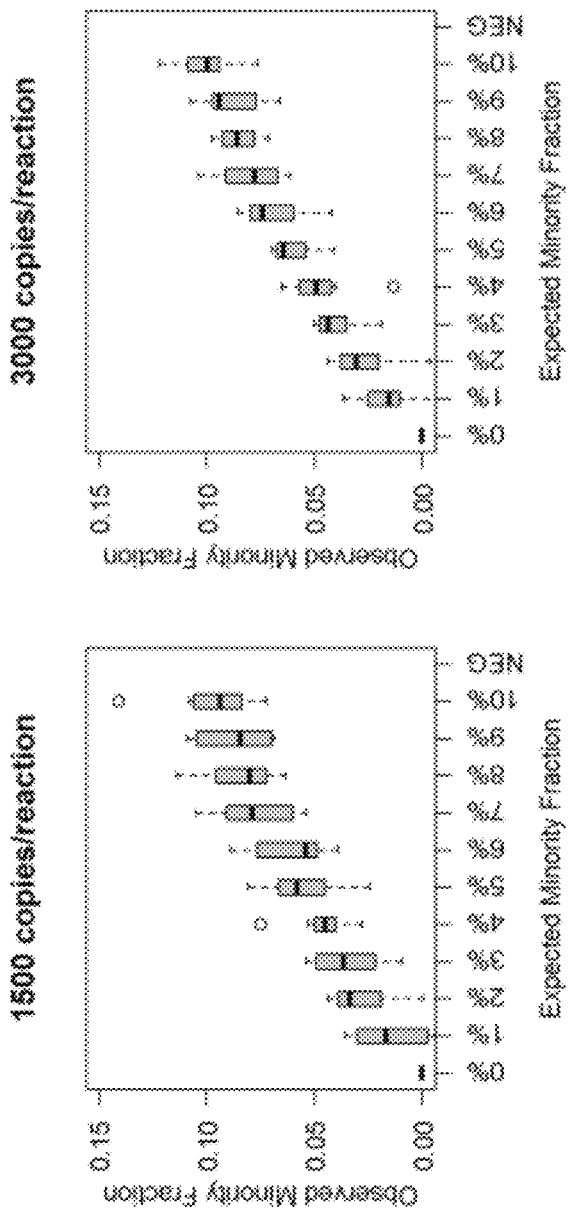

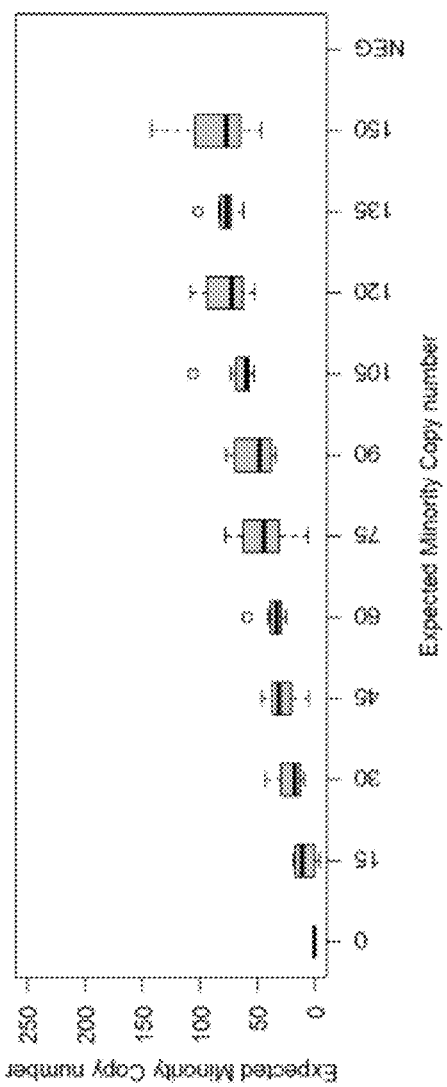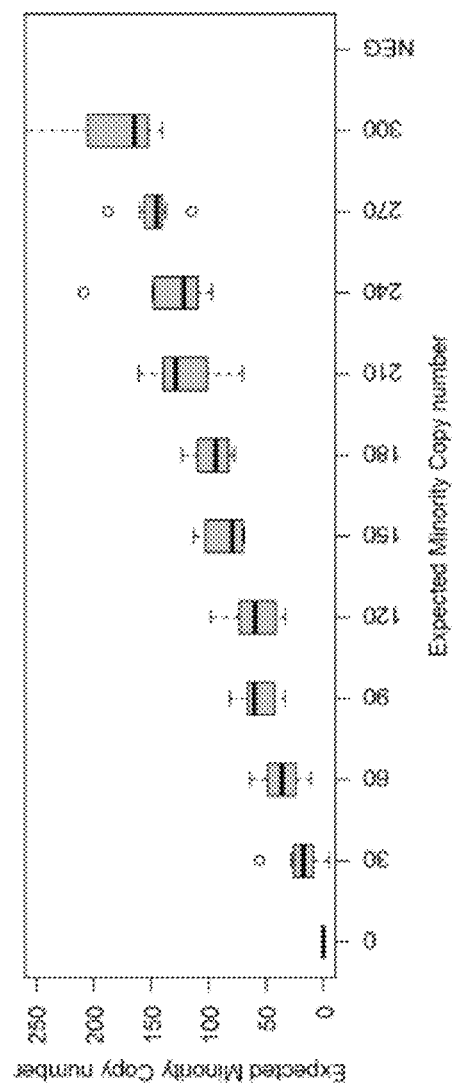
Figure 15A
Figure 15B

US 8,460,872 B2

QUANTIFICATION OF A MINORITY NUCLEIC ACID SPECIES

RELATED PATENT APPLICATION

This patent application claims the benefit of U.S. Provisional Application No. 61/480,686 filed on Apr. 29, 2011, entitled QUANTIFICATION OF A MINORITY NUCLEIC ACID SPECIES, naming Anders Nygren as inventor. The entirety of the foregoing provisional patent application is incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 25, 2012, is named SEQ631U3.txt and is 9,680 bytes in size.

FIELD

The technology relates in part to quantification of a minority nucleic acid species. In some embodiments, methods for determining the amount of cell-free fetal DNA in a maternal sample are provided.

BACKGROUND

Cell-free DNA (CF-DNA) is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

The presence of fetal nucleic acid in maternal plasma allows for non-invasive prenatal diagnosis through the analysis of a maternal blood sample. For example, quantitative abnormalities of fetal DNA in maternal plasma can be associated with a number of pregnancy-associated disorders, including preeclampsia, preterm labor, antepartum hemorrhage, invasive placentation, fetal Down syndrome, and other fetal chromosomal aneuploidies. Hence, fetal nucleic acid analysis in maternal plasma is a useful mechanism for the monitoring of fetomaternal well-being.

Early detection of pregnancy-related conditions, including complications during pregnancy and genetic defects of the fetus is important, as it allows early medical intervention necessary for the safety of both the mother and the fetus. Prenatal diagnosis traditionally has been conducted using cells isolated from the fetus through procedures such as chorionic villus sampling (CVS) or amniocentesis. However, these conventional methods are invasive and present an appreciable risk to both the mother and the fetus. The National Health Service currently cites a miscarriage rate of between 1 and 2 percent following the invasive amniocentesis and chorionic villus sampling (CVS) tests. An alternative to these invasive approaches is the use of non-invasive screening techniques that utilize circulating CFF-DNA.

SUMMARY

Provided in some embodiments is a method for determining the amount of a minority nucleic acid species in a sample which contains a minority species and a majority species, the combination of the minority species and the majority species comprising total nucleic acid in the sample, comprising (a) contacting under amplification conditions a nucleic acid sample comprising the minority nucleic acid species with: (i) a first set of amplification primers that specifically amplify a first region comprising a feature that (1) is present in the minority nucleic acid species and is not present in the majority nucleic acid species, or (2) is not present in the minority nucleic acid species and is present in the majority nucleic acid species, (ii) a second set of amplification primers that amplify a second region allowing for a determination of total nucleic acid in the sample, where the first region and the second region are different, and (iii) one or more inhibitory oligonucleotides that reduce the amplification of the second region, thereby generating minority and total nucleic acid amplification products, where the total nucleic acid amplification products are reduced relative to total amplification products that would be generated if no inhibitory oligonucleotide was present, (b) separating the minority and total nucleic acid amplification products, thereby generating separated minority and total nucleic acid amplification products, and (c) determining the fraction of the minority nucleic acid species in the sample relative to the total amount of the nucleic acid in the sample based on the amount of each of the separated minority and total nucleic acid amplification products.

In some cases, the feature that is present in the minority nucleic acid species and not present in the majority nucleic acid species is methylation. Sometimes the first region is methylated and the second region is unmethylated.

In some embodiments, the method further comprises contacting the nucleic acid sample with one or more restriction enzymes prior to (a). Sometimes the one or more restriction enzymes are methylation sensitive. In some cases, the restriction enzymes are HhaI and HpaII.

In some embodiments, the method further comprises contacting under amplification conditions the nucleic acid sample with a third set of amplification primers that amplify a third region allowing for a determination of the presence or absence of fetal specific nucleic acid. In some cases, the fetal specific nucleic acid is Y chromosome nucleic acid.

In some embodiments, the method further comprises contacting under amplification conditions the nucleic acid sample with a fourth set of amplification primers that amplify a fourth region allowing for a determination of the amount of digested or undigested nucleic acid, as an indicator of digestion efficiency. Often, the first, second, third and fourth regions each comprise one or more genomic loci. In some cases, the genomic loci are the same length. In some cases, the genomic loci are about 50 base pairs to about 200 base pairs. In some cases, the genomic loci are about 60 base pairs to about 80 base pairs. In some cases, the genomic loci are about 70 base pairs.

In some embodiments, the first region comprises one or more loci that are differentially methylated between the minority and majority species. In some cases, first region comprises loci within the TBX3 and SOX14 genes. In some cases, the loci for the first region each comprise independently SEQ ID NO:29 and SEQ ID NO:30.

In some embodiments, the second region comprises one or more loci which do not contain a restriction site for a methylation-sensitive restriction enzyme. In some cases, the second region comprises loci within the POP5 and APOE genes. In some cases, the loci for the second region each comprise independently SEQ ID NO:31 and SEQ ID NO:32.

In some embodiments, the third region comprises one or more loci within chromosome Y. In some cases, the third region comprises a locus within the DDX3Y gene. In some cases, the locus for the third region comprises SEQ ID NO:34.

In some embodiments, the fourth region comprises one or more loci present in every genome in the sample and unmethylated in all species. In some cases, the fourth region comprises loci within the POP5 or LDHA genes. In some cases, the loci for the fourth region each comprise independently SEQ ID NO:35 and SEQ ID NO:36.

In some embodiments, the first and second sets of amplification primers each comprise one or more pairs of forward and reverse primers. In some embodiments, the third and fourth sets of amplification primers each comprise one or more pairs of forward and reverse primers. In some cases, the one or more amplification primer pairs further comprise a 5' tail. Sometimes the 5' tail is a distinct length for each amplification primer set. In some cases, the amplification primers each comprise independently SEQ ID NOs:1 to 8 and SEQ ID NOs:11 to 16.

In some embodiments, an inhibitory oligonucleotide of the one or more inhibitory oligonucleotides comprises a nucleotide sequence complementary to a nucleotide sequence in the second region. In some cases, the inhibitory oligonucleotide and a primer in the second set of amplification primers are complementary to the same nucleotide sequence in the second region. In some cases, the inhibitory oligonucleotide comprises one or more 3' mismatched nucleotides. In some cases, the inhibitory oligonucleotides each comprise independently SEQ ID NO:17, SEQ ID NO:18, SEQ ID NO:19, and SEQ ID NO:20.

In some embodiments, the method further comprises contacting under amplification conditions the nucleic acid sample with one or more first competitor oligonucleotides that compete with the first region for hybridization of primers of the first amplification primer set. In some embodiments, the method further comprises contacting under amplification conditions the nucleic acid sample with one or more second competitor oligonucleotides that compete with the second region for hybridization of primers of the second amplification primer set. In some embodiments, the method further comprises contacting under amplification conditions the nucleic acid sample with one or more third competitor oligonucleotides that compete with the third region for hybridization of primers of the third amplification primer set. In some embodiments, the method further comprises contacting under amplification conditions the nucleic acid sample with one or more fourth competitor oligonucleotides that compete with the fourth region for hybridization of primers of the fourth amplification primer set. In some cases, the competitor oligonucleotides comprise a stuffer sequence. In some cases, the stuffer sequence length is constant for one or more of the first competitor oligonucleotides, second competitor oligonucleotides, third competitor oligonucleotides and fourth competitor oligonucleotides. In some cases, the stuffer sequence length is variable for one or more of the first competitor oligonucleotides, second competitor oligonucleotides, third competitor oligonucleotides and fourth competitor oligonucleotides. At times, the stuffer sequence is from a non-human genome. Sometimes the stuffer sequence is from the PhiX 174 genome. In some embodiments, the competitor oligonucleotide is about 100 to about 150 base pairs long. In some cases, the competitor oligonucleotide is about 115 to about 120 base pairs long. In some cases, the first and second competitor oligonucleotide is about 115 base pairs long. In some cases, the third competitor oligonucleotide is about 118 base pairs long. In some cases, the fourth competitor oligonucleotide is about 120 base pairs long. In some embodiments, the one or more first competitor oligonucleotides each comprise independently SEQ ID NO:21 and SEQ ID NO:22. In some embodiments, the one or more second competitor oligonucleotides each comprise independently SEQ ID NO:23 and SEQ ID NO:24. In some embodiments, the third competitor oligonucleotide comprises SEQ ID NO:26. In some embodiments, the one or more fourth competitor oligonucleotides each comprise independently SEQ ID NO:27 and SEQ ID NO:28. In some embodiments, the one or more competitor oligonucleotides comprise a detectable label. In some cases, the detectable label is a fluorophore and sometimes the fluorophore is different for each competitor oligonucleotide. In some embodiments, a predetermined copy number of each competitor oligonucleotide is used. In some embodiments, the method further comprises determining the copy number of the minority nucleic acid species based on the amount of competitor oligonucleotide used. In some embodiments, the method further comprises determining the copy number of the majority nucleic acid species.

In some embodiments, the sample nucleic acid is extracellular nucleic acid. In some embodiments, the minority nucleic acid species is fetal DNA and the majority nucleic acid species is maternal DNA. In some cases, the nucleic acid sample is obtained from a pregnant female subject. In some cases, the subject is human. In some embodiments, the sample nucleic acid is from plasma. In some cases, the sample nucleic acid is from serum.

In some embodiments, the amplification is in a single reaction vessel. Sometimes two or more of the amplification products are different lengths. Often, the amplification is by polymerase chain reaction (PCR). In some embodiments, the method further comprises contacting the amplification products with an exonuclease prior to (b). In some cases, the separation of amplification products is based on length. Often, the separation is performed using electrophoresis. In some cases, the electrophoresis is capillary electrophoresis. In some embodiments, the method further comprises determining whether the nucleic acid sample is utilized for a sequencing reaction. In some cases, the sequencing reaction is a reversible terminator-based sequencing reaction. In some embodiments, the method further comprises determining whether sequencing information obtained for a nucleic acid sample is used for a diagnostic determination.

Also provided in some embodiments is a method for determining the amount of a minority nucleic acid species in a sample which contains a minority species and a majority species, the combination of the minority species and the majority species comprising total nucleic acid in the sample, comprising a method of determining the copy number of the minority nucleic acid species, comprising the steps of (a) contacting under amplification conditions a nucleic acid sample comprising the minority nucleic acid species with (i) a first set of amplification primers that specifically amplify a first region comprising a feature that (1) is present in the minority nucleic acid species and is not present in the majority nucleic acid species, or (2) is not present in the minority nucleic acid species and is present in the majority nucleic acid species, (ii) a second set of amplification primers that amplify a second region allowing for a determination of the total nucleic acid in the sample, where the first region and the second region are different, (iii) one or more first competitor oligonucleotides that compete with the first region for hybridization of primers of the first amplification primer set, and (iv) one or more second competitor oligonucleotides that compete with the second region for hybridization of primers of the second amplification primer set, thereby generating amplification products where two or more of the amplification products are different lengths; (b) separating the minority nucleic acid, total nucleic acid, and competitor amplification products, thereby generating separated minority nucleic acid, total nucleic acid, and competitor amplification products; and (c) determining the copy number of the minority nucleic acid species in the sample based on the separated amplification products.

In some cases, the feature that is present in the minority nucleic acid species and not present in the majority nucleic acid species is methylation. Sometimes the first region is methylated and the second region is unmethylated.

In some embodiments, the method further comprises contacting the nucleic acid sample with one or more restriction enzymes prior to (a). Sometimes the one or more restriction enzymes are methylation sensitive. In some cases, the restriction enzymes are HhaI and HpaII.

In some embodiments, the method further comprises contacting under amplification conditions the nucleic acid sample with a third set of amplification primers that amplify a third region allowing for a determination of the presence or absence of fetal specific nucleic acid. In some cases, the fetal specific nucleic acid is Y chromosome nucleic acid.

In some embodiments, the method further comprises contacting under amplification conditions the nucleic acid sample with a fourth set of amplification primers that amplify a fourth region allowing for a determination of the amount of digested or undigested nucleic acid, as an indicator of digestion efficiency. Often, the first, second, third and fourth regions each comprise one or more genomic loci. In some cases, the genomic loci are the same length. In some cases, the genomic loci are about 50 base pairs to about 200 base pairs. In some cases, the genomic loci are about 60 base pairs to about 80 base pairs. In some cases, the genomic loci are about 70 base pairs.

In some embodiments, the first region comprises one or more loci that are differentially methylated between the minority and majority species. In some cases, first region comprises loci within the TBX3 and SOX14 genes. In some cases, the loci for the first region each comprise independently SEQ ID NO:29 and SEQ ID NO:30.

In some embodiments, the second region comprises one or more loci which do not contain a restriction site for a methylation-sensitive restriction enzyme. In some cases, the second region comprises loci within the POP5 and APOE genes. In some cases, the loci for the second region each comprise independently SEQ ID NO:31 and SEQ ID NO:32.

In some embodiments, the third region comprises one or more loci within chromosome Y. In some cases, the third region comprises a locus within the DDX3Y gene. In some cases, the locus for the third region comprises SEQ ID NO:34.

In some embodiments, the fourth region comprises one or more loci present in every genome in the sample and unmethylated in all species. In some cases, the fourth region comprises loci within the POP5 or LDHA genes. In some cases, the loci for the fourth region each comprise independently SEQ ID NO:35 and SEQ ID NO:36.

In some embodiments, the first and second sets of amplification primers each comprise one or more pairs of forward and reverse primers. In some embodiments, the third and fourth sets of amplification primers each comprise one or more pairs of forward and reverse primers. In some cases, the one or more amplification primer pairs further comprise a 5' tail. Sometimes the 5' tail is a distinct length for each amplification primer set. In some cases, the amplification primers each comprise independently SEQ ID NOs:1 to 8 and SEQ ID NOs:11 to 16.

In some embodiments, the method further comprises contacting under amplification conditions the nucleic acid sample with one or more inhibitory oligonucleotides that reduce the amplification of the second region. In some embodiments, an inhibitory oligonucleotide of the one or more inhibitory oligonucleotides comprises a nucleotide sequence complementary to a nucleotide sequence in the second region. In some cases, the inhibitory oligonucleotide and a primer in the second set of amplification primers are complementary to the same nucleotide sequence in the second region. In some cases, the inhibitory oligonucleotide comprises one or more 3' mismatched nucleotides. In some cases, the inhibitory oligonucleotides each comprise independently SEQ ID NO:17, SEQ ID NO:18, SEQ ID NO:19, and SEQ ID NO:20.

In some embodiments, the method further comprises determining the fraction of the minority nucleic acid species in the sample relative to the total amount of the nucleic acid in the sample based on the amount of each of the separated minority and total nucleic acid amplification products.

In some embodiments, the method further comprises contacting under amplification conditions the nucleic acid sample with one or more third competitor oligonucleotides that compete with the third region for hybridization of primers of the third amplification primer set. In some embodiments, the method further comprises contacting under amplification conditions the nucleic acid sample with one or more fourth competitor oligonucleotides that compete with the fourth region for hybridization of primers of the fourth amplification primer set. In some cases, the competitor oligonucleotides comprise a stuffer sequence. In some cases, the stuffer sequence length is constant for one or more of the first competitor oligonucleotides, second competitor oligonucleotides, third competitor oligonucleotides and fourth competitor oligonucleotides. In some cases, the stuffer sequence length is variable for one or more of the first competitor oligonucleotides, second competitor oligonucleotides, third competitor oligonucleotides and fourth competitor oligonucleotides. At times, the stuffer sequence is from a non-human genome. Sometimes the stuffer sequence is from the PhiX 174 genome. In some embodiments, the competitor oligonucleotide is about 100 to about 150 base pairs long. In some cases, the competitor oligonucleotide is about 115 to about 120 base pairs long. In some cases, the first and second competitor oligonucleotide is about 115 base pairs long. In some cases, the third competitor oligonucleotide is about 118 base pairs long. In some cases, the fourth competitor oligonucleotide is about 120 base pairs long. In some embodiments, the one or more first competitor oligonucleotides each comprise independently SEQ ID NO:21 and SEQ ID NO:22. In some embodiments, the one or more second competitor oligonucleotides each comprise independently SEQ ID NO:23 and SEQ ID NO:24. In some embodiments, the third competitor oligonucleotide comprises SEQ ID NO:26. In some embodiments, the one or more fourth competitor oligonucleotides each comprise independently SEQ ID NO:27 and SEQ ID NO:28. In some embodiments, the one or more competitor oligonucleotides comprise a detectable label. In some cases, the detectable label is a fluorophore and sometimes the fluorophore is different for each competitor oligonucleotide. In some embodiments, a predetermined copy number of each competitor oligonucleotide is used. In some cases, the copy number of the minority nucleic acid species is determined based on the amount of competitor oligonucleotide used. In some cases, the copy number of the majority nucleic acid species is determined.

In some embodiments, the sample nucleic acid is extracellular nucleic acid. In some embodiments, the minority nucleic acid species is fetal DNA and the majority nucleic acid species is maternal DNA. In some cases, the nucleic acid sample is obtained from a pregnant female subject. In some cases, the subject is human. In some embodiments, the sample nucleic acid is from plasma. In some cases, the sample nucleic acid is from serum.

In some embodiments, the amplification is in a single reaction vessel. Sometimes two or more of the amplification products are different lengths. Often, the amplification is by polymerase chain reaction (PCR). In some embodiments, the method further comprises contacting the amplification products with an exonuclease prior to (b). In some cases, the separation of amplification products is based on length. Often, the separation is performed using electrophoresis. In some cases, the electrophoresis is capillary electrophoresis. In some embodiments, the method further comprises determining whether the nucleic acid sample is utilized for a sequencing reaction. In some cases, the sequencing reaction is a reversible terminator-based sequencing reaction. In some embodiments, the method further comprises determining whether sequencing information obtained for a nucleic acid sample is used for a diagnostic determination.

Also provided in some embodiments is a method for determining the amount of a minority nucleic acid species in a sample which contains a minority nucleic acid species and a majority species, the combination of the minority species and the majority species comprising total nucleic acid in the sample, comprising: (a) contacting under amplification conditions a nucleic acid sample comprising the minority nucleic acid species with: (i) a first set of amplification primers that specifically amplify a first region comprising a feature that (1) is present in the minority nucleic acid species and is not present in the majority nucleic acid species, or (2) is not present in the minority nucleic acid species and is present in the majority nucleic acid species, (ii) a second set of amplification primers that amplify a second region allowing for a determination of total nucleic acid in the sample, where the first region and the second region are different, (iii) one or more inhibitory oligonucleotides that reduce the amplification of the second region, (iv) one or more first competitor oligonucleotides that compete with the first region for hybridization of primers of the first amplification primer set, and (v) one or more second competitor oligonucleotides that compete with the second region for hybridization of primers of the second amplification primer set, thereby generating minority nucleic acid, total nucleic acid and competitor amplification products, where two or more of the amplification products are different lengths and the total nucleic acid amplification products are reduced relative to total amplification products that would be generated if no inhibitory oligonucleotide was present, (b) separating the amplification products, thereby generating separated minority nucleic acid, total nucleic acid and competitor amplification products, and (c) determining the amount of the minority nucleic acid species in the sample based on the separated amplification products.

In some cases, the feature that is present in the minority nucleic acid species and not present in the majority nucleic acid species is methylation. Sometimes the first region is methylated and the second region is unmethylated.

In some embodiments, the method further comprises contacting the nucleic acid sample with one or more restriction enzymes prior to (a). Sometimes the one or more restriction enzymes are methylation sensitive. In some cases, the restriction enzymes are HhaI and HpaII.

In some embodiments, the method further comprises contacting under amplification conditions the nucleic acid sample with a third set of amplification primers that amplify a third region allowing for a determination of the presence or absence of fetal specific nucleic acid. In some cases, the fetal specific nucleic acid is Y chromosome nucleic acid.

In some embodiments, the method further comprises contacting under amplification conditions the nucleic acid sample with a fourth set of amplification primers that amplify a fourth region allowing for a determination of the amount of digested or undigested nucleic acid, as an indicator of digestion efficiency. Often, the first, second, third and fourth regions each comprise one or more genomic loci. In some cases, the genomic loci are the same length. In some cases, the genomic loci are about 50 base pairs to about 200 base pairs. In some cases, the genomic loci are about 60 base pairs to about 80 base pairs. In some cases, the genomic loci are about 70 base pairs.

In some embodiments, the first region comprises one or more loci that are differentially methylated between the minority and majority species. In some cases, first region comprises loci within the TBX3 and SOX14 genes. In some cases, the loci for the first region each comprise independently SEQ ID NO:29 and SEQ ID NO:30.

In some embodiments, the second region comprises one or more loci which do not contain a restriction site for a methylation-sensitive restriction enzyme. In some cases, the second region comprises loci within the POP5 and APOE genes. In some cases, the loci for the second region each comprise independently SEQ ID NO:31 and SEQ ID NO:32.

In some embodiments, the third region comprises one or more loci within chromosome Y. In some cases, the third region comprises a locus within the DDX3Y gene. In some cases, the locus for the third region comprises SEQ ID NO:34.

In some embodiments, the fourth region comprises one or more loci present in every genome in the sample and unmethylated in all species. In some cases, the fourth region comprises loci within the POP5 or LDHA genes. In some cases, the loci for the fourth region each comprise independently SEQ ID NO:35 and SEQ ID NO:36.

In some embodiments, the first and second sets of amplification primers each comprise one or more pairs of forward and reverse primers. In some embodiments, the third and fourth sets of amplification primers each comprise one or more pairs of forward and reverse primers. In some cases, the one or more amplification primer pairs further comprise a 5' tail. Sometimes the 5' tail is a distinct length for each amplification primer set. In some cases, the amplification primers each comprise independently SEQ ID NOs:1 to 8 and SEQ ID NOs:11 to 16.

In some embodiments, an inhibitory oligonucleotide of the one or more inhibitory oligonucleotides comprises a nucleotide sequence complementary to a nucleotide sequence in the second region. In some cases, the inhibitory oligonucleotide and a primer in the second set of amplification primers are complementary to the same nucleotide sequence in the second region. In some cases, the inhibitory oligonucleotide comprises one or more 3' mismatched nucleotides. In some cases, the inhibitory oligonucleotides each comprise independently SEQ ID NO:17, SEQ ID NO:18, SEQ ID NO:19, and SEQ ID NO:20.

In some embodiments, the amount of the minority nucleic acid determined is the fraction of the minority nucleic acid species in the sample relative to the total amount of the nucleic acid in the sample based on the amount of each of the separated minority and total nucleic acid amplification products.

In some embodiments, the method further comprises contacting under amplification conditions the nucleic acid sample with one or more third competitor oligonucleotides that compete with the third region for hybridization of primers of the third amplification primer set. In some embodiments, the method further comprises contacting under amplification conditions the nucleic acid sample with one or more fourth competitor oligonucleotides that compete with the fourth region for hybridization of primers of the fourth amplification primer set. In some cases, the competitor oligonucleotides comprise a stuffer sequence. In some cases, the stuffer sequence length is constant for one or more of the first competitor oligonucleotides, second competitor oligonucleotides, third competitor oligonucleotides and fourth competitor oligonucleotides. In some cases, the stuffer sequence length is variable for one or more of the first competitor oligonucleotides, second competitor oligonucleotides, third competitor oligonucleotides and fourth competitor oligonucleotides. At times, the stuffer sequence is from a non-human genome. Sometimes the stuffer sequence is from the PhiX 174 genome. In some embodiments, the competitor oligonucleotide is about 100 to about 150 base pairs long. In some cases, the competitor oligonucleotide is about 115 to about 120 base pairs long. In some cases, the first and second competitor oligonucleotide is about 115 base pairs long. In some cases, the third competitor oligonucleotide is about 118 base pairs long. In some cases, the fourth competitor oligonucleotide is about 120 base pairs long. In some embodiments, the one or more first competitor oligonucleotides each comprise independently SEQ ID NO:21 and SEQ ID NO:22. In some embodiments, the one or more second competitor oligonucleotides each comprise independently SEQ ID NO:23 and SEQ ID NO:24. In some embodiments, the third competitor oligonucleotide comprises SEQ ID NO:26. In some embodiments, the one or more fourth competitor oligonucleotides each comprise independently SEQ ID NO:27 and SEQ ID NO:28. In some embodiments, the one or more competitor oligonucleotides comprise a detectable label. In some cases, the detectable label is a fluorophore and sometimes the fluorophore is different for each competitor oligonucleotide. In some embodiments, a predetermined copy number of each competitor oligonucleotide is used. In some cases, the amount of the minority nucleic acid determined is the copy number of the minority nucleic acid species based on the amount of competitor oligonucleotide used. In some cases, the copy number of the majority nucleic acid species is determined.

In some embodiments, the sample nucleic acid is extracellular nucleic acid. In some embodiments, the minority nucleic acid species is fetal DNA and the majority nucleic acid species is maternal DNA. In some cases, the nucleic acid sample is obtained from a pregnant female subject. In some cases, the subject is human. In some embodiments, the sample nucleic acid is from plasma. In some cases, the sample nucleic acid is from serum.

In some embodiments, the amplification is in a single reaction vessel. Sometimes two or more of the amplification products are different lengths. Often, the amplification is by polymerase chain reaction (PCR). In some embodiments, the method further comprises contacting the amplification products with an exonuclease prior to (b). In some cases, the separation of amplification products is based on length. Often, the separation is performed using electrophoresis. In some cases, the electrophoresis is capillary electrophoresis. In some embodiments, the method further comprises determining whether the nucleic acid sample is utilized for a sequencing reaction. In some cases, the sequencing reaction is a reversible terminator-based sequencing reaction. In some embodiments, the method further comprises determining whether sequencing information obtained for a nucleic acid sample is used for a diagnostic determination.

Also provided in some embodiments is a method for determining the amount of fetal nucleic acid in a sample, which contains fetal nucleic acid and maternal nucleic acid, the combination of the fetal species and the maternal species comprising total nucleic acid in the sample, comprising (a) contacting under amplification conditions a nucleic acid sample comprising fetal nucleic acid with: (i) a first set of amplification primers that specifically amplify a first region comprising a feature that (1) is present in the fetal nucleic acid and is not present in the maternal nucleic acid, or (2) is not present in the fetal nucleic acid and is present in the maternal nucleic acid, (ii) a second set of amplification primers that amplify a second region allowing for a determination of the total nucleic acid in the sample, (iii) one or more inhibitory oligonucleotides that reduce the amplification of the second region, (iv) a third set of amplification primers that amplify a third region allowing for a determination of the presence or absence of Y chromosome nucleic acid, (v) a fourth set of amplification primers that amplify a fourth region allowing for a determination of the amount of digested or undigested nucleic acid, as an indicator of digestion efficiency, where the first, second, third and fourth regions are different, (vi) one or more first competitor oligonucleotides that compete with the first region for hybridization of primers of the first amplification primer set, (vii) one or more second competitor oligonucleotides that compete with the second region for hybridization of primers of the second amplification primer set, (viii) one or more third competitor oligonucleotides that compete with the third region for hybridization of primers of the third amplification primer set, and (ix) one or more fourth competitor oligonucleotides that compete with the fourth region for hybridization of primers of the fourth amplification primer set, thereby generating fetal nucleic acid, total nucleic acid, Y chromosome nucleic acid, digestion efficiency indicator and competitor amplification products, where two or more of the amplification products are different lengths and the total nucleic acid amplification products are reduced relative to total amplification products that would be generated if no inhibitory oligonucleotide was present (b) separating the amplification products, thereby generating separated fetal nucleic acid, total nucleic acid, Y chromosome nucleic acid, digestion efficiency indicator, and competitor amplification products, and (c) determining the amount of the fetal nucleic acid in the sample based on the separated amplification products.

In some embodiments, the feature that is present in the fetal nucleic acid and not present in the maternal nucleic acid is methylation. Sometimes the first region is methylated and the second region is unmethylated. In some embodiments, the method further comprises contacting the nucleic acid sample with one or more restriction enzymes prior to (a). In some cases, the one or more restriction enzymes are methylation sensitive. Sometimes the restriction enzymes are HhaI and HpaII.

In some embodiments, the first, second, third and fourth regions each comprise one or more genomic loci. In some cases, the genomic loci are the same length. In some cases, the genomic loci are about 50 base pairs to about 200 base pairs. In some cases, the genomic loci are about 60 base pairs to about 80 base pairs. In some cases, the genomic loci are about 70 base pairs.

In some embodiments, the first region comprises one or more loci that are differentially methylated between the fetal and maternal species. In some cases, first region comprises loci within the TBX3 and SOX14 genes. In some cases, the loci for the first region each comprise independently SEQ ID NO:29 and SEQ ID NO:30.

In some embodiments, the second region comprises one or more loci which do not contain a restriction site for a methylation-sensitive restriction enzyme. In some cases, the second region comprises loci within the POP5 and APOE genes. In some cases, the loci for the second region each comprise independently SEQ ID NO:31 and SEQ ID NO:32.

In some embodiments, the third region comprises one or more loci within chromosome Y. In some cases, the third region comprises a locus within the DDX3Y gene. In some cases, the locus for the third region comprises SEQ ID NO:34.

In some embodiments, the fourth region comprises one or more loci present in every genome in the sample and unmethylated in fetal and maternal nucleic acid. In some cases, the fourth region comprises loci within the POP5 or LDHA genes. In some cases, the loci for the fourth region each comprise independently SEQ ID NO:35 and SEQ ID NO:36.

In some embodiments, the first and second sets of amplification primers each comprise one or more pairs of forward and reverse primers. In some embodiments, the third and fourth sets of amplification primers each comprise one or more pairs of forward and reverse primers. In some cases, the one or more amplification primer pairs further comprise a 5' tail. Sometimes the 5' tail is a distinct length for each amplification primer set. In some cases, the amplification primers each comprise independently SEQ ID NOs:1 to 8 and SEQ ID NOs:11 to 16.

In some embodiments, an inhibitory oligonucleotide of the one or more inhibitory oligonucleotides comprises a nucleotide sequence complementary to a nucleotide sequence in the second region. In some cases, the inhibitory oligonucleotide and a primer in the second set of amplification primers are complementary to the same nucleotide sequence in the second region. In some cases, the inhibitory oligonucleotide comprises one or more 3' mismatched nucleotides. In some cases, the inhibitory oligonucleotides each comprise independently SEQ ID NO:17, SEQ ID NO:18, SEQ ID NO:19, and SEQ ID NO:20.

In some embodiments, the amount of the fetal nucleic acid determined is the fraction of the fetal nucleic acid in the sample relative to the total amount of nucleic acid in the sample based on the amount of each of the separated fetal and total nucleic acid amplification products.

In some embodiments, the competitor oligonucleotides comprise a stuffer sequence. In some cases, the stuffer sequence length is constant for one or more of the first competitor oligonucleotides, second competitor oligonucleotides, third competitor oligonucleotides and fourth competitor oligonucleotides. In some cases, the stuffer sequence length is variable for one or more of the first competitor oligonucleotides, second competitor oligonucleotides, third competitor oligonucleotides and fourth competitor oligonucleotides. At times, the stuffer sequence is from a non-human genome. Sometimes the stuffer sequence is from the PhiX 174 genome. In some embodiments, the competitor oligonucleotide is about 100 to about 150 base pairs long. In some cases, the competitor oligonucleotide is about 115 to about 120 base pairs long. In some cases, the first and second competitor oligonucleotide is about 115 base pairs long. In some cases, the third competitor oligonucleotide is about 118 base pairs long. In some cases, the fourth competitor oligonucleotide is about 120 base pairs long. In some embodiments, the one or more first competitor oligonucleotides each comprise independently SEQ ID NO:21 and SEQ ID NO:22. In some embodiments, the one or more second competitor oligonucleotides each comprise independently SEQ ID NO:23 and SEQ ID NO:24. In some embodiments, the third competitor oligonucleotide comprises SEQ ID NO:26. In some embodiments, the one or more fourth competitor oligonucleotides each comprise independently SEQ ID NO:27 and SEQ ID NO:28. In some embodiments, the one or more competitor oligonucleotides comprise a detectable label. In some cases, the detectable label is a fluorophore and sometimes the fluorophore is different for each competitor oligonucleotide. In some embodiments, a predetermined copy number of each competitor oligonucleotide is used. In some cases, the amount of the fetal nucleic acid determined is the copy number of the fetal nucleic acid based on the amount of competitor oligonucleotide used. In some cases, the copy number of the majority nucleic acid species is determined.

In some embodiments, the sample nucleic acid is extracellular nucleic acid. In some cases, the nucleic acid sample is obtained from a pregnant female subject. In some cases, the subject is human. In some embodiments, the sample nucleic acid is from plasma. In some cases, the sample nucleic acid is from serum.

In some embodiments, the amplification is in a single reaction vessel. Sometimes two or more of the amplification products are different lengths. Often, the amplification is by polymerase chain reaction (PCR). In some embodiments, the method further comprises contacting the amplification products with an exonuclease prior to (b). In some cases, the separation of amplification products is based on length. Often, the separation is performed using electrophoresis. In some cases, the electrophoresis is capillary electrophoresis. In some embodiments, the method further comprises determining whether the nucleic acid sample is utilized for a sequencing reaction. In some cases, the sequencing reaction is a reversible terminator-based sequencing reaction. In some embodiments, the method further comprises determining whether sequencing information obtained for a nucleic acid sample is used for a diagnostic determination.

Also provided in some embodiments is a composition comprising a mixture of two or more amplified target nucleic acids distinguishable by length, where each amplicon comprises a first sequence identical to a target nucleic acid and one or more second sequences of variable length that are not identical to a target nucleic acid, where the target nucleic acids each comprise independently (a) a first region comprising a feature that (i) is present in a minority nucleic acid species and is not present in a majority nucleic acid species, or (ii) is not present in the minority nucleic acid species and is present in the majority nucleic acid species, and (b) a second region allowing for a determination of total nucleic acid in the sample, where the first and second regions are different.

In some embodiments, the first region and the second region are differentially methylated. In some cases, the target nucleic acid further comprises a third region allowing for a determination of the presence or absence of Y chromosome nucleic acid. In some cases, the target nucleic acid further comprises a fourth region allowing for a determination of the amount of digested or undigested nucleic acid, as an indicator of digestion efficiency.

In some embodiments, the target nucleic acid comprises one or more independent genomic DNA target sequences. In some cases, the genomic DNA target sequences are the same length. In some cases, the genomic DNA target sequences each comprise independently SEQ ID NOs:29 to 32 and SEQ ID NOs:34 to 36. Sometimes the target nucleic acid further comprises one or more independent competitor oligonucleotides. In some cases, the one or more competitor oligonucleotides comprise a stuffer sequence. In some cases, the competitor oligonucleotides each comprise independently SEQ ID NOs:21 to 24 and SEQ ID NOs:26 to 28.

Also provided in some embodiments is a kit for determining the amount of a minority nucleic acid species in a sample which contains a minority species and a majority species, the combination of the minority species and the majority species comprising total nucleic acid in the sample, comprising: (a) a first set of amplification primers that specifically amplify a first region comprising a feature that (1) is present in the minority nucleic acid species and is not present in the majority nucleic acid species, or (2) is not present in the minority nucleic acid species and is present in the majority nucleic acid species, (b) a second set of amplification primers that amplify a second region allowing for a determination of total nucleic acid in the sample, where the first region and the second region are different, and (c) one or more inhibitory oligonucleotides that reduce the amplification of the second region. In some embodiments, the kit further comprises a third set of amplification primers that amplify a third region allowing for a determination of the presence or absence of Y chromosome nucleic acid. In some embodiments, the kit further comprises a fourth set of amplification primers that amplify a fourth region allowing for a determination of the amount of digested or undigested nucleic acid, as an indicator of digestion efficiency. In some embodiments, the kit further comprises one or more first competitor oligonucleotides that compete with the first region for hybridization of primers of the first amplification primer set. In some embodiments, the kit further comprises one or more second competitor oligonucleotides that compete with the second region for hybridization of primers of the second amplification primer set. In some embodiments, the kit further comprises one or more third competitor oligonucleotides that compete with the third region for hybridization of primers of the third amplification primer set. In some embodiments, the kit further comprises one or more fourth competitor oligonucleotides that compete with the fourth region for hybridization of primers of the fourth amplification primer set. In some embodiments, the kit further comprises one or more methylation sensitive restriction enzymes.

In some embodiments, the kit further comprises instructions or a location for carrying out a method for determining the amount of a minority nucleic acid species in a sample which contains a minority species and a majority species, the combination of the minority species and the majority species comprising total nucleic acid in the sample, comprising (a) contacting under amplification conditions a nucleic acid sample comprising a minority nucleic acid species with (i) a first set of amplification primers that specifically amplify a first region comprising a feature that (1) is present in the minority nucleic acid species and is not present in the majority nucleic acid species, or (2) is not present in the minority nucleic acid species and is present in the majority nucleic acid species, (ii) a second set of amplification primers that amplify a second region allowing for a determination of total nucleic acid in the sample, where the first region and the second region are different, and (iii) one or more inhibitory oligonucleotides that reduce the amplification of the second region, thereby generating minority and total nucleic acid amplification products, where the total nucleic acid amplification products are reduced relative to total amplification products that would be generated if no inhibitory oligonucleotide was present, (b) separating the amplification products, thereby generating separated minority and total nucleic acid amplification products, and (c) determining the fraction of the minority nucleic acid species in the sample relative to the total amount of the nucleic acid in the sample based on the amount of each of the separated minority and total nucleic acid amplification products.

In some embodiments, the inhibitory oligonucleotide comprises one or more 3' mismatched nucleotides.

In some embodiments, the method further comprises contacting under amplification conditions the nucleic acid with third set of amplification primers that amplify a third region allowing for a determination of the presence or absence of Y chromosome nucleic acid. In some embodiments, the method further comprises contacting under amplification conditions the nucleic acid with a fourth set of amplification primers that amplify a fourth region allowing for a determination of the amount of digested or undigested nucleic acid, as an indicator of digestion efficiency. In some embodiments, the method further comprises contacting under amplification conditions the nucleic acid with one or more first competitor oligonucleotides that compete with the first region for hybridization of primers of the first amplification primer set. In some embodiments, the method further comprises contacting under amplification conditions the nucleic acid with one or more second competitor oligonucleotides that compete with the second region for hybridization of primers of the second amplification primer set. In some embodiments, the method further comprises contacting under amplification conditions the nucleic acid with one or more third competitor oligonucleotides that compete with the third region for hybridization of primers of the third amplification primer set. In some embodiments, the method further comprises contacting under amplification conditions the nucleic acid with one or more fourth competitor oligonucleotides that compete with the fourth region for hybridization of primers of the fourth amplification primer set.

In some embodiments, a predetermined copy number of each competitor oligonucleotide is used. In some cases, the amount of the minority nucleic acid determined is the copy number of the minority nucleic acid species based on the amount of competitor oligonucleotide used. In some embodiments, the minority nucleic acid species is fetal DNA and the majority nucleic acid species is maternal DNA. In some embodiments, the first region is methylated and the second region is unmethylated.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 3A and FIG. 3B illustrate an example targeted inhibitory PCR scheme. To reduce endogenous levels of the genomic DNA target sequences for total DNA, a specific ratio of inhibitory oligonucleotides are included. These inhibitory oligonucleotides reduce the efficiency of the total DNA PCR and can be titrated so that the products reach the level of the genomic DNA target sequences for methylation. FIG. 3A illustrates a PCR assay where no inhibitory oligonucleotides are used. FIG. 3B illustrates a PCR assay where inhibitory oligonucleotides are used to reduce the signal for total DNA in the electropherogram.

FIG. 4A and FIG. 4B illustrate a comparison between two assays used for fetal DNA quantification. In FIG. 4A, the DNA quantification assay provided herein is made up of three distinct steps and allows for high throughput by a single operator. The entire procedure can be performed within 5 hours and the entire procedure including DNA extraction can be performed in a single day. Reaction mixtures are typically added in volumes greater than 10 microliters, which minimizes technical and sampling variability. The only apparatuses needed are a thermocycler and an automated electophoresis instrument. As shown in FIG. 4B, the other DNA quantification assay is made up of eight steps, six of which occur post PCR, and include a proteinase K step (ProtK), shrimp alkaline phosphatase step (SAP), single base extension step (TYPEPLEX), water and resin step (W & R), dispensing onto chip step (D), and mass spectrophotometry (MASSARRAY). This assay includes a MALDI-TOF based approach for quantification which requires special instrumentation as well as highly skilled operators able to diagnose problems occurring during any step of the post PCR procedure. Due to the many steps involved the complete reaction in FIG. 4B cannot be performed on a single day.

In FIG. 5A, female placental DNA was used. In FIG. 5B, male placental DNA was used. The arrowhead in FIG. 5B points to a peak generated by a 93 bp amplification product which corresponds to Y chromosome DNA. This peak is absent in FIG. 5A (female placental DNA).

In FIG. 7A, a ratio of 0.4 micromolar inhibitor/0.6 micromolar PCR primer was used. In FIG. 7B, a ratio of 0.6 micromolar inhibitor/0.4 micromolar PCR primer was used. While the intensity of the total markers was severely reduced with increased addition of inhibitors, no change was seen in the unaffected assays targeting methylation and Chromosome Y markers.

FIG. 9A presents a strip chart showing the calculated placental copy numbers using either the methylation or chromosome Y specific markers. FIG. 9B presents a strip chart showing the calculated total copy numbers. Each dilution contained a constant total number of genomes. FIG. 9C shows a correlation between methylation markers and chromosome Y. The copy numbers of placental DNA spiked into maternal non-methylated DNA in varying amounts was calculated by using the ratios obtained from the methylation assays and the Y-chromosome markers compared to the respective competitors. The model system showed high correlation between the methylation-based quantification and chromosome Y-specific sequences (rho=0.93 (Pearson correlation)). FIG. 9D shows a Q-Q plot comparing the calculated placental copy numbers using the methylation or chromosome Y markers.

FIG. 13A shows assay results with no exonuclease treatment. The unspecific remaining PCR primers are circled. FIG. 13B shows assay results from a sample treated post PCR with Exonuclease I. The unspecific peaks were no longer present in the electropherogram indicating that the single stranded PCR primers were removed by the exonuclease treatment and no double stranded primer dimers were formed.

FIG. 14A and FIG. 14B present box plots showing the minority fraction based SOX14 and TBX3 methylation markers in mixed DNA samples containing 0 to 10% minority species. The boxes represent the fractions obtained from 8 replicates. The upper and lower whiskers represent the 5th and 95th percentiles. The upper, middle, and lower bars represent the 25th, 50th, 75th percentiles. FIG. 14A shows samples containing a total of 1500 copies per reaction. FIG. 14B shows samples containing a total of 3000 copies per reaction.

FIG. 15A and FIG. 15B present box plots showing calculated copy numbers from the minority fraction based on SOX14 and TBX3 methylation markers in mixed DNA samples containing 0 to 10% minority species. The boxes represent the fractions obtained from 8 replicates. The upper and lower whiskers represent the 5th and 95th percentiles. The upper, middle, and lower bars represent the 25th, 50th, 75th percentiles. FIG. 15A show samples containing a total of 1500 copies per reaction. FIG. 15B show samples containing a total of 3000 copies per reaction.

DETAILED DESCRIPTION

Figure 1:
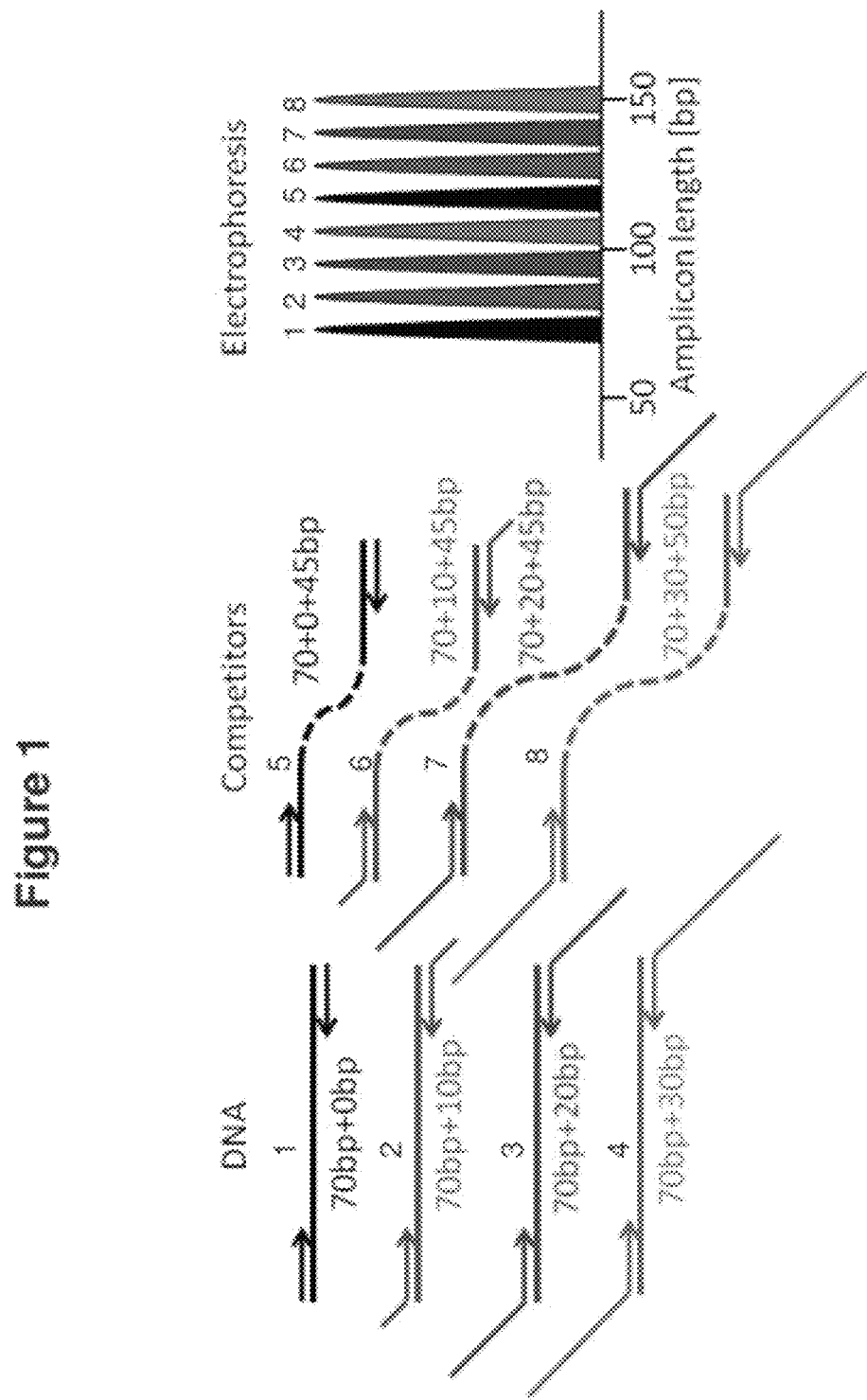
FIG. 1 illustrates an example amplification scheme for the genomic DNA target sequences and competitors. The multiplex assay includes four different genomic DNA target sequences (each for a particular region) and four corresponding competitors: Methylation (1 and 5), Total DNA (2 and 6), Chromosome Y (3 and 7) and Digestion control (4 and 8). Multiplex PCR is performed using marker specific tailed primers and competitors containing stuffer sequences. The PCR products are separated using electrophoresis.

Provided herein are methods for determining the amount of a minority nucleic acid species in a sample, methods for determining the amount of fetal nucleic acid in a sample, kits for carrying out such methods, and mixtures of amplified nucleic acids distinguishable by length generated by such methods. Quantification of a species of nucleic acid in a sample where a limited number of copies is present can be a challenge. In some cases, it is desirable to determine the exact copy number of a minority nucleic acid species. Often, nucleic acids are amplified and separated according to length to facilitate detection and quantification. Such techniques can be adapted to high-throughput screening methods. However, in cases where a minority nucleic acid is co-amplified with majority nucleic acid, the resulting analysis of amplification products can be dominated by the presence of the majority nucleic acid species. Under these circumstances, the analytical window is reduced and quantification of the minority nucleic acid is compromised. Accurate quantification and copy number determination of a minority nucleic acid species in a sample is carried out by an assay that can co-amplify nucleic acids present at relatively high and low starting concentrations. Such assays are provided by the compositions and methods described herein.

Nucleic Acids

Provided herein are methods for nucleic acid quantification. The terms "nucleic acid", "nucleic acid molecule" and "polynucleotide" may be used interchangeably throughout the disclosure. The terms refer to nucleic acids of any composition from, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome (e.g., a nucleic acid sample may be from one chromosome of a sample obtained from a diploid organism). The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil. A nucleic acid may be prepared using a nucleic acid obtained from a subject.

Extracellular Nucleic Acid

Nucleic acid can be extracellular nucleic acid in certain embodiments. The terms "extracellular nucleic acid" or "cell free nucleic acid" or "circulating cell free nucleic acid" as used herein refer to nucleic acid isolated from a source having substantially no cells (e.g., no detectable cells; may contain cellular elements or cellular remnants). Examples of acellular sources for extracellular nucleic acid are blood plasma, blood serum and urine. Without being limited by theory, extracellular nucleic acid may be a product of cell apoptosis (e.g. extracellular nucleic acid from post-apoptotic placental cells), cell necrosis and/or cell breakdown, which provides basis for extracellular nucleic acid often having a series of lengths across a large spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 1% to about 40% of the overall nucleic acid (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40% of the nucleic acid is fetal nucleic acid). In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less).

Cellular Nucleic Acid

Nucleic acid can be cellular nucleic acid in certain embodiments. The term "cellular nucleic acid" as used herein refers to nucleic acid isolated from a source having intact cells. Non-limiting examples of sources for cellular nucleic acid are blood cells, tissue cells, organ cells, tumor cells, hair cells, skin cells, and bone cells.

In some embodiments, nucleic acid is from peripheral blood mononuclear cells (PBMC). A PBMC is any blood cell having a round nucleus, such as, for example, lymphocytes, monocytes or macrophages. These cells can be extracted from whole blood, for example, using ficoll, a hydrophilic polysaccharide that separates layers of blood, with PBMCs forming a buffy coat under a layer of plasma. Additionally, PBMCs can be extracted from whole blood using a hypotonic lysis which will preferentially lyse red blood cells and leave PBMCs intact.

In some embodiments, nucleic acid is from placental cells. The placenta is an organ that connects the developing fetus to the uterine wall to allow nutrient uptake, waste elimination, and gas exchange via the mother's blood supply. The placenta develops from the same sperm and egg cells that form the fetus, and functions as a fetomaternal organ with two components, the fetal part (Chorion frondosum), and the maternal part (Decidua basalis). In some embodiments, nucleic acid is obtained from the fetal part of the placenta. In some embodiments, nucleic acid is obtained from the maternal part of the placenta.

Nucleic Acid Quantification

Provided herein are methods for nucleic acid quantification. In some embodiments, the amount of a minority nucleic acid species is determined relative to the amount of total nucleic acid. In some embodiments, the copy number for a minority nucleic acid species is determined.

Minority vs. Majority Species

As used herein, it is not intended that the terms "minority" or "majority" be rigidly defined in any respect. In one aspect, a nucleic acid that is considered "minority", for example, can have an abundance of at least about 0.1% of the total nucleic acid in a sample to less than 50% of the total nucleic acid in a sample. In some embodiments, a minority nucleic acid can have an abundance of at least about 1% of the total nucleic acid in a sample to about 40% of the total nucleic acid in a sample. In some embodiments, a minority nucleic acid can have an abundance of at least about 2% of the total nucleic acid in a sample to about 30% of the total nucleic acid in a sample. In some embodiments, a minority nucleic acid can have an abundance of at least about 3% of the total nucleic acid in a sample to about 25% of the total nucleic acid in a sample. For example, a minority nucleic acid can have an abundance of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% of the total nucleic acid in a sample. In some embodiments, the minority nucleic acid is extracellular DNA. In some embodiments, the minority nucleic acid is extracellular fetal DNA.

In another aspect, a nucleic acid that is considered "majority", for example, can have an abundance greater than 50% of the total nucleic acid in a sample to about 99.9% of the total nucleic acid in a sample. In some embodiments, a majority nucleic acid can have an abundance of at least about 60% of the total nucleic acid in a sample to about 99% of the total nucleic acid in a sample. In some embodiments, a majority nucleic acid can have an abundance of at least about 70% of the total nucleic acid in a sample to about 98% of the total nucleic acid in a sample. In some embodiments, a majority nucleic acid can have an abundance of at least about 75% of the total nucleic acid in a sample to about 97% of the total nucleic acid in a sample. For example, a majority nucleic acid can have an abundance of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the total nucleic acid in a sample. In some embodiments, the majority nucleic acid is extracellular DNA. In some embodiments, the majority nucleic acid is extracellular maternal DNA.

Competitor Oligonucleotides

In some embodiments of the methods provided herein, one or more competitor oligonucleotides are used to achieve quantification of a minority nucleic acid species. As used herein, a "competitor oligonucleotide" or "competitive oligonucleotide" or "competitor" is a nucleic acid polymer that competes with a target nucleotide sequence for hybridization of amplification primers. Often, the competitor has the same nucleotide sequence as the target nucleotide sequence. In some cases, the competitor optionally has an additional length of nucleotide sequence that is different from the target nucleotide sequence. Often, the additional length of nucleotide sequence is from a different genome than the target nucleotide sequence or is a synthetic sequence. In some embodiments, a known amount, or copy number, of competitor is used. In some embodiments, two or more competitors are used. In some cases, the two or more competitors possess similar characteristics (e.g. length, detectable label). In some cases, the two or more competitors possess different characteristics (e.g. length, detectable label). In some embodiments, one or more competitors are used for a particular region. In some cases, the competitor possesses a characteristic that is unique for each set of competitors for a given region. Often, competitors for different regions possess different characteristics.

A competitor oligonucleotide may be composed of naturally occurring and/or non-naturally occurring nucleotides (e.g., labeled nucleotides), or a mixture thereof. Competitor oligonucleotides suitable for use with embodiments described herein, may be synthesized and labeled using known techniques. Competitor oligonucleotides may be chemically synthesized according to any suitable method known, for example, the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of competitor oligonucleotides can be effected by any suitable method known, for example, native acrylamide gel electrophoresis or by anion-exchange high-performance liquid chromatography (HPLC), for example, as described in Pearson and Regnier, J. Chrom., 255:137-149, 1983.

Competitor Length

In some embodiments, multiple competitors are used within a multiplex amplification assay. In some cases, the competitors used for a particular region are the same length. In some embodiments, the competitors used for different regions are different lengths. Competitors can be, for example, at least about 30 base pairs in length to about 500 base pairs in length. In some embodiments, competitors can be at least about 50 base pairs in length to about 200 base pairs in length. In some embodiments, competitors can be at least about 100 base pairs in length to about 150 base pairs in length. In some embodiments, competitors can be at least about 115 base pairs in length to about 125 base pairs in length. For example, a competitor can be about 115, 116, 117, 118, 119, 120, 121, 122, 123, 124, or 125 base pairs in length. Non-limiting examples of competitor oligonucleotides that can be used with the methods provided herein are set forth in SEQ ID NOs:21-28.

In some embodiments, the competitor possesses a stuffer sequence. A stuffer sequence is a sequence of nucleotides that, in general, does not share any sequence similarity with the target nucleotide sequence. Often a stuffer is added to the competitor to distinguish, by length, the amplified products for the competitor from the amplified products for the target nucleotide sequence. Stuffer sequences can be included anywhere within the competitor oligonucleotide. In some embodiments, the stuffer sequence is included at one or more positions within the competitor oligonucleotide that are (i) downstream of the nucleotide sequence complementary to the forward primer and (ii) upstream of the nucleotide sequence complementary to the reverse primer. In some cases, the stuffer sequence is a contiguous sequence. In some cases, the stuffer sequence exists as two or more fragments within a competitor oligonucleotide. For the methods provided herein, the term "sequence length" when used in reference to a stuffer sequence means a contiguous length of nucleotide sequence or a sum of nucleotide sequence fragment lengths. In some embodiments, a stuffer sequence is from a genome that is different from the target genome. For example, if the target genome is human, then the stuffer sequence will often be selected from a non-human genome. For embodiments where the target nucleotide sequence is from the human genome, a competitor stuffer sequence can be from any non-human genome known in the art, such as, for example, non-mammalian animal genomes, plant genomes, fungal genomes, bacterial genomes, or viral genomes. In some embodiments, the stuffer sequence is from the PhiX 174 genome. In some embodiments, the stuffer sequence is not from genomic DNA and sometimes is synthetic.

In some embodiments, the competitor possesses a stuffer sequence whose length (or sum of fragment lengths) is unique, or constant, for each set of competitors for a given region. Often, competitors for different regions possess stuffer sequences of different, or variable, lengths (or sum of fragment lengths). As used herein, the term "constant length" refers to a length of a sequence of nucleotides that is the same for one or more nucleotide sequences, such as, for example, a stuffer sequence. As used herein, the term "variable length" refers to a length of a sequence of nucleotides that is different for one or more nucleotide sequences, such as, for example, a stuffer sequence. Competitor stuffer sequences can be of any length suitable for the methods provided herein. For example, competitor stuffer sequences can be at least about 1 base pair in length to about 100 base pairs in length. In some embodiments, the stuffer sequence is at least about 15 base pairs in length to about 55 base pairs in length. In some embodiments the stuffer sequence can be composed of several shorter stuffer sequences. This design can be utilized if the amplicon is prone to form secondary structures during PCR. For example, the stuffer sequence can be 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 base pairs in length. Examples of competitor design using single and multiple stuffer sequences are provided herein and shown in Table 3 of Example 1.

Amplified competitors can optionally be further distinguishable from one another through the use of tailed amplification primers containing additional non-hybridizing nucleotide sequences of varying length. These are described in further detail below.

Labeled Competitors

In some embodiments, the competitor oligonucleotide can be detected by detecting a detectable label, molecule or entity or "signal-generating moiety" (e.g., a fluorophore, radioisotope, colorimetric agent, particle, enzyme and the like). The term "signal-generating" as used herein refers to any atom or molecule that can provide a detectable or quantifiable effect, and that can be attached to a nucleic acid. In certain embodiments, a detectable label generates a unique light signal, a fluorescent signal, a luminescent signal, an electrical property, a chemical property, a magnetic property and the like.

In certain embodiments, the oligonucleotide can be modified to include a detectable label using any method known to one of skill in the art. The label may be incorporated as part of the synthesis, or added on prior to using the primer in any of the processes described herein. Incorporation of label may be performed either in liquid phase or on solid phase. In some embodiments the detectable label may be useful for detection of targets. In some embodiments the detectable label may be useful for the quantification target nucleic acids (e.g., determining copy number of a particular sequence or species of nucleic acid). Any detectable label suitable for detection of an interaction or biological activity in a system can be appropriately selected and utilized by the artisan. Examples of detectable labels are fluorescent labels or tags such as fluorescein, rhodamine, and others (e.g., Anantha, et al., Biochemistry (1998) 37:2709 2714; and Qu & Chaires, Methods Enzymol. (2000) 321:353 369); radioactive isotopes (e.g., 125I, 131I, 35S, 31P, 32P, 33P, 14C, 3H, 7Be, 28Mg, 57Co, 65Zn, 67Cu, 68Ge, 82Sr, 83Rb, 95Tc, 96Tc, 103Pd, 109Cd, and 127Xe); light scattering labels (e.g., U.S. Pat. No. 6,214,560, and commercially available from Genicon Sciences Corporation, CA); chemiluminescent labels and enzyme substrates (e.g., dioxetanes and acridinium esters), enzymic or protein labels (e.g., green fluorescence protein (GFP) or color variant thereof, luciferase, peroxidase); other chromogenic labels or dyes (e.g., cyanine), and other cofactors or biomolecules such as digoxigenin, streptavidin, biotin (e.g., members of a binding pair such as biotin and avidin for example), affinity capture moieties and the like. Additional detectable labels include, but are not limited to, nucleotides (labeled or unlabelled), compomers, sugars, peptides, proteins, antibodies, chemical compounds, conducting polymers, binding moieties such as biotin, mass tags, colorimetric agents, light emitting agents, radioactive tags, charge tags (electrical or magnetic charge), volatile tags and hydrophobic tags, biomolecules (e.g., members of a binding pair antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) and the like. In some embodiments a probe may contain a signal-generating moiety that hybridizes to a target and alters the passage of the target nucleic acid through a nanopore, and can generate a signal when released from the nucleic acid when it passes through the nanopore (e.g., alters the speed or time through a pore of known size). In some embodiments a primer may be labeled with an affinity capture moiety. Also included in detectable labels are those labels useful for mass modification for detection with mass spectrometry (e.g., matrix-assisted laser desorption ionization (MALDI) mass spectrometry and electrospray (ES) mass spectrometry).

In some embodiments, the detectable label is a fluorophore. A fluorophore is a functional group in a molecule which can absorb energy of a specific wavelength and re-emit energy at a different (but equally specific) wavelength. The amount and wavelength of the emitted energy depend on both the fluorophore and the chemical environment of the fluorophore. Any fluorophore known in the art can be used in conjunction with the methods provided herein and include, for example, fluorescein isothiocyanate (FITC), Xanthene derivatives (e.g. fluorescein, rhodamine (TRITC), Oregon green, eosin, Texas red, Cal Fluor), Cyanine derivatives (e.g. cyanine, indocarbocyanine, oxacarbocyanine, thiacarbocyanine, merocyanine, Quasar), Naphthalene derivatives (e.g. dansyl and prodan derivatives), Coumarin derivatives, oxadiazole derivatives (e.g. pyridyloxazole, nitrobenzoxadiazole, benzoxadiazole), Pyrene derivatives (e.g. cascade blue), Oxazine derivatives (e.g. Nile red, Nile blue, cresyl violet, oxazine 170), Acridine derivatives (e.g. proflavin, acridine orange, acridine yellow), Arylmethine derivatives (e.g. auramine, crystal violet, malachite green), Tetrapyrrole derivatives (e.g. porphin, phtalocyanine, bilirubin), CF DYE (Biotium), BODIPY (Invitrogen), ALEXA FLUOR (Invitrogen), DYLIGHT FLUOR (Thermo Scientific, Pierce), ATTO and TRACEY (Sigma Aldrich), FLUOPROBES (Interchim), and MEGASTOKES DYES (Dyomics). In some embodiments, the competitor possesses a fluorophore that is unique for each set of competitors for a given region. Often, competitors for different regions possess different fluorophores.

Features for Distinguishing a Minority Nucleic Acid from a Majority Nucleic Acid In some of the embodiments of the methods provided herein, a minority nucleic acid possesses a feature that is present in the minority nucleic acid and is not present in the majority nucleic acid. In some of the embodiments of the methods provided herein, a minority nucleic acid possesses a feature that is not present in the minority nucleic acid and is present in the majority nucleic acid. The feature that is present or not present in the minority nucleic acid can be any feature that can distinguish the minority nucleic acid from the majority nucleic acid such as, for example, a sequence paralog or sequence variation (e.g. single nucleotide polymorphism (SNP), addition, insertion, deletion) or a particular epigenetic state. The term "epigenetic state" or "epigenetic status" as used herein refers to any structural feature at a molecular level of a nucleic acid (e.g., DNA or RNA) other than the primary nucleotide sequence. For instance, the epigenetic state of a genomic DNA may include its secondary or tertiary structure determined or influenced by, for example, its methylation pattern or its association with cellular or extracellular proteins.

Methylation

In some embodiments, a feature that distinguishes a minority nucleic acid from a majority nucleic acid is methylation state. The terms "methylation state", "methylation profile", or "methylation status," as used herein to describe the state of methylation of a genomic sequence, refer to the characteristics of a DNA segment at a particular genomic locus relevant to methylation. Such characteristics include, but are not limited to, whether any of the cytosine (C) residues within a DNA sequence are methylated, location of methylated C residue(s), percentage of methylated C at any particular stretch of residues, and allelic differences in methylation due to, e.g., difference in the origin of the alleles. The terms above also refer to the relative or absolute concentration of methylated C or unmethylated C at any particular stretch of residues in a biological sample. For example, if the cytosine (C) residue(s) within a DNA sequence are methylated it can be referred to as "hypermethylated"; whereas if the cytosine (C) residue(s) within a DNA sequence are not methylated it may be referred to as "hypomethylated". Likewise, if the cytosine (C) residue(s) within a DNA sequence (e.g., fetal nucleic acid) are methylated as compared to another sequence from a different region or from a different individual (e.g., relative to maternal nucleic acid), that sequence is considered hypermethylated compared to the other sequence. Alternatively, if the cytosine (C) residue(s) within a DNA sequence are not methylated as compared to another sequence from a different region or from a different individual (e.g., the mother), that sequence is considered hypomethylated compared to the other sequence. These sequences are said to be "differentially methylated", and more specifically, when the methylation status differs between mother and fetus, the sequences are considered "differentially methylated maternal and fetal nucleic acid". Methods and examples of differentially methylated sites in fetal nucleic acid are described in, for example, PCT Publication No. WO2010/033639.

As used herein, a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring, however, for purposes herein, thymine is not considered a methylated nucleotide when present in DNA since thymine is a typical nucleotide base of DNA. Typical nucleoside bases for DNA are thymine, adenine, cytosine and guanine. Typical bases for RNA are uracil, adenine, cytosine and guanine. Correspondingly a "methylation site" is the location in the target gene nucleic acid region where methylation has, or has the possibility of occurring. For example a location containing CpG is a methylation site where the cytosine may or may not be methylated. Such methylation sites can be susceptible to methylation either by natural occurring events in vivo or by an event instituted to chemically methylate the nucleotide in vitro.

A "nucleic acid comprising one or more CpG sites" or a "CpG-containing genomic sequence" as used herein refers to a segment of DNA sequence at a defined location in the genome of an individual such as a human fetus or a pregnant woman. Typically, a "CpG-containing genomic sequence" is at least 15 nucleotides in length and contains at least one cytosine. Often, it can be at least 30, 50, 80, 100, 150, 200, 250, or 300 nucleotides in length and contains at least 2, 5, 10, 15, 20, 25, or 30 cytosines. For any one "CpG-containing genomic sequence" at a given location, e.g., within a region centering on a given genetic locus, nucleotide sequence variations may exist from individual to individual and from allele to allele even for the same individual. Typically, such a region centering on a defined genetic locus (e.g., a CpG island) contains the locus as well as upstream and/or downstream sequences. Each of the upstream or downstream sequence (counting from the 5' or 3' boundary of the genetic locus, respectively) can be as long as 10 kb, in other cases may be as long as 5 kb, 2 kb, 1 kb, 500 bp, 200 bp, or 100 bp. Furthermore, a "CpG-containing genomic sequence" may encompass a nucleotide sequence transcribed or not transcribed for protein production, and the nucleotide sequence can be an inter-gene sequence, intra-gene sequence, protein-coding sequence, a non protein-coding sequence (such as a transcription promoter), or a combination thereof. A "CpG island" as used herein describes a segment of DNA sequence that possesses a functionally or structurally deviated CpG density. A CpG island can typically be, for example, at least 400 nucleotides in length, have a greater than 50% GC content, and an OCF/ECF ratio greater than 0.6. In some cases a CpG island can be characterized as being at least 200 nucleotides in length, having a greater than 50% GC content, and an OCF/ECF ratio greater than 0.6.

In some embodiments, nucleic acid may be exposed to a process that modifies certain nucleotides in the nucleic acid before providing nucleic acid for a method described herein. A process that selectively modifies nucleic acid based upon the methylation state of nucleotides therein can be applied to a nucleic acid sample, for example. Methods for modifying a nucleic acid molecule in a manner that reflects the methylation pattern of the nucleic acid molecule are known in the art, as exemplified in U.S. Pat. No. 5,786,146 and U.S. patent publications 20030180779 and 20030082600. For example, non-methylated cytosine nucleotides in a nucleic acid can be converted to uracil by bisulfite treatment, which does not modify methylated cytosine.

Nucleic Acid Cleavage

In some embodiments of the methods provided herein, the nucleic acid is exposed to one or more cleavage agents. The term "cleavage agent" as used herein refers to an agent, sometimes a chemical or an enzyme that can cleave a nucleic acid at one or more specific or non-specific sites. Specific cleavage agents often cleave specifically according to a particular nucleotide sequence at a particular site. In some cases, the nucleic acid is exposed to one or more cleavage agents prior to amplification. In some cases, the nucleic acid is exposed to one or more cleavage agents following amplification. In some cases, the nucleic acid is exposed to one or more cleavage agents prior to amplification and following amplification.

Examples of enzymatic cleavage agents include without limitation endonucleases (e.g., DNase (e.g., DNase I, II); RNase (e.g., RNase E, F, H, P); CLEAVASE enzyme; TAQ DNA polymerase; E. coli DNA polymerase I and eukaryotic structure-specific endonucleases; murine FEN-1 endonucleases; type I, II or III restriction endonucleases (i.e. restriction enzymes) such as Acc I, AciI, Afl III, Alu I, Alw44 I, Apa I, Asn I, Ava I, Ava II, BamH I, Ban II, Bcl I, Bgl I. Bgl II, Bln I, Bsm I, BssH II, BstE II, BstUI, Cfo I, Cla I, Dde I, Dpn I, Dra I, EcIX I, EcoR I, EcoR I, EcoR II, EcoR V, Hae II, Hae II, HhaI, Hind III, Hind III, Hpa I, Hpa II, Kpn I, Ksp I, MaeII, McrBC, Mlu I, MIuN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I; glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease I, exonuclease II, exonuclease III, exonuclease IV, exonuclease V, exonuclease VI, exonuclease VII, exonuclease VIII); ribozymes, and DNAzymes.

Methylation-Sensitive Restriction Enzyme Digestion

In some embodiments of the methods provided herein, the nucleic acid is treated with one or more methylation-sensitive restriction enzymes. As used herein, "methylation sensitive restriction enzymes" or "methyl-sensitive enzymes" are restriction enzymes that preferentially or substantially cleave or digest at their DNA recognition sequence if it is non-methylated. Thus, an unmethylated DNA sample treated with a methylation-sensitive restriction enzyme will be digested into smaller fragments, whereas a methylated or hypermethylated DNA sample would remain substantially undigested. Conversely, there are examples of methyl-sensitive enzymes that cleave at their DNA recognition sequence only if it is methylated. Examples of enzymes that digest only methylated DNA include, but are not limited to, DpnI, which cuts at a recognition sequence GATC, and McrBC, which cuts DNA containing modified cytosines (New England BioLabs®, Inc, Beverly, Mass.).

Methyl-sensitive enzymes that digest unmethylated DNA suitable for use in the methods provided herein include, but are not limited to, HpaII, HhaI, MaeII, BstUI and AciI. In some embodiments, combinations of two or more methyl-sensitive enzymes that digest only unmethylated DNA can be used. In some embodiments, HpaII, which cuts only the unmethylated sequence CCGG, is used. In some embodiments, HhaI, which cuts only the unmethylated sequence GCGC, is used. Both enzymes are available from New England BioLabs®, Inc (Beverly, Mass.).

Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al., Molecular Biology: A laboratory Approach, Cold Spring Harbor, N.Y. 1989) provide a general description of methods for using restriction enzymes and other enzymes. Enzymes often are used under conditions that will enable cleavage of the DNA with about 95%-100% efficiency, preferably with about 98%-100% efficiency.

Exonuclease Treatment

In some embodiments of the methods provided herein, the nucleic acid is treated with an exonuclease. Exonucleases are enzymes that work by cleaving nucleotides one at a time from the end of a polynucleotide chain through a hydrolyzing reaction that breaks phosphodiester bonds at either the 3' or the 5' end. Any exonuclease known in the art can be used with the methods provided herein and include, for example, 5' to 3' exonucleases (e.g. exonuclease II), 3' to 5' exonucleases (e.g. exonuclease I), and poly(A)-specific 3' to 5' exonucleases. In some embodiments, the nucleic acid is optionally treated with an exonuclease to remove any contaminating nucleic acids such as, for example, single stranded PCR primers. Typically, this step is performed after completion of nucleic acid amplification. In some embodiments, a single strand specific exonuclease is used. In some embodiments, exonuclease I is used.

Genomic DNA Target Sequences

In some embodiments of the methods provided herein, one or more nucleic acid species, and sometimes one or more nucleotide sequence species, are targeted for amplification and quantification. In some embodiments, the targeted nucleic acids are genomic DNA sequences. Certain genomic DNA target sequences are used, for example, because they can allow for the determination of a particular feature for a given assay. Genomic DNA target sequences can be referred to herein as markers for a given assay. In some embodiments, more than one genomic DNA target sequence or marker can allow for the determination of a particular feature for a given assay. Such genomic DNA target sequences are considered to be of a particular "region". As used herein, a "region" is not intended to be limited to a description of a genomic location, such as a particular chromosome, stretch of chromosomal DNA or genetic locus. Rather, the term "region" is used herein to identify a collection of one or more genomic DNA target sequences or markers that can be indicative of a particular assay. Such assays can include, but are not limited to, assays for the detection and quantification of a minority nucleic acid species, assays for the detection and quantification of a majority nucleic acid, assays for the detection and quantification of total DNA, assays for the detection and quantification of methylated DNA, assays for the detection and quantification of fetal specific nucleic acid (e.g. chromosome Y DNA), and assays for the detection and quantification of digested and/or undigested DNA, as an indicator of digestion efficiency. In some embodiments, the genomic DNA target sequence is described as being within a particular genomic locus. As used herein, a genomic locus can include any or a combination of open reading frame DNA, non-transcribed DNA, intronic sequences, extronic sequences, promoter sequences, enhancer sequences, flanking sequences, or any sequences considered by one of skill in the art to be associated with a given genomic locus.

Assays for the Determination of Methylated DNA

In some embodiments of the methods provided herein, one or more genomic DNA target sequences are used that can allow for the determination of methylated DNA. Generally, genomic DNA target sequences used for the determination of methylated DNA are differentially methylated in the minority and majority species, and thus, differentially digested according to the methods provided herein for methylation-sensitive restriction enzymes. In some cases, the genomic DNA target sequence is a single copy gene. In some cases, the genomic DNA target sequence is not located on chromosome 13. In some cases, the genomic DNA target sequence is not located on chromosome 18. In some cases, the genomic DNA target sequence is not located on chromosome 21. In some cases, the genomic DNA target sequence is not located on chromosome X. In some cases, the genomic DNA target sequence is not located on chromosome Y. In some cases, the genomic DNA target sequence is typically methylated in one DNA species such as, for example, placental DNA (i.e. at least about 50% or greater methylation). In some cases, the genomic DNA target sequence is minimally methylated in another DNA species such as, for example, maternal DNA (i.e. less than about 1% methylation). In some cases, the genomic DNA target sequence does not contain any known single nucleotide polymorphisms (SNPs) within the PCR primer hybridization sequences. In some cases, the genomic DNA target sequence does not contain any known mutations within the PCR primer hybridization sequences. In some cases, the genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some cases, the genomic DNA target sequence contains at least two restriction sites within the amplified region. In some cases, the restriction site sequence is GCGC. In some cases, the restriction site sequence is CCGG. In some cases, the genomic DNA target sequence contains a combination of the restriction site sequences GCGC and CCGG within the amplified region. In some embodiments, the genomic DNA target sequence length is about 50 base pairs to about 200 base pairs. In some cases, the genomic DNA target sequence length is 70 base pairs. In some cases, the genomic DNA target sequence does not possess any negative ΔG values for secondary structure of the complete amplicon prediction using mfold (M. Zuker, Mfold web server for nucleic acid folding and hybridization prediction. *Nucleic Acids Res.* 31 (13), 3406-15, (2003)). In some embodiments, the genomic DNA target sequence used for the determination of methylated DNA is within the TBX3 locus. An example of a TBX3 genomic target sequence is set forth in SEQ ID NO:29. In some embodiments, the genomic DNA target sequence used for the determination of methylated DNA is within the SOX14 locus. An example of a SOX14 genomic target is set forth in SEQ ID NO:30. Additional genomic targets that can be used for the determination of methylated DNA in conjunction with the methods provided herein are presented in Table 14 and Table 15 in Example 10.

Assays for the Determination of Total DNA

In some embodiments of the methods provided herein, one or more genomic DNA target sequences are used that can allow for the determination of total DNA. Generally, genomic DNA target sequences used for the determination of total DNA are present in every genome copy (e.g. is present in fetal DNA and maternal DNA, cancer DNA and normal DNA, pathogen DNA and host DNA). In some cases, the genomic DNA target sequence is a single copy gene. In some cases, the genomic DNA target sequence is not located on chromosome 13. In some cases, the genomic DNA target sequence is not located on chromosome 18. In some cases, the genomic DNA target sequence is not located on chromosome 21. In some cases, the genomic DNA target sequence is not located on chromosome X. In some cases, the genomic DNA target sequence is not located on chromosome Y. In some cases, the genomic DNA target sequence does not contain any known single nucleotide polymorphisms (SNPs) within the PCR primer hybridization sequences. In some cases, the genomic DNA target sequence does not contain any known mutations within the PCR primer hybridization sequences. In some cases, the genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some cases, the genomic DNA target sequence does not contain the restriction site GCGC within the amplified region. In some cases, the genomic DNA target sequence does not contain the restriction site CCGG within the amplified region. In some embodiments, the genomic DNA target sequence length is about 50 base pairs to about 200 base pairs. In some cases, the genomic DNA target sequence length is 70 base pairs. In some cases, the genomic DNA target sequence does not possess any negative ΔG values for secondary structure of the complete amplicon prediction using mfold (M. Zuker, Mfold web server for nucleic acid folding and hybridization prediction. *Nucleic Acids Res.* 31 (13), 3406-15, (2003)). In some embodiments, the genomic DNA target sequence used for the determination of total DNA is within the POP5 locus. An example of a POP5 genomic target sequence is set forth in SEQ ID NO:31. In some embodiments, the genomic DNA target sequence used for the determination of total DNA is within the APOE locus. An example of an APOE genomic target is set forth in SEQ ID NO:32.

Assays for the Determination of Fetal DNA

In some embodiments of the methods provided herein, one or more genomic DNA target sequences are used that can allow for the determination of fetal DNA. In some embodiments, genomic DNA target sequences used for the determination of fetal DNA are specific to the Y chromosome. In some cases, the genomic DNA target sequence is a single copy gene. In some cases, the genomic DNA target sequence does not contain any known single nucleotide polymorphisms (SNPs) within the PCR primer hybridization sequences. In some cases, the genomic DNA target sequence does not contain any known mutations within the PCR primer hybridization sequences. In some cases, the genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some cases, the genomic DNA target sequence does not contain the restriction site GCGC within the amplified region. In some cases, the genomic DNA target sequence does not contain the restriction site CCGG within the amplified region. In some embodiments, the genomic DNA target sequence length is about 50 base pairs to about 200 base pairs. In some cases, the genomic DNA target sequence length is 70 base pairs. In some cases, the genomic DNA target sequence does not possess any negative ΔG values for secondary structure of the complete amplicon prediction using mfold (M. Zuker, Mfold web server for nucleic acid folding and hybridization prediction. *Nucleic Acids Res.* 31 (13), 3406-15, (2003)). In some embodiments, the genomic DNA target sequence used for the determination of fetal DNA is within the UTY locus. An example of a UTY genomic target sequence is set forth in SEQ ID NO:33. In some embodiments, the genomic DNA target sequence used for the determination of fetal DNA is within the DDX3Y locus. An example of a DDX3Y genomic target is set forth in SEQ ID NO:34.

Assays for the Determination of Digested and/or Undigested DNA

In some embodiments of the methods provided herein, one or more genomic DNA target sequences are used that can allow for the determination of the amount of digested or undigested nucleic acid, as an indicator of digestion efficiency. Such genomic DNA target sequences are present in every genome in the sample (e.g. majority and minority species genomes). Generally, genomic DNA target sequences used for the determination of digested or undigested DNA contain at least one restriction site present in a genomic DNA target sequence used in another assay. Thus, the genomic DNA target sequences used for the determination of digested or undigested DNA serve as controls for assays that include differential digestion. Generally, the genomic DNA target sequence is unmethylated in all nucleic acid species tested (e.g. unmethylated in both majority and minority species genomes). In some cases, the genomic DNA target sequence contains at least one restriction site GCGC within the amplified region. In some cases, the genomic DNA target sequence contains at least one restriction site CCGG within the amplified region. In some cases, the genomic DNA target sequence contains exactly one restriction site GCGC within the amplified region and exactly one restriction site CCGG within the amplified region. In some cases, the genomic DNA target sequence is a single copy gene. In some cases, the genomic DNA target sequence is not located on chromosome 13. In some cases, the genomic DNA target sequence is not located on chromosome 18. In some cases, the genomic DNA target sequence is not located on chromosome 21. In some cases, the genomic DNA target sequence is not located on chromosome X. In some cases, the genomic DNA target sequence is not located on chromosome Y. In some cases, the genomic DNA target sequence does not contain any known single nucleotide polymorphisms (SNPs) within the PCR primer hybridization sequences. In some cases, the genomic DNA target sequence does not contain any known mutations within the PCR primer hybridization sequences. In some cases, the genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some embodiments, the genomic DNA target sequence length is about 50 base pairs to about 200 base pairs. In some cases, the genomic DNA target sequence length is 70 base pairs. In some cases, the genomic DNA target sequence does not possess any negative ΔG values for secondary structure of the complete amplicon prediction using mfold (M. Zuker, Mfold web server for nucleic acid folding and hybridization prediction. *Nucleic Acids Res.* 31 (13), 3406-15, (2003)). In some embodiments, the genomic DNA target sequence used for the determination of digested or undigested DNA is within the POP5 locus. An example of a POP5 genomic target sequence is set forth in SEQ ID NO:35. In some embodiments, the genomic DNA target sequence used for the determination of digested or undigested DNA is within the LDHA locus. An example of an LDHA genomic target is set forth in SEQ ID NO:36.

Amplification

In some embodiments of the methods provided herein, nucleic acid species are amplified using a suitable amplification process. It can be desirable to amplify nucleotide sequence species particularly if one or more of the nucleic acid species exist at low copy number. An amplification product (amplicon) of a particular nucleic acid species is referred to herein as an "amplified nucleic acid species." Nucleic acid amplification typically involves enzymatic synthesis of nucleic acid amplicons (copies), which contain a sequence complementary to a nucleotide sequence species being amplified. Amplifying a nucleic acid species and detecting the amplicons synthesized can improve the sensitivity of an assay, since fewer target sequences are needed at the beginning of the assay, and can facilitate detection and quantification of a nucleic acid species.

The terms "amplify", "amplification", "amplification reaction", or "amplifying" refer to any in vitro processes for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step. In some embodiments a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions, for example, and also may reduce amplification biases due to nucleotide sequence or species abundance of the target. In some embodiments a one-time primer extension may be used may be performed as a prelude to linear or exponential amplification.

Any suitable amplification technique can be utilized. Amplification of polynucleotides include, but are not limited to, polymerase chain reaction (PCR); ligation amplification (or ligase chain reaction (LCR)); amplification methods based on the use of Q-beta replicase or template-dependent polymerase (see US Patent Publication Number US20050287592); helicase-dependant isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, combinations thereof, and the like. Reagents and hardware for conducting PCR are commercially available.

A generalized description of an amplification process is presented herein. Primers and target nucleic acid are contacted, and complementary sequences anneal to one another, for example. Primers can anneal to a target nucleic acid, at or near (e.g., adjacent to, abutting, and the like) a sequence of interest. The terms "near" or "adjacent to" when referring to a nucleotide sequence of interest refers to a distance or region between the end of the primer and the nucleotide or nucleotides of interest. As used herein adjacent is in the range of about 5 nucleotides to about 500 nucleotides (e.g., about 5 nucleotides away from nucleotide of interest, about 10, about 20, about 30, about 40, about 50, about 60, about 70, about 80, about 90, about 100, about 150, about 200, about 250, about 300, abut 350, about 400, about 450 or about 500 nucleotides from a nucleotide of interest). In some embodiments, the primers in a set hybridize within about 10 to 30 nucleotides from a nucleic acid sequence of interest and produce amplified products. In some embodiments, the primers hybridize within the nucleic acid sequence of interest.

A reaction mixture, containing components necessary for enzymatic functionality, is added to the primer-target nucleic acid hybrid, and amplification can occur under suitable conditions. Components of an amplification reaction may include, but are not limited to, e.g., primers (e.g., individual primers, primer pairs, primer sets and the like) a polynucleotide template (e.g., target nucleic acid), polymerase, nucleotides, dNTPs and the like. In some embodiments, non-naturally occurring nucleotides or nucleotide analogs, such as analogs containing a detectable label (e.g., fluorescent or colorimetric label), may be used for example. Polymerases can be selected by a person of ordinary skill and include polymerases for thermocycle amplification (e.g., Taq DNA Polymerase; Q-Bio™ Taq DNA Polymerase (recombinant truncated form of Taq DNA Polymerase lacking 5'-3' exo activity); SurePrime™ Polymerase (chemically modified Taq DNA polymerase for "hot start" PCR); Arrow™ Taq DNA Polymerase (high sensitivity and long template amplification)) and polymerases for thermostable amplification (e.g., RNA polymerase for transcription-mediated amplification (TMA) described at World Wide Web URL "gen-probe.com/pdfs/tma_whiteppr.pdf"). Other enzyme components can be added, such as reverse transcriptase for transcription mediated amplification (TMA) reactions, for example.

PCR conditions can be dependent upon primer sequences, target abundance, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. Digital PCR is also known to those of skill in the art; see, e.g., US Patent Application Publication Number 20070202525, filed Feb. 2, 2007, which is hereby incorporated by reference). PCR is typically carried out as an automated process with a thermostable enzyme. In this process, the temperature of the reaction mixture is cycled through a denaturing step, a primer-annealing step, and an extension reaction step automatically. Some PCR protocols also include an activation step and a final extension step. Machines specifically adapted for this purpose are commercially available. A non-limiting example of a PCR protocol that may be suitable for embodiments described herein is, treating the sample at 95° C. for 5 minutes; repeating thirty-five cycles of 95° C. for 45 seconds and 68° C. for 30 seconds; and then treating the sample at 72° C. for 3 minutes. A completed PCR reaction can optionally be kept at 4° C. until further action is desired. Multiple cycles frequently are performed using a commercially available thermal cycler. Suitable isothermal amplification processes known and selected by the person of ordinary skill in the art also may be applied, in certain embodiments.

In some embodiments, an amplification product may include naturally occurring nucleotides, non-naturally occurring nucleotides, nucleotide analogs and the like and combinations of the foregoing. An amplification product often has a nucleotide sequence that is identical to or substantially identical to a sample nucleic acid nucleotide sequence or complement thereof. A "substantially identical" nucleotide sequence in an amplification product will generally have a high degree of sequence identity to the nucleotide sequence species being amplified or complement thereof (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity), and variations sometimes are a result of infidelity of the polymerase used for extension and/or amplification, or additional nucleotide sequence(s) added to the primers used for amplification.

In certain embodiments, nucleic acid amplification can generate additional nucleic acid species of different or substantially similar nucleic acid sequence. In certain embodiments described herein, contaminating or additional nucleic acid species, such as, for example, the competitor oligonucleotides provided herein, which may contain sequences substantially complementary to, or may be substantially identical to, the sequence of interest, can be useful for sequence quantification, with the proviso that the level of contaminating or additional sequences remains constant and therefore can be a reliable marker whose level can be substantially reproduced. Additional considerations that may affect sequence amplification reproducibility are; PCR conditions (number of cycles, volume of reactions, melting temperature difference between primers pairs, and the like), concentration of target nucleic acid in sample (e.g. fetal nucleic acid in maternal nucleic acid background, viral nucleic acid in host background), the number of chromosomes on which the nucleotide species of interest resides (e.g., paralogous sequence), variations in quality of prepared sample, and the like. The terms "substantially reproduced" or "substantially reproducible" as used herein refer to a result (e.g., quantifiable amount of nucleic acid) that under substantially similar conditions would occur in substantially the same way about 75% of the time or greater, about 80%, about 85%, about 90%, about 95%, or about 99% of the time or greater.

Each amplified nucleic acid species generally is amplified under conditions that amplify that species at a substantially reproducible level. In this case, the term "substantially reproducible level" as used herein refers to consistency of amplification levels for a particular amplified nucleic acid species per unit nucleic acid (e.g., per unit nucleic acid that contains the particular nucleotide sequence species amplified). A substantially reproducible level varies by about 1% or less in certain embodiments, after factoring the amount of nucleic acid giving rise to a particular amplification nucleic acid species (e.g., normalized for the amount of nucleic acid). In some embodiments, a substantially reproducible level varies by 10%, 5%, 4%, 3%, 2%, 1.5%, 1%, 0.5%, 0.1%, 0.05%, 0.01%, 0.005% or 0.001% after factoring the amount of nucleic acid giving rise to a particular amplification nucleic acid species. Alternatively, substantially reproducible means that any two or more measurements of an amplification level are within a particular coefficient of variation ("CV") from a given mean. Such CV may be 20% or less, sometimes 10% or less and at times 5% or less. The two or more measurements of an amplification level may be determined between two or more reactions and/or two or more of the same sample types.

In some embodiments where a target nucleic acid is RNA, prior to the amplification step, a DNA copy (cDNA) of the RNA transcript of interest may be synthesized. A cDNA can be synthesized by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in Diagnostic Molecular Biology: Principles and Applications pp. 401-406; Persing et al., eds., Mayo Foundation, Rochester, Minn., 1993; Egger et al., J. Clin. Microbiol. 33:1442-1447, 1995; and U.S. Pat. No. 5,075,212. Branched-DNA technology may be used to amplify the signal of RNA markers in certain samples, such as maternal blood. For a review of branched-DNA (bDNA) signal amplification for direct quantification of nucleic acid sequences in clinical samples, see Nolte, Adv. Clin. Chem. 33:201-235, 1998.

Amplification also can be accomplished using digital PCR, in certain embodiments (see e.g. Kalinina et al., "Nanoliter scale PCR with TaqMan detection." Nucleic Acids Research. 25; 1999-2004, (1997); Vogelstein and Kinzler (Digital PCR. Proc Natl Acad Sci USA. 96; 9236-41, (1999); PCT Patent Publication No. WO05023091A2; US Patent Publication No. US 20070202525). Digital PCR takes advantage of nucleic acid (DNA, cDNA or RNA) amplification on a single molecule level, and offers a highly sensitive method for quantifying low copy number nucleic acid. Systems for digital amplification and analysis of nucleic acids are available (e.g., Fluidigm® Corporation).

Primers

Primers useful for detection, amplification, quantification, sequencing and analysis of nucleic acid are provided. The term "primer" as used herein refers to a nucleic acid that includes a nucleotide sequence capable of hybridizing or annealing to a target nucleic acid, at or near (e.g., adjacent to) a specific region of interest. Primers can allow for specific determination of a target nucleic acid nucleotide sequence or detection of the target nucleic acid (e.g., presence or absence of a sequence or copy number of a sequence), or feature thereof, for example. A primer may be naturally occurring or synthetic. The term "specific" or "specificity", as used herein, refers to the binding or hybridization of one molecule to another molecule, such as a primer for a target polynucleotide. That is, "specific" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules. The terms "primer", "oligo", or "oligonucleotide" may be used interchangeably throughout the document, when referring to primers.

A primer nucleic acid can be designed and synthesized using suitable processes, and may be of any length suitable for hybridizing to a nucleotide sequence of interest (e.g., where the nucleic acid is in liquid phase or bound to a solid support) and performing analysis processes described herein. Primers may be designed based upon a target nucleotide sequence. A primer in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides (e.g., labeled nucleotides), or a mixture thereof. Primers suitable for use with embodiments described herein, may be synthesized and labeled using known techniques. Primers may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of primers can be effected by native acrylamide gel electrophoresis or by anion-exchange high-performance liquid chromatography (HPLC), for example, as described in Pearson and Regnier, J. Chrom., 255:137-149, 1983.

All or a portion of a primer nucleic acid sequence (naturally occurring or synthetic) may be substantially complementary to a target nucleic acid, in some embodiments. As referred to herein, "substantially complementary" with respect to sequences refers to nucleotide sequences that will hybridize with each other. The stringency of the hybridization conditions can be altered to tolerate varying amounts of sequence mismatch. Included are target and primer sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Primers that are substantially complimentary to a target nucleic acid sequence are also substantially identical to the compliment of the target nucleic acid sequence. That is, primers are substantially identical to the anti-sense strand of the nucleic acid. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

Primer sequences and length may affect hybridization to target nucleic acid sequences. Depending on the degree of mismatch between the primer and target nucleic acid, low, medium or high stringency conditions may be used to effect primer/target annealing. As used herein, the term "stringent conditions" refers to conditions for hybridization and washing. Methods for hybridization reaction temperature condition optimization are known to those of skill in the art, and may be found in Current Protocols in Molecular Biology, John Wiley & Sons, N.Y., 6.3.1-6.3.6 (1989). Aqueous and non-aqueous methods are described in that reference and either can be used. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile. Features of primers can be applied to probes and oligonucleotides, such as, for example, the competitive and inhibitory oligonucleotides provided herein.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target nucleic acid sequence that is complementary to the primer.

In some embodiments primers can include a nucleotide subsequence that may be complementary to a solid phase nucleic acid primer hybridization sequence or substantially complementary to a solid phase nucleic acid primer hybridization sequence (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% identical to the primer hybridization sequence complement when aligned). A primer may contain a nucleotide subsequence not complementary to or not substantially complementary to a solid phase nucleic acid primer hybridization sequence (e.g., at the 3' or 5' end of the nucleotide subsequence in the primer complementary to or substantially complementary to the solid phase primer hybridization sequence).

A primer, in certain embodiments, may contain a modification such as one or more inosines, abasic sites, locked nucleic acids, minor groove binders, duplex stabilizers (e.g., acridine, spermidine), Tm modifiers or any modifier that changes the binding properties of the primers or probes. A primer, in certain embodiments, may contain a detectable molecule or entity (e.g., a fluorophore, radioisotope, colorimetric agent, particle, enzyme and the like, as described above for labeled competitor oligonucleotides).

A primer also may refer to a polynucleotide sequence that hybridizes to a subsequence of a target nucleic acid or another primer and facilitates the detection of a primer, a target nucleic acid or both, as with molecular beacons, for example. The term "molecular beacon" as used herein refers to detectable molecule, where the detectable property of the molecule is detectable only under certain specific conditions, thereby enabling it to function as a specific and informative signal. Non-limiting examples of detectable properties are, optical properties, electrical properties, magnetic properties, chemical properties and time or speed through an opening of known size.

In some embodiments, the primers are complementary to genomic DNA target sequences. In some cases, the forward and reverse primers hybridize to the 5' and 3' ends of the genomic DNA target sequences. In some embodiments, primers that hybridize to the genomic DNA target sequences also hybridize to competitor oligonucleotides that were designed to compete with corresponding genomic DNA target sequences for binding of the primers. In some cases, the primers hybridize or anneal to the genomic DNA target sequences and the corresponding competitor oligonucleotides with the same or similar hybridization efficiencies. In some cases the hybridization efficiencies are different. The ratio between genomic DNA target amplicons and competitor amplicons can be measured during the reaction. For example if the ratio is 1:1 at 28 cycles but 2:1 at 35, this could indicate that during the end of the amplification reaction the primers for one target (i.e. genomic DNA target or competitor) are either reannealing faster than the other, or the denaturation is less effective than the other.

In some embodiments primers are used in sets. As used herein, an amplification primer set is one or more pairs of forward and reverse primers for a given region. Thus, for example, primers that amplify genomic targets for region 1 (i.e. targets 1a and 1b) are considered a primer set. Primers that amplify genomic targets for region 2 (i.e. targets 2a and 2b) are considered a different primer set. In some embodiments, the primer sets that amplify targets within a particular region also amplify the corresponding competitor oligonucleotide(s). A plurality of primer pairs may constitute a primer set in certain embodiments (e.g., about 2, 3, 4, 5, 6, 7, 8, 9, 10, 15, 20, 25, 30, 35, 40, 45, 50, 55, 60, 65, 70, 75, 80, 85, 90, 95 or 100 pairs). In some embodiments a plurality of primer sets, each set comprising pair(s) of primers, may be used.

Tailed Primers

In some embodiments, the primers are composed of a hybridization sequence (i.e. nucleotides that hybridize or anneal to a target) and a non-hybridizing sequence (i.e. nucleotides that do not hybridize or anneal to a target). In some embodiments, the non-hybridizing sequence is located at the 5' end of the primer. Primers that contain a 5' non-hybridizing sequence are referred to herein as "tailed primers" or "primers with 5' tails". 5' tails can possess any of the features described herein for primers and can be any length. For example, 5' tails can be about 1 to about 100 nucleotides in length. In some embodiments, a 5' tail can be about 3 to about 20 nucleotides in length. For example, a 5' tail can be 1, 2, 3, 4, 5, 6, 7, 8, 9, 10, 11, 12, 13, 14, 15, 16, 17, 18, 19, or 20 nucleotides in length. In some embodiments, the forward and reverse primers of a primer pair each contain a 5' tail of the same length. In some embodiments, the forward and reverse primers of a primer pair each contain a 5' tail that is a different length. In some embodiments, only the forward or the reverse primer contains a 5' tail. In some embodiments, one or more primers do not contain a 5' tail. In some embodiments one or more primers have a 5' tail and one or more primers do not have a 5' tail.

In some embodiments of the methods provided herein, pairs of forward and reverse primers can each contain a 5' tail of varying length. Such primers can add a specific length to a given amplification product. As used herein, "overall added length" refers to the combined length of the forward primer 5' tail and the reverse primer 5' tail for a given primer pair. In some embodiments, primers that amplify a genomic DNA target sequence and a corresponding competitor oligonucleotide each contain a 5' tail of the same overall added length (see e.g. FIG. 1). In some embodiments, where more than one genomic DNA target sequence is amplified for a particular region, the primers that amplify the genomic DNA target sequences and corresponding competitor oligonucleotides each contain a 5' tail of the same overall added length. For example, if genomic target 1a and genomic target 1b are in the same region, primers that amplify genomic targets 1a and 1b (and the corresponding competitor oligonucleotides) will each contain a 5' tail of the same overall added length (see e.g. FIG. 2). In some embodiments, where more than one genomic DNA target sequence is amplified for a particular region and more than one region is assayed, the primers that amplify the genomic DNA target sequences and competitor oligonucleotides within a region each contain a 5' tail of the same overall added length and among regions each contain a 5' tail of different overall added lengths. For example, if genomic target 1a and genomic target 1b are in region 1 and genomic target 2a and genomic target 2b are in region 2, primers that amplify genomic targets (and the corresponding competitor oligonucleotides) in region 1 will each contain a 5' tail of a given overall added length that is different from the 5' tail overall added length for primers in region 2 (see e.g. FIG. 2). Examples of primers that can be used with the methods provided herein are set forth in SEQ ID NOs:1-16.

Inhibitory PCR

In some embodiments of the methods provided herein, inhibitory PCR is performed. In some cases, enrichment of a minority nucleic acid species in a polynucleotide sample is desired. Often, this enrichment involves selectively reducing the amplification of a majority nucleic acid species. This approach provides advantages over simply increasing the amount of starting material used in an amplification reaction. First, this approach eliminates the potential for non-specific cross hybridization of abundant messages to the primers. Second, it results in an increase of the relative abundance of the moderate and low abundance messages. This means, for example, that for a given amount of material used in an amplification reaction or other application, each of the remaining sequences (e.g. a minority nucleic acid species) is present in a higher proportion and will therefore be more easily detected, quantified and/or isolated. Third, it allows for quantitative analysis of the amplification products by a separation-based method, such as, for example, electrophoresis, by generating different amplification products in amounts that are more proportional.

These methods combine the polymerization and/or amplification of desired species (i.e., a minority nucleic acid species) and the suppression or reduction of polymerization and/or amplification of non-desired species (i.e., at least one majority nucleic acid species) in a single reaction, and thus simplifies the enrichment process. By combining these steps into a single step, loss and/or degradation of sample, especially low abundance or rare species in a sample, is minimized. The methods provided herein often may not require large amounts of starting material, and thus, find particular use in the analysis of samples where the amount of starting material is limited. The methods provided herein can be applied to any situation where a low-abundance polynucleotide is in a sample of polynucleotides, where more abundant polynucleotides prevent or hinder the detection or isolation of the low-abundance species. This sequence-specific suppression or reduction of high-abundance species, and consequent enrichment of low-abundance species, permits the detection, isolation and/or analysis of the low-abundance polynucleotides that were previously too low in concentration to be readily detected or isolated prior to the enrichment.

The methods described herein provide, in some embodiments, for the enrichment of one or more minority nucleic acid species in a sample. These methods enrich a sample for a minority nucleic acid species by exposing the polynucleotides in a sample to conditions for enzymatic polymerization, and simultaneously suppressing the polymerization of at least one majority nucleic species in the sample. The inhibition of polymerization of at least one majority nucleic acid species results in the relative enrichment of other less abundant species (i.e. a minority nucleic acid) in the sample. The methods provided herein, in some embodiments, utilize sequence-specific non-extendable oligonucleotides, for example, that can preferentially block the polymerization of at least one majority nucleic acid species in a pool of nucleic acid, and thus, increase the relative proportion of one or more minority nucleic acid species. In some embodiments, the minority nucleic acid species is fetal nucleic acid and the majority nucleic acid is maternal nucleic acid. In some embodiments, the minority nucleic acid species is nucleic acid from cancer cells and the majority nucleic acid is nucleic acid from normal cells. In some embodiments, the minority nucleic acid species is nucleic acid from a pathogen (e.g. virus, bacteria, fungus) and the majority nucleic acid is host nucleic acid.

Methods for the enrichment of a minority nucleic acid species in a sample, include, for example, inhibitory PCR methods. Such methods can involve the use of, for example, one or more inhibitory primers, in some embodiments. As used herein, the terms "inhibitory oligonucleotide", "inhibitor", "inhibitory primer", "non-extendable oligonucleotide", or "blocking/blocked primer" refer to oligonucleotides designed to reduce the amplification of a nucleic acid species. As used herein, the term "reduce" or "reduction" when used in reference to amplification means to generate an amount of amplification product that is less than an amount of amplification product generated by a reaction where no inhibitor is used. A reduction in amplification can be to any degree, such as for example, about 1% reduction to about 100% reduction. For example, the reduction in amplification can be about 1%, 5%, 10%, 20%, 30%, 40%, 50%, 60%, 70%, 80%, 90%, 95%, or 100%.

In some embodiments, one or more inhibitory oligonucleotides are added to the sample prior to initiating a polymerase amplification reaction. The inhibitory oligonucleotides anneal to their target sequence and create a duplex that selectively suppresses the amplification of the target polynucleotide by blocking the progression or initiation of a polymerase enzyme (i.e. primer extension). Inhibitory oligonucleotides can be designed and produced according to methods known in the art and/or methods for primer design and production provided herein. Inhibitory oligonucleotides can possess any of the features described herein for primers and can be any length. In some embodiments, an inhibitory oligonucleotide contains a sequence that hybridizes to a particular nucleic acid species. In some cases the inhibitory oligonucleotide can hybridize to a particular genomic DNA target sequence. In some cases the inhibitory oligonucleotide can hybridize to a particular competitor oligonucleotide. Often the same inhibitory oligonucleotide can hybridize to both a genomic DNA target sequence and its corresponding competitor oligonucleotide. It is not intended that the site of duplex formation between the inhibitory oligonucleotide and target nucleic acid be particularly limited. In some embodiments, a site of duplex formation is more proximal to the site of polymerase initiation. In some embodiments, a site of duplex formation is more distal from the site of polymerase initiation. In some cases, the site of duplex formation overlaps or encompasses the polymerase start site.

In some embodiments, the amount of inhibitory oligonucleotide used is determined based on the degree of amplification reduction desired for a particular nucleic acid target. For example, a small reduction in amplification would require fewer copies of an inhibitory oligonucleotide than a large reduction in amplification. Amplification of a particular nucleic acid target can be reduced by at least about 1% to about 100%. For example, amplification of a particular nucleic acid target, such as, for example, a marker for total nucleic acid, can be reduced by about 1%, 5%, 10%, 20%, 30%, 40%, 50%, 60%, 70%, 80%, 90%, 95%, or 100%. The amount of inhibitor used in an amplification assay can be determined as follows. For each amplicon, a predetermined amount of amplification primers is used, such as, for example, 0.2 micromoles PCR primers per reaction. For amplicons where inhibitors are used the total concentration (PCR primer+inhibitor) remains the same (e.g. 0.2 micromoles) but the ratio of each pair is varied. To find a suitable ratio of PCR primer/inhibitor a DNA model system is generated which can include, for example, 90% major species and 10% minor species. Several parallel reactions can be performed where the ratio of PCR primer/inhibitor is varied, such as, for example, 9/1, 8/2, 7/3, 6/4, 5/5, 4/6, etc primer/inhibitor. The ratio where the minority species amplicons generate a product of similar degree of amplification as the majority species is an optimal ratio.

In some embodiments, an inhibitory oligonucleotide pair is used. An inhibitory oligonucleotide pair includes a forward and a reverse inhibitory oligonucleotide. As used herein, a forward inhibitory oligonucleotide is an inhibitory oligonucleotide that can inhibit nucleotide extension of the sense strand of a nucleic acid. As used herein, a reverse inhibitory primer is an inhibitory oligonucleotide that can inhibit nucleotide extension of the antisense strand of a nucleic acid. In some embodiments, a forward inhibitory oligonucleotide is used. In some embodiments, a reverse inhibitory oligonucleotide is used. In some embodiments inhibitory oligonucleotides are used in sets. As used herein, an inhibitory oligonucleotide set is one or more pairs of forward and reverse inhibitory oligonucleotides for a given region. Thus, for example, inhibitory oligonucleotides that inhibit amplification of genomic targets for region 1 (i.e. targets 1a and 1b) are considered an inhibitory oligonucleotide set. Primers that inhibit amplification of genomic targets for region 2 (i.e. targets 2a and 2b) are considered a different inhibitory oligonucleotide set. In some embodiments, the inhibitory oligonucleotide sets that inhibit amplification of targets within a particular region can also inhibit amplification of the corresponding competitor oligonucleotide(s). A plurality of inhibitory oligonucleotide pairs may constitute a inhibitory oligonucleotide set in certain embodiments (e.g., about 2, 3, 4, 5, 6, 7, 8, 9, 10, 15, 20, 25, 30, 35, 40, 45, 50, 55, 60, 65, 70, 75, 80, 85, 90, 95 or 100 pairs). In some embodiments a plurality of inhibitory oligonucleotide sets, each set comprising pair(s) of inhibitory oligonucleotides, may be used.

Inhibitory oligonucleotides can inhibit the amplification of a nucleic acid species through mechanisms known in the art for inhibitory oligonucleotides and through mechanisms provided herein. It is not intended that the chemical structure of the inhibitory oligonucleotide be particularly limited, except where the inhibitory oligonucleotide retains the ability to hybridize to a complementary target in a sequence-specific manner. Any type of inhibitory oligonucleotides can be used in the methods provided herein and include, but are not limited to, any oligonucleotide that: (i) is lacking a hydroxyl group on the 3' position of the ribose sugar in the 3' terminal nucleotide; (ii) has a modification to a sugar, nucleobase, or internucleotide linkage at or near the 3' terminal nucleotide that blocks polymerase activity, e.g., 2'-O-methyl; (iii) does not utilize a ribose sugar phosphodiester backbone in their oligomeric structure (e.g. peptide nucleic acids (PNAs)); and/or (iv) possesses one or more mismatched nucleotides at the 3' end. Examples of inhibitory oligonucleotides include, but are not limited to, locked nucleic acids (LNAs; see, WO 98/22489; WO 98/39352; and WO 99/14226), 2'-O-alkyl oligonucleotides (e.g., 2'-O-methyl modified oligonucleotides; see Majlessi et al., Nucleic Acids Research, 26(9):2224-2229 [1998]), 3' modified oligodeoxyribonucleotides, N3'-P5' phosphoramidate (NP) oligomers, MGB-oligonucleotides (minor groove binder-linked oligos), phosphorothioate (PS) oligomers, C1-C4 alkylphosphonate oligomers (e.g., methyl phosphonate (MP) oligomers), phosphoramidates, beta-phosphodiester oligonucleotides, and alpha-phosphodiester oligonucleotides, and 3' mismatched oligonucleotides.

In some cases, inhibitory oligonucleotides can be formed by using terminator nucleotides. Terminator nucleotides are nucleotides that are capable of being enzymatically incorporated onto a 3' terminus of a polynucleotide through the action of a polymerase enzyme, but cannot be further extended. Thus, a terminator nucleotide can be enzymatically incorporated, but is not enzymatically extendable. Examples of terminator nucleotides include 2,3-dideoxyribonucleotides (ddNTP), 2'-deoxy, 3'-fluoro nucleotide 5'-triphosphates, and labeled forms thereof.

In some embodiments, one or more inhibitory oligonucleotides can be used in amplification assays in combination with competitor oligonucleotides, such as, for example, the competitor oligonucleotides provided herein. In some embodiments, one or more inhibitory oligonucleotides are used in amplification assays where competitor oligonucleotides are not included. In some embodiments, amplifications assays include competitor oligonucleotides and do not include inhibitory oligonucleotides.

In some embodiments, one or more inhibitory oligonucleotides are used that contain one or more mismatched nucleotides at the 3' end. Such mismatched nucleotides do not hybridize to the target nucleic acid sequence, and thus, prevent nucleotide extension initiation and/or progression. An inhibitory oligonucleotide can contain any number of mismatched nucleotides at the 3' end. In some embodiments, an inhibitory oligonucleotide can have about 1 to about 20 mismatched nucleotides. For example, an inhibitory oligonucleotide can have 1, 2, 3, 4, 5, 6, 7, 8, 9, 10, 15, or mismatched nucleotides. Examples of inhibitory oligonucleotides that can be used with the methods provided herein are set forth in SEQ ID NOs:17-20.

Multiplex Amplification

In some embodiments, multiplex amplification processes may be used to amplify target nucleic acids, such that multiple amplicons are simultaneously amplified in a single, homogenous reaction. As used herein "multiplex amplification" refers to a variant of PCR where simultaneous amplification of multiple targets of interest in one reaction vessel may be accomplished by using more than one pair of primers (e.g., more than one primer set). In some embodiments multiplex amplification may be combined with another amplification (e.g., PCR) method (e.g., nested PCR or hot start PCR, for example) to increase amplification specificity and reproducibility. In certain embodiments multiplex amplification may be done in replicates, for example, to reduce the variance introduced by amplification. Design methods for multiplexed assays can include primer and oligonucleotide design methods and reaction design methods. For primer and oligonucleotide design in multiplexed assays, the same general guidelines for primer design applies for uniplexed reactions, such as avoiding false priming and primer dimers, although more primers are involved for multiplex reactions. In some embodiments, multiplex amplification can be useful for quantitative assays.

In some embodiments, one or more nucleic acid targets are amplified using a multiplex amplification process. In some embodiments, 10, 20, 50, 100, 200, 500, 1000 or more nucleic acid targets are amplified using a multiplex amplification process. In some embodiments, 2, 3, 4, 5, 6, 7, 8, 9, 10, 11, 12, 13, 14, 15, 16, 17, 18, 19, or 20 nucleic acid targets are amplified using a multiplex amplification process. In some cases, the nucleic acid target is one or more genomic DNA sequences. In some cases, the nucleic acid target is one or more oligonucleotides, such as, for example, the competitor oligonucleotides provided herein. In some embodiments, the genomic DNA sequences are coamplified with their corresponding competitor oligonucleotides. Often, the primer pairs used for amplification of a genomic DNA target sequence are the same for the amplification of the corresponding competitor oligonucleotide.

Amplicons

Each amplified nucleic acid species independently is about 10 to about 1000 base pairs in length in some embodiments. In certain embodiments, an amplified nucleic acid species is about 20 to about 500 base pairs in length. In certain embodiments, an amplified nucleic acid species is about 30 to about 250 base pairs in length, sometimes is about 50 to about 200 base pairs in length and sometimes is about 65 base pairs in length to about 160 base pairs in length. Thus, in some embodiments, the length of each of the amplified nucleic acid species products independently is about 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, or 160 base pairs (bp) in length.

In certain embodiments, one or more amplified nucleic acid species (i.e. amplicons) in an assay are of identical length, and sometimes the amplified nucleic acid species (i.e. amplicons) are of a different length. For example, one amplified nucleic acid species may be longer than one or more other amplified nucleic acid species by about 1 to about 100 nucleotides (e.g., about 2, 3, 4, 5, 6, 7, 8, 9, 10, 11, 12, 13, 14, 15, 16, 17, 18, 19, 20, 30, 40, 50, 60, 70, 80 or 90 nucleotides longer). In certain embodiments, the target DNA sequences are of identical length, and sometimes the target DNA sequences are of a different length. In some embodiments, where one or more genomic DNA target sequences are amplified for a particular region, the genomic DNA target sequence lengths can be the same and the amplicon lengths can be the same. In such cases, the amplicon may be the same length as the target or may be longer due to, for example, added length from tailed primers. For example, genomic DNA targets 1a and 1b are the same length and amplicons 1a and 1b are identical to each other in length, but not necessarily identical to the target length (i.e. if tailed primers were used for the amplification, for example). In such cases, amplicons of identical length will be detected as a single signal, such as, for example, a single electropherogram peak. In some embodiments, a single electropherogram peak can be the culmination of multiple independent amplified targets. For example, a single electropherogram peak can be generated by 1, 2, 3, 4, 5, 6, 7, 8, 9, 10 or more independent amplified targets. In some embodiments, where two or more genomic DNA target sequences are amplified for two or more different regions, the genomic DNA target sequence lengths can be the same and the amplicon lengths can be different. For example, genomic DNA targets 1a and 2a are for different regions and are the same length; and amplicons 1a and 2a are different lengths. In such cases, differential amplicon length may be achieved, for example, through the use of primers with 5' tails of different lengths. In such cases, amplicons of different lengths will be detected as multiple signals, such as, for example, two or more electropherogram peaks. Thus, in a multiplex amplification assay, such as a multiplex amplification assay provided herein, where a plurality of genomic DNA target sequences are amplified, the genomic target sequences can be all of the same length while the amplicon lengths can vary such that each amplicon length is indicative of one or more amplification products for a particular region.

In some embodiments of the methods provided herein, competitor oligonucleotides are co-amplified with genomic target DNA sequences. In certain embodiments, amplified competitor oligonucleotides (i.e. competitor amplicons) are of identical length, and sometimes the amplified competitor oligonucleotides (i.e. competitor amplicons) are of a different length. For example, one amplified competitor oligonucleotide may be longer than one or more other amplified competitor oligonucleotides by about 1 to about 100 nucleotides (e.g., about 2, 3, 4, 5, 6, 7, 8, 9, 10, 11, 12, 13, 14, 15, 16, 17, 18, 19, 20, 30, 40, 50, 60, 70, 80 or 90 nucleotides longer). In certain embodiments, the competitor oligonucleotides are of identical length, and sometimes the competitor oligonucleotides are of a different length. In some embodiments, where one or more competitor oligonucleotides are amplified that correspond to genomic DNA target sequence(s) for a particular region, the competitor oligonucleotide lengths can be the same and the competitor amplicon lengths can be the same. In such cases, the competitor amplicon may be the same length as the competitor oligonucleotides or may be longer due to, for example, added length from tailed primers. For example, competitor oligonucleotides Xa and Xb are the same length and competitor amplicons Xa and Xb are identical to each other in length, but not necessarily identical to the competitor oligonucleotide length (i.e. if tailed primers were used for the amplification, for example). In some embodiments, where two or more competitor oligonucleotides are amplified that correspond to genomic DNA target sequences for two or more different regions, the competitor oligonucleotide lengths can be the same or different and the competitor amplicon lengths can be different. For example, competitor oligonucleotides Xa, Ya and Za correspond to genomic DNA target sequences for different regions. Competitor oligonucleotides Xa and Ya are the same length and competitor Za is a different length; and competitor amplicons Xa, Ya and Za are each different lengths. In such cases, differential competitor amplicon length may be achieved, for example, through the use of primers with 5' tails of different lengths. Thus, in a multiplex amplification assay, such as a multiplex amplification assay provided herein, where a plurality of competitor oligonucleotides are amplified, the competitor oligonucleotides can be all of the same or different lengths while the competitor amplicon lengths can vary such that each competitor amplicon length is indicative of one or more competitor amplification products that correspond to genomic DNA targets for a particular region. In a multiplex amplification assay, for example, where a plurality of genomic DNA target sequences are co-amplified with a plurality of corresponding competitor oligonucleotides, the genomic DNA target sequences can all be of the same length, and the competitor oligonucleotides can be of the same or different lengths, such that the amplicons generated (through the use of tailed primers of varying length, for example) are distinct for each region assayed. In such cases, each region would be represented by two amplicon lengths (i.e. one amplicon length for the genomic DNA target(s) for that region and another amplicon length for the corresponding competitor oligonucleotide(s)).

Detection of Amplification Products

Nucleotide sequence species, or amplified nucleic acid species, or detectable products prepared from the foregoing, can be detected by a suitable detection process. Non-limiting examples of methods of detection, quantification, sequencing and the like include mass detection of mass modified amplicons (e.g., matrix-assisted laser desorption ionization (MALDI) mass spectrometry and electrospray (ES) mass spectrometry), a primer extension method (e.g., iPLEX™; Sequenom, Inc.), direct DNA sequencing, Molecular Inversion Probe (MIP) technology from Affymetrix, restriction fragment length polymorphism (RFLP analysis), allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader assay, hybridization using at least one probe, hybridization using at least one fluorescently labeled probe, cloning and sequencing, electrophoresis, the use of hybridization probes and quantitative real time polymerase chain reaction (QRT-PCR), digital PCR, nanopore sequencing, chips and combinations thereof. The detection and quantification of alleles or paralogs can be carried out using the "closed-tube" methods described in U.S. patent application Ser. No. 11/950,395, which was filed Dec. 4, 2007. In some embodiments the amount of each amplified nucleic acid species is determined by mass spectrometry, primer extension, sequencing (e.g., any suitable method, for example nanopore or pyrosequencing), Quantitative PCR (Q-PCR or QRT-PCR), digital PCR, combinations thereof, and the like.

Electrophoresis

In some embodiments of the methods provided herein, amplified nucleic acid sequences can be detected using electrophoresis. Any electrophoresis method known in the art, whereby amplified nucleic acids are separated by size, can be used in conjunction with the methods provided herein, which include, but are not limited to, standard electrophoretic techniques and specialized electrophoretic techniques, such as, for example capillary electrophoresis. Examples of methods for detection and quantification of target nucleic acid sequences using standard electrophoretic techniques can be found in the art. A non-limiting example is presented herein. After running an amplified nucleic acid sample in an agarose or polyacrylamide gel, the gel may be labeled (e.g., stained) with ethidium bromide (see, Sambrook and Russell, Molecular Cloning: A Laboratory Manual 3d ed., 2001). The presence of a band of the same size as the standard control is an indication of the presence of a target nucleic acid sequence, the amount of which may then be compared to the control based on the intensity of the band, thus detecting and quantifying the target sequence of interest. In certain embodiments, competitor oligonucleotides described herein can be used to detect the presence of the target sequence of interest. The competitor oligonucleotides can also be used to indicate the amount of the target nucleic acid molecules in comparison to the standard control, based on the intensity of signal imparted by the competitor oligonucleotides.

In some embodiments, capillary electrophoresis is used to separate and quantify amplified nucleic acids. Capillary electrophoresis (CE) encompasses a family of related separation techniques that use narrow-bore fused-silica capillaries to separate a complex array of large and small molecules, such as, for example, nucleic acids of varying length. High electric field strengths can be used to separate nucleic acid molecules based on differences in charge, size and hydrophobicity. Sample introduction is accomplished by immersing the end of the capillary into a sample vial and applying pressure, vacuum or voltage. Depending on the types of capillary and electrolytes used, the technology of CE can be segmented into several separation techniques, any of which can be adapted to the methods provided herein. Examples of these are provided below.

Capillary Zone Electrophoresis (CZE), also known as free-solution CE (FSCE), is the simplest form of CE. The separation mechanism is based on differences in the charge-to-mass ratio of the analytes. Fundamental to CZE are homogeneity of the buffer solution and constant field strength throughout the length of the capillary. The separation relies principally on the pH controlled dissociation of acidic groups on the solute or the protonation of basic functions on the solute. Capillary Gel Electrophoresis (CGE) is the adaptation of traditional gel electrophoresis into the capillary using polymers in solution to create a molecular sieve also known as replaceable physical gel. This allows analytes having similar charge-to-mass ratios to be resolved by size. This technique is commonly employed in SDS-Gel molecular weight analysis of proteins and the sizing of applications of DNA sequencing and genotyping.

Capillary Isoelectric Focusing (CIEF) allows amphoteric molecules, such as proteins, to be separated by electrophoresis in a pH gradient generated between the cathode and anode. A solute will migrate to a point where its net charge is zero. At the solutes isoelectric point (pI), migration stops and the sample is focused into a tight zone. In CIEF, once a solute has focused at its pI, the zone is mobilized past the detector by either pressure or chemical means. This technique is commonly employed in protein characterization as a mechanism to determine a protein's isoelectric point.

Isotachophoresis (ITP) is a focusing technique based on the migration of the sample components between leading and terminating electrolytes. Solutes having mobilities intermediate to those of the leading and terminating electrolytes stack into sharp, focused zones.

Electrokinetic Chromatography (EKC) is a family of electrophoresis techniques named after electrokinetic phenomena, which include electroosmosis, electrophoresis and chromatography. A key example of this is seen with cyclodextrin-mediated EKC. Here the differential interaction of enantiomers with the cyclodextrins allows for the separation of chiral compounds.

Micellar Electrokinetic Capillary Chromatography (MECC OR MEKC) is a mode of electrokinetic chromatography in which surfactants are added to the buffer solution at concentrations that form micelles. The separation principle of MEKC is based on a differential partition between the micelle and the solvent. This principle can be employed with charged or neutral solutes and may involve stationary or mobile micelles. MEKC has great utility in separating mixtures that contain both ionic and neutral species.

Micro Emulsion Electrokinetic Chromatography (MEEKC) is a CE technique in which solutes partition with moving oil droplets in buffer. The microemulsion droplets are usually formed by sonicating immicible heptane or octane with water. SDS is added at relatively high concentrations to stabilize the emulsion. This allows the separation of both aqueous and water-insoluble compounds.

Non-Aqueous Capillary Electrophoresis (NACE) involves the separation of analytes in a medium composed of organic solvents. The viscosity and dielectric constants of organic solvents affect both sample ion mobility and the level of electroosmotic flow. The use of non-aqueous medium allows additional selectivity options in methods development and is also valuable for the separation of water-insoluble compounds.

Capillary Electrochromatography (CEC) is a hybrid separation method that couples the high separation efficiency of CZE with HPLC and uses an electric field rather than hydraulic pressure to propel the mobile phase through a packed bed. Because there is minimal backpressure, it is possible to use small-diameter packings and achieve very high efficiencies. Its most useful application appears to be in the form of on-line analyte concentration that can be used to concentrate a given sample prior to separation by CZE.

Any device, instrument or machine capable of performing capillary electrophoresis can be used in conjunction with the methods provided herein. In general, a capillary electrophoresis system's main components are a sample vial, source and destination vials, a capillary, electrodes, a high-voltage power supply, a detector, and a data output and handling device. The source vial, destination vial and capillary are filled with an electrolyte such as an aqueous buffer solution. To introduce the sample, the capillary inlet is placed into a vial containing the sample and then returned to the source vial (sample is introduced into the capillary via capillary action, pressure, or siphoning). The migration of the analytes (i.e. nucleic acids) is then initiated by an electric field that is applied between the source and destination vials and is supplied to the electrodes by the high-voltage power supply. Ions, positive or negative, are pulled through the capillary in the same direction by electroosmotic flow. The analytes (i.e. nucleic acids) separate as they migrate due to their electrophoretic mobility and are detected near the outlet end of the capillary. The output of the detector is sent to a data output and handling device such as an integrator or computer. The data is then displayed as an electropherogram, which can report detector response as a function of time. Separated nucleic acids can appear as peaks with different migration times in an electropherogram.

Separation by capillary electrophoresis can be detected by several detection devices. The majority of commercial systems use UV or UV-Vis absorbance as their primary mode of detection. In these systems, a section of the capillary itself is used as the detection cell. The use of on-tube detection enables detection of separated analytes with no loss of resolution. In general, capillaries used in capillary electrophoresis can be coated with a polymer for increased stability. The portion of the capillary used for UV detection is often optically transparent. The path length of the detection cell in capillary electrophoresis (~50 micrometers) is far less than that of a traditional UV cell (~1 cm). According to the Beer-Lambert law, the sensitivity of the detector is proportional to the path length of the cell. To improve the sensitivity, the path length can be increased, though this can result in a loss of resolution. The capillary tube itself can be expanded at the detection point, creating a "bubble cell" with a longer path length or additional tubing can be added at the detection point. Both of these methods, however, may decrease the resolution of the separation.

Fluorescence detection can also be used in capillary electrophoresis for samples that naturally fluoresce or are chemically modified to contain fluorescent tags, such as, for example, labeled nucleic acids provided herein. This mode of detection offers high sensitivity and improved selectivity for these samples. The method requires that the light beam be focused on the capillary. Laser-induced fluorescence can be been used in CE systems with detection limits as low as 10-18 to 10-21 mol. The sensitivity of the technique is attributed to the high intensity of the incident light and the ability to accurately focus the light on the capillary.

Several capillary electrophoresis machines are known in the art and can be used in conjunction with the methods provided herein. These include, but are not limited to, CALIPER LAB CHIP GX (Caliper Life Sciences, Mountain View, Calif.), P/ACE 2000 Series (Beckman Coulter, Brea, Calif.), HP G1600A CE (Hewlett-Packard, Palo Alto, Calif.), AGILENT 7100 CE (Agilent Technologies, Santa Clara, Calif.), and ABI PRISM Genetic Analyzer (Applied Biosystems, Carlsbad, Calif.).

Nucleic Acid Quantification

In some embodiments of the methods provided herein, the method for quantification of a minority nucleic acid in a sample comprises the steps of (i) restriction digest, (ii) amplification, and (iii) separation. Each of these steps is described in detail herein. In some embodiments, the method further comprises an exonuclease step after amplification. In some embodiments the methods provided herein, the method for quantification of a minority nucleic acid does not include a protease (e.g. proteinase K) step after amplification. In some embodiments, the method does not include a dephosphorylation (e.g. shrimp alkaline phosphatase) step after amplification. In some embodiments, the method does not include a single base extension step after amplification. In some embodiments, the method does not include a salt elimination (e.g. water and resin) step after amplification. In some embodiments, the method does not include a crystallization step after amplification. In some embodiments, the method does not include mass spectrophotometry. In some embodiments of the methods provided herein, the method for quantification of a minority nucleic acid in a sample consists of the steps of (i) restriction digest, (ii) amplification, and (iii) separation. In some embodiments of the methods provided herein, the method for quantification of a minority nucleic acid in a sample consists of the steps of (i) restriction digest, (ii) amplification, (iii) exonuclease, and (iv) separation. In some embodiments, the method for quantification of a minority nucleic acid in a sample can be performed in a single day. In some embodiments, the method can be performed in about 4 hours to about 12 hours. For example, the method can be performed in about 4, 5, 6, 7, 8, 9, 10, 11 or 12 hours.

In some of the embodiments of the methods provided herein, the amount of a minority nucleic acid species in a sample is determined. Often, the amount of a minority nucleic acid species is determined based on the separated amplification products described above. The term "amount" as used herein with respect to amplified nucleic acids refers to any suitable measurement, including, but not limited to, absolute amount (e.g. copy number), relative amount (e.g. fraction or ratio), weight (e.g., grams), and concentration (e.g., grams per unit volume (e.g., milliliter); molar units).

Fraction Determination

In some embodiments, a fraction or ratio can be determined for the amount of one amplified nucleic acid relative to the amount of another amplified nucleic acid. In some embodiments, the fraction of a minority nucleic acid species in a sample relative to the total amount of the nucleic acid in the sample is determined based on the amount of each of the separated minority and (adjusted) total nucleic acid amplification products. To calculate the fraction of a minority nucleic acid species in a sample relative to the total amount of the nucleic acid in the sample, the following equation can be applied:

The fraction minority nucleic acid=(Concentration of the minority nucleic acid)/[(Concentration of total nucleic acid)× k)], where k is the damping coefficient by which the majority nucleic acid amplification product is modulated. In some cases, the damping coefficient (k) can be determined experimentally based on the ratio of total primers to inhibitor used in the amplification reaction described above. For example, to experimentally determine the damping coefficient, identical samples can be analyzed using 1) no inhibitors and 2) set amounts of PCR primer/inhibitor ratios. After PCR is performed, the concentration of amplification products can be calculated. The ratio difference between the products obtained with inhibitors compared to the products obtained without inhibitors is the damping coefficient.

The concentration of total nucleic acid multiplied by the damping coefficient (k) provides the adjusted amount of amplified total nucleic acid. In some cases, the concentrations of the total and minority species are obtained in a readout generated by the separation device (e.g. capillary electrophoresis device).

In some embodiments, the amount of an amplified minority nucleic acid is about equal to the adjusted amount of amplified total nucleic acid (i.e., amounts of amplified nucleic acids are about 1:1). In some embodiments, the amount of an amplified minority nucleic acid is about one half the adjusted amount of amplified total nucleic acid (i.e., amounts of amplified nucleic acids are about 1:2). In some embodiments, the amount of an amplified minority nucleic acid is about one third the amount of adjusted amplified total nucleic acid (i.e., amounts of amplified nucleic acids are about 1:3). In some embodiments, the amount of an amplified minority nucleic acid is about one fourth the amount of adjusted amplified total nucleic acid (i.e., amounts of amplified nucleic acids are about 1:4). In some embodiments, the amount of an amplified minority nucleic acid is about one tenth the adjusted amount of amplified total nucleic acid (i.e., amounts of amplified nucleic acids are about 1:10). In some embodiments, the amount an amplified minority nucleic acid is about one one hundredths the adjusted amount of amplified total nucleic acid (i.e., amounts of amplified nucleic acids are about 1:100).

Copy Number Determination Using Competitors

In some embodiments, the absolute amount (e.g. copy number) of a minority nucleic acid species is determined. Often, the copy number of a minority nucleic acid species is determined based on the amount of competitor oligonucleotide used. In some embodiments, the copy number of a majority nucleic acid species is determined. To calculate the copy number of a minority nucleic acid species in a sample, the following equation can be applied:

Copy number (minority nucleic acid species)=[(Concentration of the minority nucleic acid)/(Concentration of the minority competitor)]×C, where C is the number of competitor oligonucleotides added into the reaction. In some cases, the concentrations of the minority nucleic acid and minority competitor are obtained in a readout generated by the separation device (e.g. capillary electrophoresis device).

Sequencing

In some embodiments, amplification products generated from the methods provided herein may be subject to sequence analysis. In some embodiments, a determination is made whether a particular nucleic acid sample can be used for sequencing analysis based on the quantitative data obtained for a sample using the methods provided herein. In some embodiments, a determination is made whether the sequencing information obtained for a nucleic acid can be used for one or more diagnostic determinations based on the quantitative data obtained for a sample using the methods provided herein. Such determinations can be made based on the amount of a nucleic acid species (e.g. minority nucleic acid, fetal nucleic acid, nucleic acid from cancer cells, pathogen nucleic acid) detected for a given sample. In some cases, a determination can be based on a threshold amount determined by the practitioner for a given nucleic acid species. In some embodiments, the threshold amount can be at least about 1% to about 40% of the total nucleic acid in a sample. For example, the threshold amount can be at least about 1, 2, 3, 4, 5, 6, 7, 8, 9, 10, 11, 12, 13, 14, 15, 16, 17, 18, 19, 20, 25, 30, 35, or 40% of total nucleic acid in a sample.

The term "sequence analysis" as used herein refers to determining a nucleotide sequence of an amplification product. The entire sequence or a partial sequence of an amplification product can be determined, and the determined nucleotide sequence is referred to herein as a "read." For example, linear amplification products may be analyzed directly without further amplification in some embodiments (e.g., by using single-molecule sequencing methodology (described in greater detail hereafter)). In certain embodiments, linear amplification products may be subject to further amplification and then analyzed (e.g., using sequencing by ligation or pyrosequencing methodology (described in greater detail hereafter)). Reads may be subject to different types of sequence analysis. Any suitable sequencing method can be utilized to detect, and determine the amount of, nucleotide sequence species, amplified nucleic acid species, or detectable products generated from the foregoing. Examples of certain sequencing methods are described hereafter.

In some embodiments, one nucleic acid sample from one individual is sequenced. In certain embodiments, nucleic acid samples from two or more samples, where each sample is from one individual or two or more individuals, are pooled and the pool is sequenced. In the latter embodiments, a nucleic acid sample from each sample is identified by one or more unique identification tags. For a pooled sample sequencing run, each pool can contain a suitable number of samples, such as, for example 2 samples (i.e. 2-plex), 3 samples (i.e. 3-plex), 4 samples (i.e. 4-plex), 5 samples (i.e. 5-plex), or more.

In certain embodiments, a fraction of a nucleic acid pool that is sequenced in a run is further sub-selected prior to sequencing. In certain embodiments, hybridization-based techniques (e.g., using oligonucleotide arrays) can be used to first sub-select for nucleic acid sequences from certain chromosomes (e.g. a potentially aneuploid chromosome and other chromosome(s) not involved in the aneuploidy tested). In some embodiments, nucleic acid can be fractionated by size (e.g., by gel electrophoresis, size exclusion chromatography or by microfluidics-based approach) and in certain instances, fetal nucleic acid can be enriched by selecting for nucleic acid having a lower molecular weight (e.g., less than 300 base pairs, less than 200 base pairs, less than 150 base pairs, less than 100 base pairs). In some embodiments, fetal nucleic acid can be enriched by suppressing maternal background nucleic acid, such as by the addition of formaldehyde. In some embodiments, a portion or subset of a pre-selected pool of nucleic acids is sequenced randomly.

The terms "sequence analysis apparatus" and "sequence analysis component(s)" used herein refer to apparatus, and one or more components used in conjunction with such apparatus, that can be used by a person of ordinary skill to determine a nucleotide sequence from amplification products resulting from processes described herein (e.g., linear and/or exponential amplification products). Examples of sequencing platforms include, without limitation, the 454 platform (Roche) (Margulies, M. et al. 2005 Nature 437, 376-380), Illumina Genomic Analyzer (or Solexa platform) or SOLID System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53: 1996-2001). Such platforms allow sequencing of many nucleic acid molecules isolated from a specimen at high orders of multiplexing in a parallel manner (Dear Brief Funct Genomic Proteomic 2003; 1: 397-416). Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing. Nucleotide sequence species, amplification nucleic acid species and detectable products generated there from can be considered a "study nucleic acid" for purposes of analyzing a nucleotide sequence by such sequence analysis platforms. A massively parallel sequencing process often produces many short nucleotide sequences that sometimes are referred to as "reads." Reads can be generated from one end of nucleic acid fragments ("single-end reads"), and sometimes are generated from both ends of nucleic acids ("double-end reads").

In some embodiments, single-end sequencing is performed. Such sequencing can be performed using an Illumina Genome Analyzer (Illumina, San Diego, Calif.), for example. The Illumina Genome Analyzer sequences clonally-expanded single DNA molecules captured on a solid surface termed a flow cell. Each flow cell has eight lanes for the sequencing of eight individual specimens or pools of specimens. Each lane is capable of generating about 200 Mb of sequence which is only a fraction of the 3 billion base pairs of sequences in the human genome. Each genomic DNA or plasma DNA sample is sequenced using one lane of a flow cell. The short sequence tags generated are aligned to a reference genome sequence and the chromosomal origin is noted. The total number of individual sequenced tags aligned to each chromosome are tabulated and compared with the relative size of each chromosome as expected from the reference genome.

In some embodiments, reversible terminator-based sequencing is performed. Reversible terminator-based sequencing can detect single bases as they are incorporated into growing DNA strands. A fluorescently-labeled terminator is imaged as each dNTP is added and then cleaved to allow incorporation of the next base. Since all four reversible terminator-bound dNTPs are present during each sequencing cycle, natural competition minimizes incorporation bias. Base calls can be made directly from signal intensity measurements during each cycle, which can reduce raw error rates compared to other technologies. The end result is highly accurate base-by-base sequencing that can eliminate sequence-context specific errors. Such sequencing can be performed using any machine designed to perform a reversible terminator-based sequencing reaction, such as the Illumina HISEQ 2000 Genome Analyzer (Illumina, San Diego, Calif.), for example. Using the HISEQ 2000 Genome Analyzer, flow cells are loaded on a vacuum-controlled loading dock. Pre-configured reagents sufficient for up to 200 cycles drop into racks in the machine's chiller compartment. The HISEQ 200 Genome Analyzer can be operated in a single or duel flow cell mode. Independently-operable flow cells can allow applications requiring different read lengths to run simultaneously.

In some embodiments, sequencing by ligation is performed, which is a method that relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucleotides or primers, enables sequence determination by fluorescence detection. Longer sequence reads may be obtained by including primers containing cleavable linkages that can be cleaved after label identification. Cleavage at the linker removes the label and regenerates the 5' phosphate on the end of the ligated primer, preparing the primer for another round of ligation. In some embodiments primers may be labeled with more than one fluorescent label (e.g., 1 fluorescent label, 2, 3, or 4 fluorescent labels).

An example of a system that can be used by a person of ordinary skill based on sequencing by ligation generally involves the following steps. Clonal bead populations can be prepared in emulsion microreactors containing study nucleic acid ("template"), amplification reaction components, beads and primers. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four color dye-labeled probes competes for ligation to the sequencing primer. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in the 5' direction is laid down for another series of ligations. Primer reset and ligation rounds (5-7 ligation cycles per round) are repeated sequentially five times to generate 25-35 base pairs of sequence for a single tag. With mate-paired sequencing, this process is repeated for a second tag. Such a system can be used to exponentially amplify amplification products generated by a process described herein, e.g., by ligating a heterologous nucleic acid to the first amplification product generated by a process described herein and performing emulsion amplification using the same or a different solid support originally used to generate the first amplification product. Such a system also may be used to analyze amplification products directly generated by a process described herein by bypassing an exponential amplification process and directly sorting the solid supports described herein on the glass slide.

In some embodiments, pyrosequencing is used, which is a nucleic acid sequencing method based on sequencing by synthesis, and relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination.

An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., "Single-molecule PCR using water-in-oil emulsion;" Journal of Biotechnology 102: 117-124 (2003)). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., U.S. Pat. No. 7,169,314; Braslaysky et al., PNAS 100(7): 3960-3964 (2003)). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer—released linear amplification product complexes with the immobilized capture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer—released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, nucleotide sequencing may be by solid phase single nucleotide sequencing methods and processes. Solid phase single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008.

In certain embodiments, nanopore sequencing detection methods include (a) contacting a nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53(11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the detectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known in the art (e.g., Venter et al., Science 291: 1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons sometimes are performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis is facilitated by sequence analysis apparatus and components known in the art.

Diagnostic Determination

In some embodiments of the methods provided herein, a diagnostic determination is made. Diagnostic determination can be made for any condition where the detection, quantification and/or sequencing of a nucleic acid species can be indicative of that condition. In some cases, the presence or absence of a fetal chromosome abnormality (e.g. fetal aneuploidy) is determined or sex (i.e. gender) determination is performed. In some cases, the presence or absence of a cell proliferation disorder (e.g. cancer) or pathogen (e.g. virus, bacteria, fungus) is determined.

In some cases, a diagnostic determination is made in conjunction with other methods provided herein, such as, for example, sequencing. In some cases, the methods provided herein can be used to determine whether sequencing information obtained for a nucleic acid sample is used for a diagnostic determination. Such determinations can be made based on the amount of a nucleic acid species (e.g. minority nucleic acid, fetal nucleic acid, nucleic acid from cancer cells, pathogen nucleic acid) detected for a given sample. In some cases, a determination can be based on a threshold amount determined by the practitioner for a given nucleic acid species. In some embodiments, the threshold amount can be at least about 1% to about 40% of the total nucleic acid in a sample. For example, the threshold amount can be at least about 1, 2, 3, 4, 5, 6, 7, 8, 9, 10, 11, 12, 13, 14, 15, 16, 17, 18, 19, 20, 25, 30, 35, or 40% of total nucleic acid in a sample.

Chromosome Abnormalities

In some embodiments, the presence or absence of a fetal chromosome abnormality is determined. Chromosome abnormalities include, without limitation, a gain or loss of an entire chromosome or a region of a chromosome comprising one or more genes. Chromosome abnormalities include monosomies, trisomies, polysomies, loss of heterozygosity, deletions and/or duplications of one or more nucleotide sequences (e.g., one or more genes), including deletions and duplications caused by unbalanced translocations. The terms "aneuploidy" and "aneuploid" as used herein refer to an abnormal number of chromosomes in cells of an organism. As different organisms have widely varying chromosome complements, the term "aneuploidy" does not refer to a particular number of chromosomes, but rather to the situation in which the chromosome content within a given cell or cells of an organism is abnormal.

The term "monosomy" as used herein refers to lack of one chromosome of the normal complement. Partial monosomy can occur in unbalanced translocations or deletions, in which only a portion of the chromosome is present in a single copy (see deletion (genetics)). Monosomy of sex chromosomes (45, X) causes Turner syndrome.

The term "disomy" refers to the presence of two copies of a chromosome. For organisms such as humans that have two copies of each chromosome (those that are diploid or "euploid"), it is the normal condition. For organisms that normally have three or more copies of each chromosome (those that are triploid or above), disomy is an aneuploid chromosome complement. In uniparental disomy, both copies of a chromosome come from the same parent (with no contribution from the other parent).

The term "trisomy" refers to the presence of three copies, instead of the normal two, of a particular chromosome. The presence of an extra chromosome 21, which is found in Down syndrome, is called trisomy 21. Trisomy 18 and Trisomy 13 are the two other autosomal trisomies recognized in live-born humans. Trisomy of sex chromosomes can be seen in females (47, XXX) or males (47, XXY which is found in Klinefelter's syndrome; or 47,XYY).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing nondisjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the portion that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism most likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and kits described herein can identify presence or absence of non-mosaic and mosaic chromosome abnormalities.

Following is a non-limiting list of chromosome abnormalities that can be potentially identified by methods and kits described herein.

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphproliferative disease |
| 1 | 1p (somatic) monosomy trisomy | neuroblastoma |
| 2 | monosomy trisomy 2q | growth retardation, developmental and mental delay, and minor physical abnormalities |
| 3 | monosomy trisomy (somatic) | Non-Hodgkin's lymphoma |
| 4 | monosomy trsiomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobson Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |

-continued

| Chromosome | Abnormality | Disease Association |
|---|---|---|
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL) |
| 16 | 16q13.3 deletion | Rubenstein-Taybi |
|  | monosomy trisomy (somatic) | papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy |  |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

Preeclampsia

In some embodiments of the methods provided herein, the presence or absence of preeclampsia is determined. Preeclampsia is a condition in which hypertension arises in pregnancy (i.e. pregnancy-induced hypertension) and is associated with significant amounts of protein in the urine. In some cases, preeclampsia also is associated with elevated levels of extracellular nucleic acid and/or alterations in methylation patterns (see e.g. Kulkarni et al., (2011) DNA Cell Biol. 30(2):79-84; Hahn et al., (2011) Placenta 32 Suppl: S17-20). For example, a positive correlation between extracellular fetal-derived hypermethylated RASSF1A levels and the severity of pre-eclampsia has been observed (Zhao, et al., (2010) Pretat. Diagn. 30(8):778-82). In another example, increased DNA methylation was observed for the H19 gene in preeclamptic placentas compared to normal controls (Gao et al., (2011) Hypertens Res. February 17 (epub ahead of print)).

Preeclampsia is one of the leading causes of maternal and fetal/neonatal mortality and morbidity worldwide. Thus, widely applicable and affordable tests are needed to make an early diagnosis before the occurrence of the clinical symptoms. Circulating cell-free nucleic acids in plasma and serum are novel biomarkers with promising clinical applications in different medical fields, including prenatal diagnosis. Quantitative changes of cell-free fetal (cff)DNA in maternal plasma as an indicator for impending preeclampsia have been reported in different studies, for example, using real-time quantitative PCR for the male-specific SRY or DYS14 loci. In cases of early onset preeclampsia, elevated levels may be seen in the first trimester. The increased levels of cffDNA before the onset of symptoms may be due to hypoxia/reoxygenation within the intervillous space leading to tissue oxidative stress and increased placental apoptosis and necrosis. In addition to the evidence for increased shedding of cffDNA into the maternal circulation, there is also evidence for reduced renal clearance of cffDNA in preeclampsia. As the amount of fetal DNA is currently determined by quantifying Y-chromosome specific sequences, alternative approaches such as the measurement of total cell-free DNA or the use of gender-independent fetal epigenetic markers, such as DNA methylation, offer an alternative. Cell-free RNA of placental origin might be another potentially useful biomarker for screening and diagnosis of preeclampsia in clinical practice. Fetal RNA is associated with subcellular placental particles that protect it from degradation. Its levels are ten-fold higher in pregnant women with preeclampsia compared to controls.

Cancer

In some embodiments, the presence or absence of a cell proliferation disorder (e.g. cancer) is determined. For example, levels of cell-free nucleic acid in serum can be elevated in patients with various types of cancer compared with healthy patients. Patients with metastatic diseases, for example, can sometimes have serum DNA levels approximately twice as high as non-metastatic patients. Non-limiting examples of cancer types that can be positively correlated with elevated levels of circulating DNA include, breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from healthy cells, such as, for example, epigenetic state and/or sequence variations, duplications and/or deletions. Such characteristics can, for example, be specific to a particular type of cancer. Thus, it is further contemplated that the methods provided herein can be used to identify a particular type of cancer.

Pathogens

In some embodiments, the presence or absence of a pathogenic condition is determined. A pathogenic condition can be caused by infection of a host by any pathogen including, but not limited to, bacteria, viruses or fungi. Since pathogens typically possess nucleic acid (e.g. genomic DNA, genomic RNA, mRNA) that can be distinguishable from the host nucleic acid, the methods provided herein can be used to diagnose the presence or absence of a pathogen. Often, pathogens possess nucleic acid with characteristics that are unique to a particular pathogen such as, for example, epigenetic state and/or sequence variations, duplications and/or deletions. Thus, it is further contemplated that the methods provided herein can be used to identify a particular pathogen or pathogen variant (e.g. strain).

Samples

Nucleic acid utilized in methods and kits described herein often is obtained and isolated from a subject. A subject can be any living or non-living source, including but not limited to a human, an animal, a plant, a bacterium, a fungus, a protist. Any human or animal can be selected, including but not limited, non-human, mammal, reptile, cattle, cat, dog, goat, swine, pig, monkey, ape, gorilla, bull, cow, bear, horse, sheep, poultry, mouse, rat, fish, dolphin, whale, and shark.

Nucleic acid may be isolated from any type of fluid or tissue from a subject, including, without limitation, umbilical cord blood, chorionic villi, amniotic fluid, cerbrospinal fluid, spinal fluid, lavage fluid (e.g., bronchoalveolar, gastric, peritoneal, ductal, ear, athroscopic), biopsy sample (e.g., from pre-implantation embryo), celocentesis sample, fetal nucleated cells or fetal cellular remnants, washings of female reproductive tract, urine, feces, sputum, saliva, nasal mucous, prostate fluid, lavage, semen, lymphatic fluid, bile, tears, sweat, breast milk, breast fluid, embryonic cells and fetal cells (e.g. placental cells). In some embodiments, a biological sample may be blood, and sometimes plasma. As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to further preparation in such embodiments. A fluid or tissue sample from which nucleic acid is extracted may be acellular. In some embodiments, a fluid or tissue sample may contain cellular elements or cellular remnants. In some embodiments fetal cells or cancer cells may comprise the sample.

The sample may be heterogeneous, by which is meant that more than one type of nucleic acid species is present in the sample. For example, heterogeneous nucleic acid can include, but is not limited to, (i) fetally derived and maternally derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant woman at 1-4, 4-8, 8-12, 12-16, 16-20, 20-24, 24-28, 28-32, 32-36, 36-40, or 40-44 weeks of fetal gestation, and sometimes between 5-28 weeks of fetal gestation.

Nucleic Acid Isolation

Nucleic acid may be derived from one or more sources (e.g., cells, soil, etc.) by methods known in the art. Cell lysis procedures and reagents are commonly known in the art and may generally be performed by chemical, physical, or electrolytic lysis methods. For example, chemical methods generally employ lysing agents to disrupt the cells and extract the nucleic acids from the cells, followed by treatment with chaotropic salts. Physical methods such as freeze/thaw followed by grinding, the use of cell presses and the like are also useful. High salt lysis procedures are also commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, solution 1 can contain 15 mM Tris, pH 8.0; 10 mM EDTA and 100 ug/ml Rnase A; solution 2 can contain 0.2N NaOH and 1% SDS; and solution 3 can contain 3M KOAc, pH 5.5. These procedures can be found in Current Protocols in Molecular Biology, John Wiley & Sons, N.Y., 6.3.1-6.3.6 (1989), incorporated herein in its entirety.

Nucleic acid also may be isolated at a different time point as compared to another nucleic acid, where each of the samples are from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acid may be provided for conducting methods described herein without processing of the sample(s) containing the nucleic acid in certain embodiments. In some embodiments, nucleic acid is provided for conducting methods described herein after processing of the sample(s) containing the nucleic acid. For example, a nucleic acid may be extracted, isolated, purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. An isolated nucleic acid generally is provided with fewer non-nucleic acid components (e.g., protein, lipid) than the amount of components present in a source sample. A composition comprising isolated nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to nucleic acid provided that contains fewer nucleic acid species than in the sample source from which the nucleic acid is derived. A composition comprising nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a sample to a process that linearly or exponentially generates amplicon nucleic acids having the same or substantially the same nucleotide sequence as the nucleotide sequence of the nucleic acid in the sample, or portion thereof.

Kits

Kits often are made up of one or more containers that contain one or more components described herein. A kit comprises one or more components in any number of separate containers, packets, tubes, vials, multiwell plates and the like, or components may be combined in various combinations in such containers. One or more of the following components, for example, may be included in a kit: (i) one or more enzymes for cleaving nucleic acid; (ii) one or more amplification primer pairs for amplifying a nucleotide sequence or nucleotide sequences for one or more regions; (iii) one or more inhibitory oligonucleotides; (iv) one or more competitor oligonucleotides; (v) reagents and/or equipment for amplifying nucleic acids; (vi) reagents and/or equipment for a process for separating amplified nucleic acids; (vii) software and/or a machine for analyzing signals resulting from a process for separating the amplified nucleic acids; (viii) information for calculating the relative amount and/or copy number of a nucleic acid, (ix) equipment for drawing blood; (x) equipment for generating cell-free blood; (xi) reagents for isolating nucleic acid (e.g., DNA, RNA) from plasma, serum or urine; (xii) reagents for stabilizing serum, plasma, urine or nucleic acid for shipment and/or processing.

A kit sometimes is utilized in conjunction with a process, and can include instructions for performing one or more processes and/or a description of one or more compositions. A kit may be utilized to carry out a process described herein. Instructions and/or descriptions may be in tangible form (e.g., paper and the like) or electronic form (e.g., computer readable file on a tangle medium (e.g., compact disc) and the like) and may be included in a kit insert. A kit also may include a written description of an internet location that provides such instructions or descriptions (e.g., a URL for the World-Wide Web).

Thus, provided herein is a kit that comprises one or more amplification primer pairs for amplifying a nucleotide sequence or nucleotide sequences for one or more regions, one or more inhibitory oligonucleotides, and one or more competitor oligonucleotides. In some embodiments, one or more primers in the kit are selected from those described herein. In some embodiments, one or more inhibitory oligonucleotides in the kit are selected from those described herein. In some embodiments, one or more competitor oligonucleotides in the kit are selected from those described herein. The kit also comprises a conversion table, software, executable instructions, and/or an internet location that provides the foregoing, in certain embodiments, where a conversion table, software and/or executable instructions can be utilized to convert data resulting from separation and quantification of amplified nucleic acids into relative amounts or copy number. A kit also may comprise one or more enzymes for nucleic acid cleavage, in certain embodiments. In some embodiments, a kit comprises reagents and/or equipment for performing an amplification reaction (e.g., polymerase, nucleotides, buffer solution, thermocycler, oil for generating an emulsion).

EXAMPLES

The examples set forth below illustrate certain embodiments and do not limit the technology.

Example 1

Materials and Methods

The materials and methods set forth in this Example were used to perform diagnostic assays described in Examples 2-9, except where otherwise noted.

Fetal DNA Quantification Assay

A test for accurate quantification of circulating cell free fetal (CCFF) DNA using methylation based DNA discrimination was developed. The fetal DNA quantification assay (FQA) described herein was designed according to several criteria including: 1) the assay would be a single well test to enable multiple measurements from the same blood sample, while reserving a majority of the plasma derived DNA for further analytical assays, such as, for example, RhD, Fetal sexing or aneuploidy testing, 2) the assay would not consume more than 25% of the available DNA obtained from a 4 ml extraction, 3) the assay would be a multiplex assembly made up of four different types of assays for the detection and quantification of fetal methylated DNA, total DNA, male DNA and controls for the restriction digest reaction, 4) the multiplex would contain several markers for each of the four types of assays to minimize measurement variance, 5) a high resolution, microfluidics (i.e. capillary)-based electrophoretic nucleic acid separation system and/or a reversible terminator-based sequencing system could be used for the analysis, and 6) the assay would be evaluated with regards to reproducibility, accuracy and precision, and would be designed to have equal or better performance compared to other fetal DNA quantification assays including, for example, the MassARRAY based FQA. Particular details regarding the development of the fetal DNA quantification assay are described below.

Amplicon Design

The assay provided herein for fetal DNA quantification was designed such that the amplified DNA sequences and competitive oligonucleotides for each marker could be differentiated by amplicon length. Specifically, sets of PCR amplicons were designed where each multiplex set was made up of four markers (i.e. genomic DNA target sequences): methylation, total DNA, chromosome Y and digestion controls. In this assay, all markers were made up of genomic DNA regions of identical length. The PCR primers, however, contained 5' non-hybridizing tails of varying length, which enabled separation of each amplicon using electrophoresis. To achieve exact quantification of DNA in this assay, competitor oligonucleotides of known amounts were co-amplified. These competitor oligonucleotides were not of identical length or sequence and contained a stuffer sequence to distinguish the competitor oligonucleotide amplicons from the genomic DNA amplicons (see e.g. FIG. 1). The stuffer sequence was not specific to the human genome and was obtained from the PhiX 174 genome. Table 1 below presents the design scheme for the genomic DNA amplicons and the competitor oligonucleotide amplicons.

TABLE 1

Design of Amplicon Length

| | Target Length | Primer Tail | Amplicon Length |
|---|---|---|---|
| Methylated DNA | 70 | 0 + 0 | 70 |
| Total DNA | 70 | 6 + 5 | 81 |
| Chromosome Y DNA | 70 | 11 + 12 | 93 |

TABLE 1-continued

Design of Amplicon Length

| | Target Length | Primer Tail | Amplicon Length |
|---|---|---|---|
| Digestion Control DNA | 70 | 18 + 18 | 106 |
| Methylated COMPETITOR | 115 | 0 + 0 | 115 |
| Total COMPETITOR | 115 | 6 + 5 | 126 |
| Chromosome Y COMPETITOR | 118 | 11 + 12 | 141 |
| Digestion Control COMPETITOR | 120 | 18 + 18 | 156 |

Figure 2:
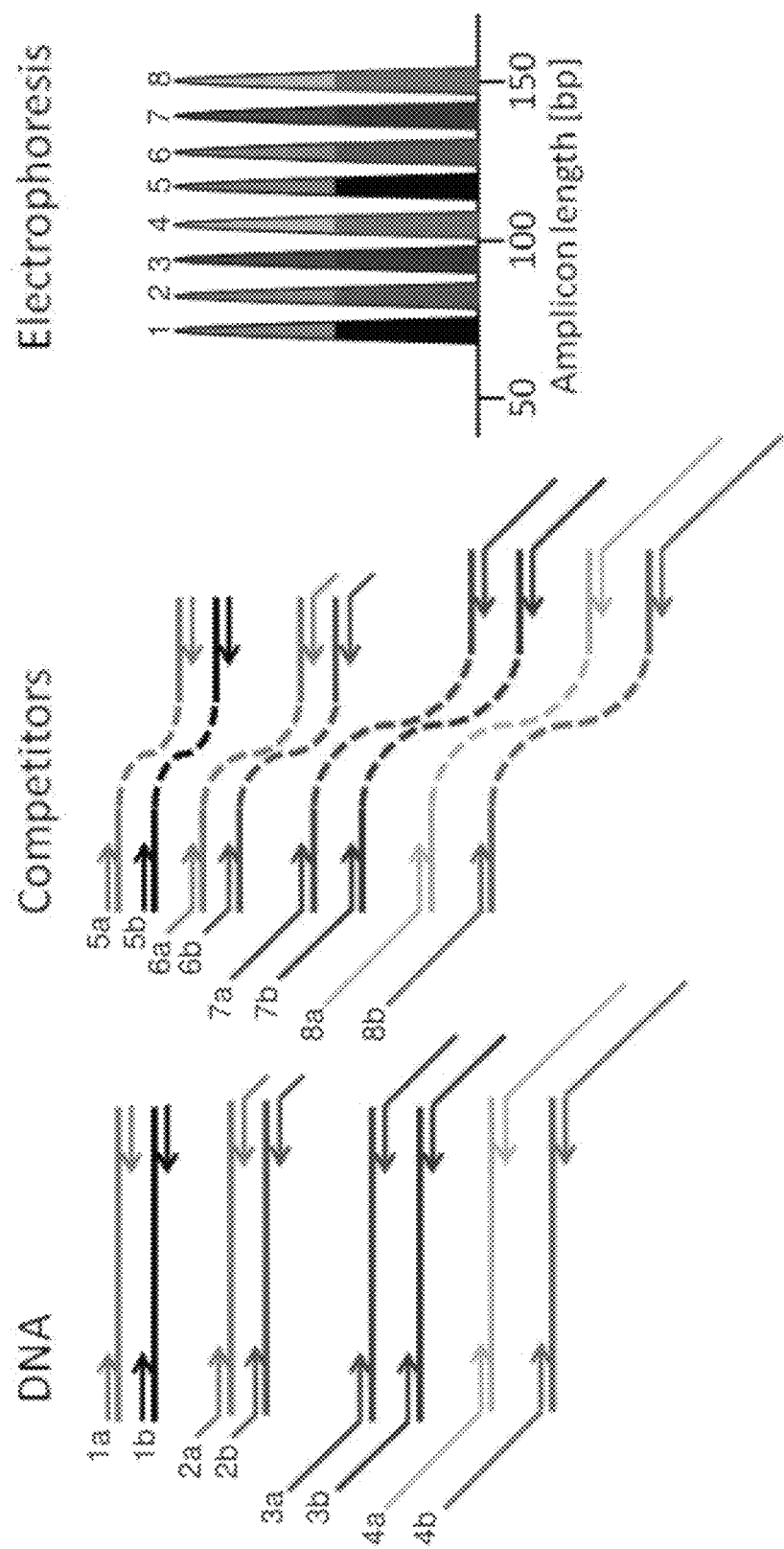
FIG. 2 illustrates an example of an amplification scheme where a plurality of amplicons is generated for each region. Accurate quantification is obtained using several amplicons per region and stacking each set on top of each other. Specifically, the genomic DNA target sequences for each region and their corresponding competitors are outlined in the scheme as follows: Methylation (1a, 1b and 5a, 5b), Total DNA (2a, 2b and 6a, 6b), Chromosome Y (3a, 3b and 7a, 7b) and Digestion control (4a, 4b and 8a, 8b). Each electropherogram peak, numbered 1 through 8, is generated from multiple independent targets or competitors.

Compared to DNA derived from the cellular compartment of a blood draw, cell-free DNA from plasma can be several orders of magnitude less abundant. In particular, the fetal fraction, which generally constitutes about 3% to about 25% of all circulating cell-free DNA, can be limited. Because of the low copy numbers to be detected, redundant measurements were made to increase the confidence in the results. Fragments of the same length were selected to avoid unnecessary amplification bias. As described above, tailed primers of varying length were used to separate the different amplicons, which allowed for generation of unique amplicon length. To enable redundant measurements, the assay was designed such that each peak in the electropherogram was generated from several independent amplicons per marker (see FIG. 2). Specifically, as shown in FIG. 2, independent amplicons 1a and 1b designed to represent the methylation marker, for example, together generated peak #1 in the electropherogram. Using this assay design, the necessity for multiple measurements was addressed despite the limited resolution of electrophoresis. As each peak in the electropherogram was made up of several independent amplicons, the technical as well as the biological variability of the assay was reduced.

Genomic Target Selection

As described above, a fetal DNA quantification assay (FQA) provided herein includes a multiplex PCR reaction where four types of assays were carried out. These include, 1) assays for the detection and quantification of methylated placental (fetal) DNA, 2) assays for the detection and quantification of total DNA, 3) assays for the detection and quantification of total copies of Chromosome Y specific sequences, and 4) assays for the detection and quantification of undigested DNA. Each assay was manually designed according to the criteria set forth below.

Assays for the Detection and Quantification of Methylated Placental DNA

The following criteria were observed while selecting the genomic loci targets, PCR primers, and competitor oligonucleotides for the detection and quantification of methylated placental DNA assays. 1) Each locus was a single copy gene, not located Chr. 13, 18, 21, X or Y. 2) There was minimal maternal methylation (<1%), and a placental methylation (>50%) for each locus. 3) There were no known SNPs, mutations or insertions/deletions located under the PCR primer sequences. 4) At least two restriction sites ((GCGC CCGG), any combination) existed within each locus. 5) The genomic sequence length and final product was exactly 70 bp. 6) The competitor length would be 115 bp long generating a final length of 126 bp using untailed PCR primers. 7) The melting temperature of the PCR primers was not below 65° C. and not above 75° C. 8) There were no negative ΔG values for secondary structure of the complete amplicon prediction using mfold (M. Zuker, Mfold web server for nucleic acid folding and hybridization prediction. Nucleic Acids Res. 31 (13), 3406-15, (2003)).

Assays for the Detection and Quantification of Total DNA

The following criteria were observed while selecting the genomic loci targets, PCR primers, and competitor oligonucleotides for the detection and quantification of total DNA. 1) Each locus was a single copy gene lacking restriction sites (GCGC CCGG), not located Chr. 13, 18, 21, X or Y. 2) The genomic sequence length was exactly 70 bp, but the final amplicon length was 81 bp using tailed primers (5+6 bp). 3) There were no known SNPs, mutations or insertions/deletions located under the PCR primer sequences. 4) The melting temperature of PCR primers was not below 65° C. and not above 75° C. 5) The competitor length would be 115 bp long generating a final length of 126 bp. 6) There were no negative ΔG values for secondary structure prediction of the complete amplicon or competitor using mfold (M. Zuker, Mfold web server for nucleic acid folding and hybridization prediction. Nucleic Acids Res. 31 (13), 3406-15, (2003)).

Assays for the Detection and Quantification of Total Copies of Chromosome Y Specific Sequences The following criteria were observed while selecting the genomic loci targets, PCR primers, and competitor oligonucleotides for the detection and quantification of total copies of Chromosome Y specific sequences. 1) Each locus was a single copy gene lacking restriction sites (GCGC CCGG), specific to chromosome Y. 2) The genomic sequence length was exactly 70 bp, but final amplicon length was 93 bp using tailed primers (11+12 bp). 3) There were no known SNPs, mutations or insertions/deletions located under the PCR primer sequences. 4) The melting temperature of the PCR primers was not below 65° C. and not above 75° C. 5) The competitor length would be 118 bp long generating a final length of 141 bp. 6) There were no negative ΔG values for secondary structure of the complete amplicon prediction using mfold (M. Zuker, Mfold web server for nucleic acid folding and hybridization prediction. Nucleic Acids Res. 31 (13), 3406-15, (2003)).

Assays for the Detection and Quantification of Undigested DNA

The following criteria were observed while selecting the genomic loci targets, PCR primers, and competitor oligonucleotides for the detection and quantification of undigested DNA. 1) Each locus was a single copy gene, known to be unmethylated in all tissues and not located Chr. 13, 18, 21, X or Y. 2). Each amplicon contained exactly one site for each restriction enzyme i.e. (GCGC or CCGG). 3) There were no known SNPs, mutations or insertions/deletions located under the PCR primer sequences. 4) The genomic sequence length was exactly 70 bp, but the final amplicon length was 106 bp using tailed primers (18+18 bp). 5) The melting temperature of the PCR primers was not below 65° C. and not above 75° C. 6) The competitor length would be 120 bp long generating a final length of 156 bp. 7) There were no negative ΔG values for secondary structure of the complete amplicon prediction using mfold (M. Zuker, Mfold web server for nucleic acid folding and hybridization prediction. Nucleic Acids Res. 31 (13), 3406-15, (2003)).

Table 2 below presents the genomic target loci selected for each of the four assays described above.

TABLE 2

Genomic Target Loci

| Locus | Assay Type | Sequence | SEQ ID NO | Length (bp) |
|---|---|---|---|---|
| TBX3 | Meth | CTTTGTCTCTGCGTGCCCGGCGCG CCCCCCTCCCGGTGGGTGATAAAC CCACTCTGGCGCCGGCCATGCG | 29 | 70 |
| SOX14 | Meth | CCACGGAATCCCGGCTCTGTGTGC GCCCAGGTTCCGGGGCTTGGGCGT TGCCGGTTCTCACACTAGGAAG | 30 | 70 |
| POP5 | Total | CCACCAGTTTAGACTGAACTGTGA ACGTGTCACCAATTGAAAATCAGT AGCCATACCACCTCACTCCTAC | 31 | 70 |
| APOE | Total | GACAGTTTCTCCTTCCCCAGACTG GCCAATCACAGGCAGGAAGATGAA GGTTCTGTGGGCTGCGTTGCTG | 32 | 70 |
| UTY | Chr Y | GATGCCGCCCTTCCCATCGCTCTC TTCCCCTTCAAGCGTATCGCAACT GCAAAAACACCCAGCACAGACA | 33 | 70 |
| DDX3Y | Chr Y | CCTTCTGCGGACCTGTTCTTTCAC CTCCCTAACCTGAAGATTGTATTC AAACCACCGTGGATCGCTCACG | 34 | 70 |
| DIGctrl1 | Control | CACTCGTGCCCCTTCTTTCTTCCT CCGGCGCCTGCCCCCTCCACATCC CGCCATCCTCCCGGGTTCCCCT | 35 | 70 |
| DIGctrl2 | Control | GACAGGCCTTTGCAACAAGGATCA CGGCCGAAGCCACACCGTGCGCCT CCCTCCCGGTTGGTTAACAGGC | 36 | 70 |

Following the selection of genomic target loci, competitor oligonucleotides were designed for the fetal DNA quantification assay according to the methods described above. Table 3 below presents the competitor oligonucleotides.

TABLE 3

Competitor Oligonucleotides

| Competitor | Amount (copy number) | Sequence | SEQ ID NO | Length (bp) |
|---|---|---|---|---|
| TBX3 | 200 | CTTTGTCTCTGCGTGCCCGGCAA TTCGGATGTTCGTCAAGGACGCG CCCCCCTCCCGGTGGGTGATAAA CCGATTAAGTTCATCAAGTCTGA TCCACTCTGGCGCCGGCCATGCG | 21 | 115 |
| SOX14 | 200 | CCACGGAATCCCGGCTCTGTGCA GTTTTCTGGTCGTGTTCAACATG CGCCAGGTTCCGGGGCTTGGGC ATGACTTCGTGATAAAAGATTCG TTGCCGGTTCTCACACTAGGAAG | 22 | 115 |
| POP5 | 2000 | CCACCAGTTTAGACTGAACTGTG AACGCTTGGCTTCCATAAGCAGA TGGGTGTCACCAATTGAAAATCA CTCTTAAGGATATTCGCGATGAG TAGCCATACCACCTCACTCCTAC | 23 | 115 |
| APOE | 2000 | GACAGTTTCTCCTTCCCCAGACT GACTGCCTATGATGTTTATCCTG GCCAATCACAGGCAGGAAGATGAA AGGTCTGATAAAGGAAAGGATAC TCGTTCTGTGGGCTGCGTTGCTG | 24 | 115 |
| SRY | N/A | GTGCAACTGGACAACAGGTTGTA CAGGGATGACTGTTTTATGATAA | 37 | 118 |

TABLE 3-continued

Competitor Oligonucleotides

| Competitor | Amount (copy number) | Sequence | SEQ ID NO | Length (bp) |
|---|---|---|---|---|
| | | TCCCAATGCTTTGCGTGACTATT TTCGTGATATTGGGTACGAAAGC CACACACTCAAGAATGGAGCACC AGC | | |
| UTY | 200 | GATGCCGCCCTTCCCATCGCTCT CTTCCCCTTCATCAGTATTTTAC CAATGACCAAATCAAAGAAATGA CTCGCAAGGTTAGAGCGTATCGC AACTGCAAAAACACCCAGCACAG ACA | 25 | 118 |
| DDX3Y | 200 | CCTTCTGCGGACCTGTTCTTTCA CCTCCCTAACCTGAGCAGCGTTA CCATGATGTTATTTCTTCATTTG GAGGTAAAACCTCTTAAGATTGT ATTCAAACCACCGTGGATCGCTC ACG | 26 | 118 |
| DIGctrl1 | 200 | CACTCGTGCCCCTTCTTTCTTCT TATGTTCATCCCGTCAACATTCA ACTCCGGCGCCTGCCCCCTCCAC ATCCCGATAGCTTGCAAAATAC GTGGCCTTACATCCTCCCGGGTT CCCCT | 27 | 120 |
| DIGctrl2 | 200 | GACAGGCCTTTGCAACAAGGATC TAACCCTAATGAGCTTAATCAAG ATACGGCCGAAGCCACACCGTGC GCCTCAGGAAACACTGACGTTCT TACTGACCCTCCCGGTTGGTTAA CAGGC | 28 | 120 |

Table 3: List of competitor oligonucleotides used in the fetal DNA quantification assay. Bold letters indicate PhiX 174 genomic DNA stuffer sequences.
Targeted inhibitory PCR To reliably monitor small changes in copy number of the target genes, the signal strength and ratios should not be influenced by the number of PCR cycles and large changes in copy numbers of a certain gene should not influence the signals of the other markers. Because the number of methylated sequences is only a fraction of the total sequences in the fetal quantification assay provided herein, the electropherogram would be dominated by the peaks generated by the markers for total DNA if traditional PCR were employed. This would reduce the analytical window of the assay and make quantification difficult. This problem was overcome by the use of targeted inhibitory PCR.

In this approach, a specific inhibitory oligonucleotide was introduced at a specific ratio compared to its corresponding PCR primer. The inhibitory oligonucleotide was designed to be identical to the PCR primer with an additional 5 bp non-hybridizing 3' end. The inhibitory oligonucleotide was also designed to have the same hybridization parameters as the corresponding PCR primer, but due to the 3' mismatching, amplification would be inhibited; thereby reducing the PCR efficiency of the targeted high copy number amplicons for total DNA (see FIG. 3). The effect of these inhibitory oligonucleotides increased during the PCR assay as the real primers were consumed while the number of inhibitory oligonucleotides remained constant. The ratio was thus optimized to a level where the total DNA markers generated a peak of identical height as the fetal specific marker peak.

Table 4 below presents the PCR primers and inhibitory oligonucleotides designed for the fetal DNA quantification assay.

TABLE 4

PCR Primers and Inhibitory Oligonucleotides

| Primer | Type | Sequence | SEQ ID NO | Length (bp) | Tm (° C.) |
|---|---|---|---|---|---|
| TBX3_FP | Meth | 5'-CTTTGTCTCTGCGTGCC CGG-3' | 1 | 20 | 66.9 |
| TBX3_RP | Meth | 5'-CGCATGGCCGGCGCCA GAGT-3' | 2 | 20 | 73.1 |
| SOX14_Fp | Meth | 5'-CCACGGAATCCCGGCTCTGT | 3 | 20 | 67.7 |
| SOX14_RP | Meth | 5'-CTTCCTAGTGTGAGAACC GGCAAC-3' | 4 | 24 | 66.2 |
| POP5_FP | Total | 5'-TTGGACCACCAGTTTAGAC TGAACTGTGAA-3' | 5 | 30 | 64.4 |
| POP5_RP | Total | 5'-AGTTGGGTAGGAGTGAGG TGGTATGGCTA-3' | 6 | 29 | 64.2 |
| APOE_FP | Total | 5'-TTGGAGACAGTTTCTCCTT CCCCAGAC-3' | 7 | 27 | 63.7 |
| APOE_RP | Total | 5'-AGTTGGCAGCAACGCAGC CCACAG-3' | 8 | 24 | 65.5 |
| UTY_FP | Chr. Y | 5'-TTTCGTGATATTGATGCCG CCCTTCCCATCGC-3' | 9 | 32 | 69.2 |
| UTY_RP | Chr. Y | 5'-TTTCGTGATATTGTCTGTG CTGGGTGTTTTTGCAG-3' | 10 | 35 | 67.6 |
| DDX3Y_FP | Chr. Y | 5'-TTTCGTGATATTCCAAGTTT CAAAAAATCCTGAGTCCAC AAT-3' | 11 | 42 | 66.5 |
| DDX3Y_RP | Chr. Y | 5'-TTTCGTGATATGACTTACT GCTCACTGAATTTTGGAGTC-3' | 12 | 39 | 65.3 |
| DIGctrl1_FP | Control | 5'-CTTCGATAAAAATGATTGCA CTCGTGCCCCTTCTTTCTT-3' | 13 | 39 | 64.2 |
| DIGctrl1_RP | Control | 5'-CTTCGATAAAAATGATTGAG GGGAACCCGGGAGGAT-3' | 14 | 36 | 66.3 |
| DIGctrl2_FP | Control | 5'-CTTCGATAAAAATGATTGGA CAGGCCTTTGCAACAAGGAT | 15 | 40 | 65.3 |
| DIGctrl2_RP | Control | 5'-CTTCGATAAAAATGATTGGC CTGTTAACCAACCGGGAG-3' | 16 | 38 | 64.4 |
| POP5_FP_Inhibitor | InHib | 5'-TTGGACCACCAGTTTAGAC TGAACTGTGAA*TACAC*-3' | 17 | 35 | 64.4 |
| POP5_RP_Inhibitor | InHib | 5'-TTGGGTAGGAGTGAGGTG GTATGGCTA*TCTGC*-3' | 18 | 34 | 64.2 |
| APOE_FP_Inhibitor | InHib | 5'-TTGGAGACAGTTTCTCCTT CCCCAGAC*ACTAT*-3' | 19 | 32 | 63.7 |
| APOE_RP_Inhibitor | InHib | 5'-TTGGCAGCAACGCAGCCC ACAG*CAATG*-3' | 20 | 29 | 65.5 |

Table 4: List of PCR primers and inhibitory oligonucleotides used in the fetal DNA quantification assay. Bold letters indicate non-hybridizing 5' tails and bold italic letters indicate non-hybridizing 3' inhibitor sequences.

Outline of the Reaction

The fetal DNA quantification assay provided herein involved three steps. Step 1: Digestion of the DNA sample was performed using methylation sensitive restriction enzymes in combination with exonucleases to eliminate any residual single stranded DNA. When the reaction was complete, the enzymes were inhibited and the DNA was denatured using a heating step. Step 2: Following digestion, a PCR mixture was added containing all the reagents necessary for amplification including primers, inhibitory oligonucleotides, competitors and polymerase. PCR was performed using a two step cycling for approximately 35 cycles. By using a lower number of cycles a minimum of bias was introduced in the multiplex reaction yet enough products were generated for accurate analysis with a large signal over noise. In some cases, a post PCR exonuclease step was performed. Step 3: Electrophoresis was performed using a high resolution, microfluidics (i.e. capillary)-based electrophoretic nucleic acid separation system. In some instances, each reaction was sampled three times to eliminate variation introduced in the analysis step. This three step fetal quantification assay allowed for high-throughput and minimal operator handling time, and generated a significant reduction in workload compared to other DNA quantification methods, such as, for example, MALDI-TOF based FQA (see FIG. 4 for a comparison of the two methods).

Assay Biochemistry and Protocols

Restriction Digest Reaction

Samples for analysis, whether from the model system or from plasma, were first subjected to DNA digestion using methylation sensitive restriction enzymes with a total reaction volume of 20 microliters, which included 10 microliters of reagents and 10 microliters of sample. Given the dilute nature of the circulating cell free (CCF) DNA, the digestion reaction and PCR were performed in 96-well plate format. This was chosen due to the low concentration of CCF DNA in plasma which is typically between 1000 and 2000 genomic copies per microliter, or 0.15-0.30 ng/microliter, which requires more volume of sample to meet a minimum practical target value outlined by the reagent manufacture of ~5 ng per reaction.

The digestion mixture was mixed as described in Table 5 below and distributed into a 96 well non-skirted plate and centrifuged. After centrifugation 10 microliters of DNA sample was added to each well and mixed by repeated pipetting. DNA digestion, enzyme inactivation and DNA denaturation was performed according to the parameters shown in Table 6.

TABLE 5

Restriction Digest Reagents

| Reagent | Supplier | Final Concentration [20 ul] | Volume (microliters) |
|---|---|---|---|
| Water | N/A | N/A | 2.2 |
| 10x PCR Buffer (contains 20 mM MgCl2) | Sequenom | 1.0x | 2.0 |
| MgCl2 (20 mM) | Sequenom | 3.5 mM | 1.6 |
| HhaI (20 U/microliter) | NEB | 0.5 U/microliter | 0.5 |
| HpaII (10 U/microliter) | NEB | 0.5 U/microliter | 1.0 |
| Exonuclease I | NEB | 0.5 U/microliter | 0.5 |
| | | Total Volume = | 10.0 microliters |

TABLE 6

Restriction Digest Reaction Protocol

| Temperature | Time | Cycles | Comments |
|---|---|---|---|
| 41° C. | 30 minutes | 1 | Digestion step |
| 98° C. | 10 minutes | 1 | Inactivation of RE/Denaturation of DNA |
| 4° C. | forever | 1 | Store reaction |

Polymerase Chain Reaction (PCR)

Amplification of non-digested DNA targets and the competitors was performed in the digestion plate following the addition of 20 microliters of PCR mixture. The PCR reagents and thermal cycler profile are each presented below in Table 7 and Table 8, respectively.

TABLE 7

PCR Reagent Protocol

| Reagent | Supplier | Final Concentration | Volume (microliters) |
|---|---|---|---|
| Water | N/A | N/A | 4.8 |
| 10x PCR Buffer (contains 20 mM MgCl2) | Sequenom | 1.0x | 2 |
| MgCl2 (20 mM) | Sequenom | 3.5 mM | 1.6 |
| dNTPs Mix (10 mM each) | Roche | 500 micromolar | 0.8 |
| Primer Mix | IDT | 0.1*/0.06**/0.04*** micromolar | 5.0 |
| 5 U/microliter Fast Start | Sequenom | 5 U/rxn | 0.8 |
| Competitor mix (Dilution 5) | IDT | 2000/200 copies | 0.25 |
| | | Total Volume = | 20.0 microliters |

*Methylation, Chromosome Y and Digestion Controls
**Total Markers
***Total Marker Inhibitors

TABLE 8

PCR Thermal Cycler Profile

| Temperature | Time | Cycles | Comments |
|---|---|---|---|
| 95° C. | 5 minutes | 1 | Fast Start Activation |
| 95° C. | 45 seconds | 35 | Denaturation |
| 68° C. | 30 seconds | | Annealing/Extension |
| 72° C. | 3 minutes | 1 | Final Extension |
| 4° C. | forever | 1 | Store reaction |

Post-PCR

Remnants of PCR primers were removed using Exonuclease I by addition of 5 microliters of Exonuclease I mixture directly into the PCR reaction tube. The purpose of this step was to prevent unspecific peaks generated from the primers and/or oligonucleotides to interfere with the electropherogram analysis. The exonuclease reagents and reaction protocol are each presented below in Table 9 and Table 10, respectively.

TABLE 9

Exonuclease Reagent Protocol

| Reagent | Supplier | Final Concentration [5 ul] | Volume (microliters) |
|---|---|---|---|
| Water | N/A | N/A | 4.0 |
| 10x PCR Buffer (contains 20 mM MgCl2) | Sequenom | 1.0x | 0.5 |
| MgCl2 (20 mM) | Sequenom | 3.5 mM | 0.4 |
| Exonuclease I | NEB | 0.4 U/microliter | 0.1 |
| | | Total Volume = | 5.0 microliters |

TABLE 10

Exonuclease Reaction Protocol

| Temperature | Time | Cycles | Comments |
|---|---|---|---|
| 41° C. | 20 minutes | 1 | Digestion step |
| 4° C. | forever | 1 | Store reaction |

Example 2

Detection of Multiple Amplicons Using Capillary Electrophoresis

Figures 5A, 5B:
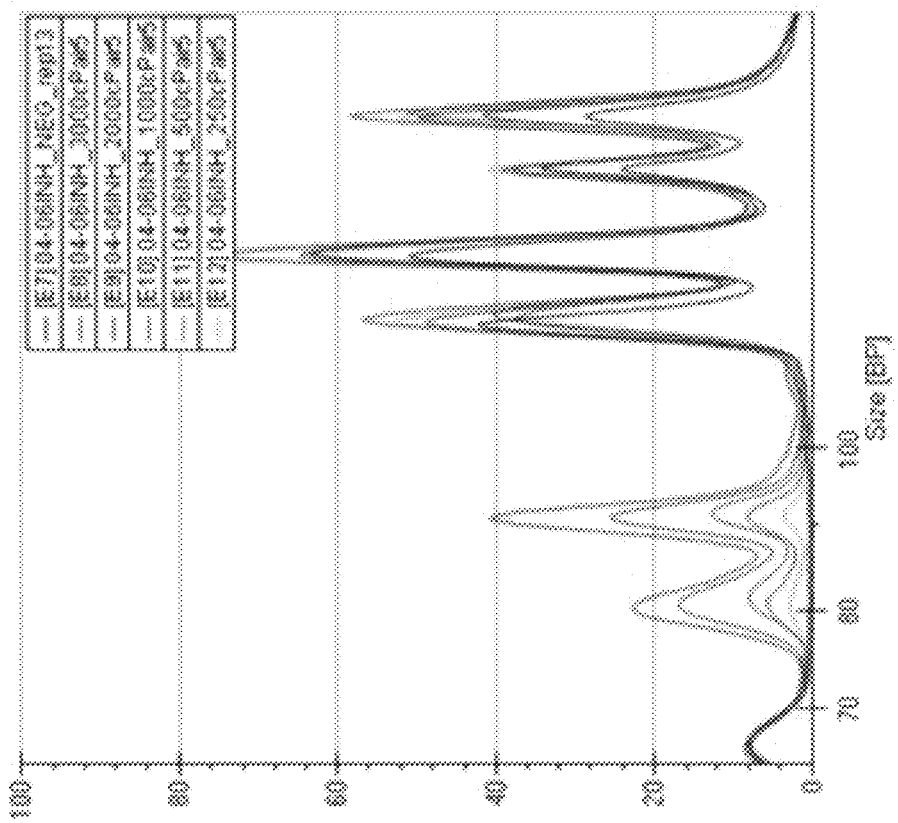
FIG. 5A and FIG. 5B show visualization of the fetal DNA quantification assay (FQA) amplicons using capillary electrophoresis. Genomic DNA samples made up of 80% nonmethylated DNA isolated from PBMCs and 20% placental DNA at various dilutions were used.

To determine the feasibility of quantification using a high resolution, microfluidics-based electrophoretic nucleic acid separation system (i.e. capillary electrophoresis), dilutions of genomic DNA were mixed in a ratio of 80% maternal nonmethylated DNA isolated from PBMCs and 20% of either male or female placental (fetal) DNA. Each sample was diluted to contain approximately 3000, 2000, 1000, 500, 250 or 0 total genomic copies with corresponding 600, 400, 200, 100, 50 and 0 methylated copies per reaction (see FIG. 5).

Using this assay assembly, the different amplicons were separated. No signal was detected for the Chromosome Y specific markers in female samples. The observed amplicon length was approximately 10 bp longer than the expected length using capillary electrophoresis. Possible explanations for this could be polyadenylation and/or a bulkier fragment due to dye binding. As the observation applied to all amplicons in the assay, there was no disruption in amplicon separation.

Example 3

Targeted Inhibitory PCR

Figure 6A:
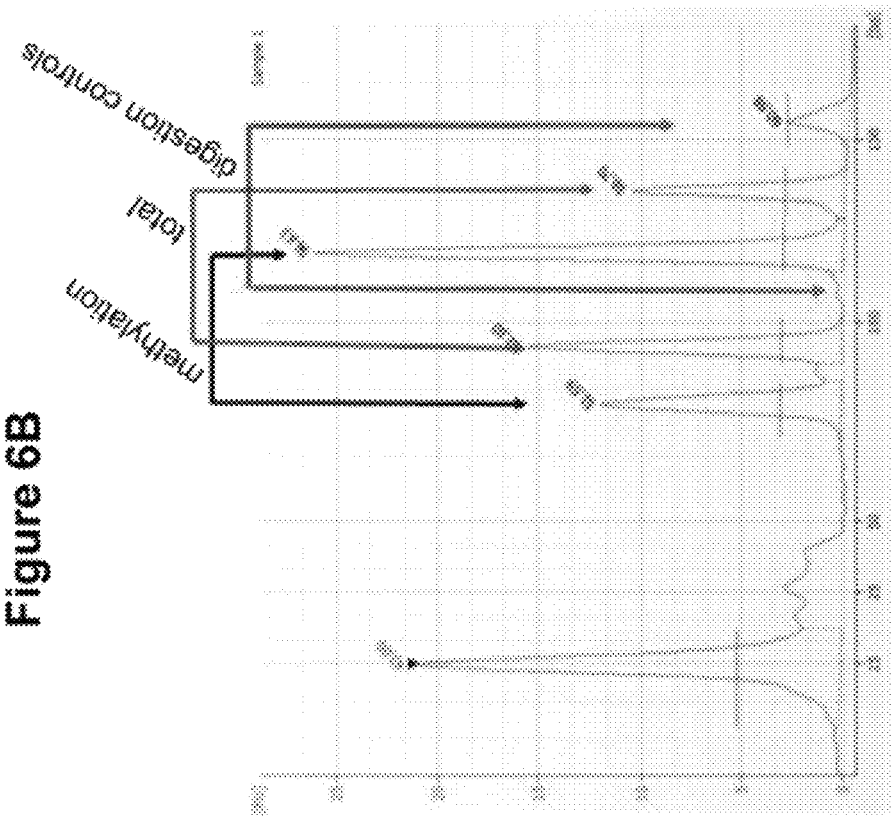
FIG. 6A and FIG. 6B show the effect of targeted inhibitory PCR. Two parallel reactions were performed using no inhibitors (FIG. 6A) or inhibitors in a ratio of 2:1 to the assays specific for total DNA markers (FIG. 6B). A significant reduction was observed for the targeted total marker (DNA template and competitive oligonucleotide) while no change was observed for the non-targeted assays.
Figure 6B:
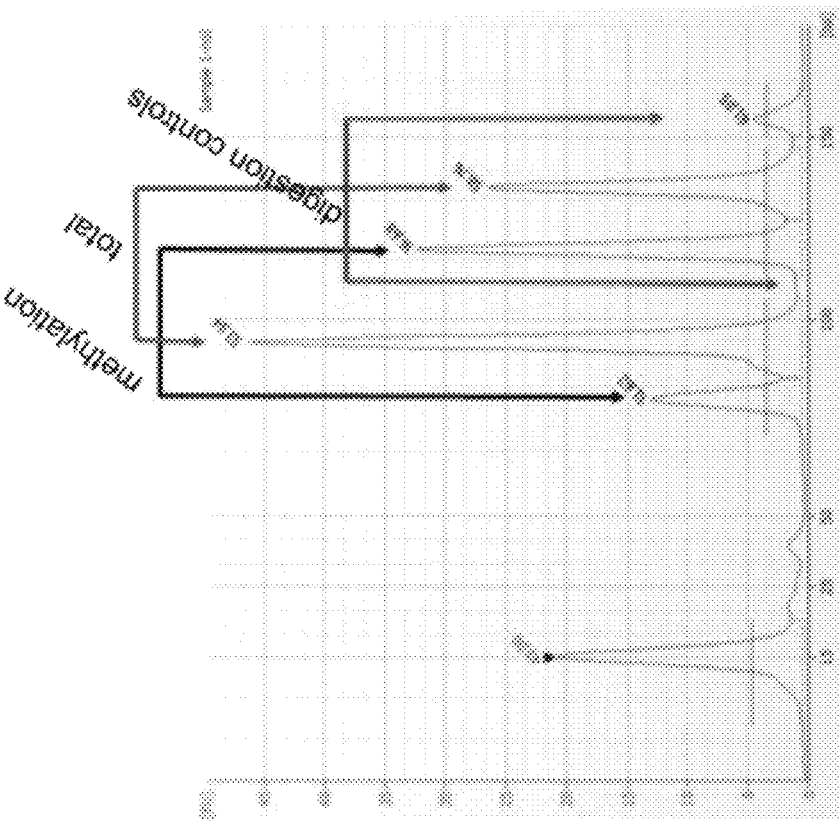

In this example, the effect of targeted inhibitory PCR was assayed. The results are shown in FIG. 6A and FIG. 6B. Two parallel reactions were performed using no inhibitors (FIG. 6A) or inhibitors in a ratio of 2:1 for the assays specific for total DNA markers (FIG. 6B). A significant reduction in amplification signal was observed for the targeted total marker (DNA template and competitive oligonucleotide) while no change was observed for the non-targeted assays.

Figure 7A:
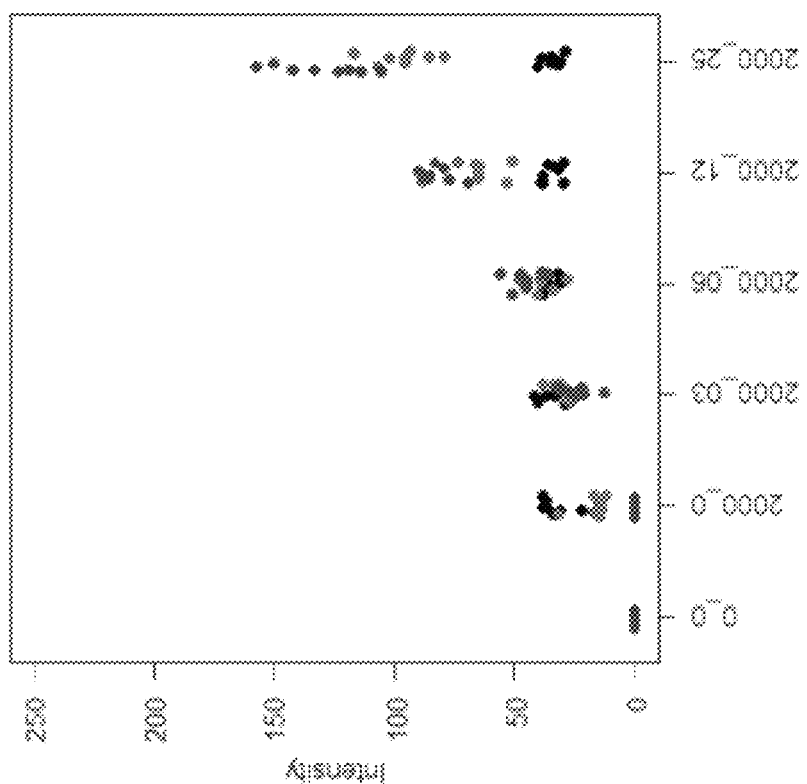
FIG. 7A and FIG. 7B show examples of targeted inhibitory PCR using different ratios of inhibitor versus PCR primer. Parallel reactions were performed using two different inhibitor/PCR primer ratios.
Figure 7B:
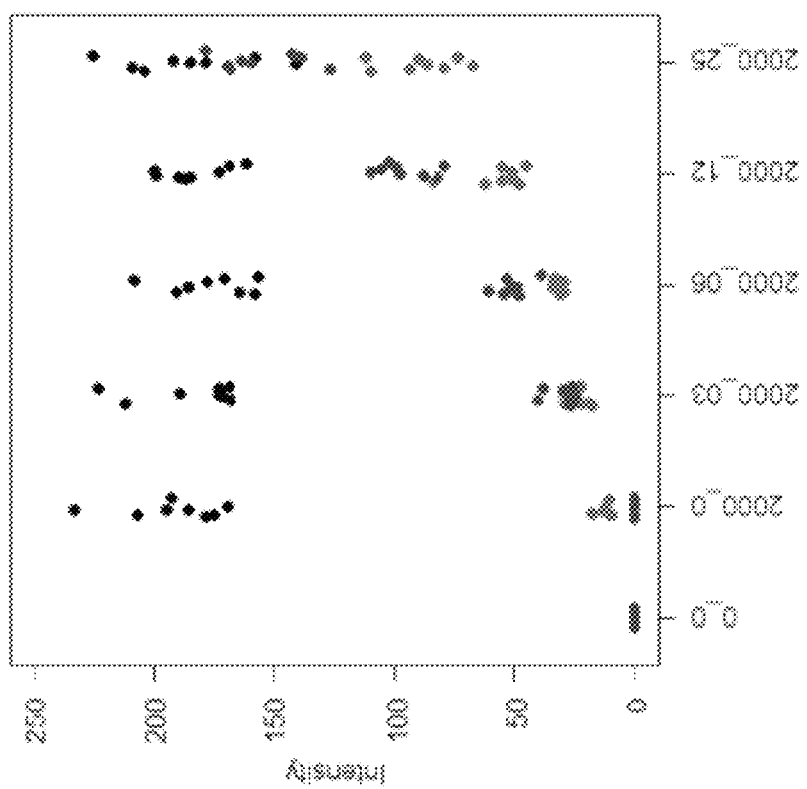

In another assay, targeted inhibitory PCR was performed using different ratios of inhibitor versus PCR primer. Parallel reactions were performed using two different inhibitor:PCR primer ratios. In FIG. 7A, a ratio of 0.4 micromolar inhibitor: 0.6 micromolar PCR primer was used. In FIG. 7B, a ratio of 0.6 micromolar inhibitor:0.4 micromolar PCR primer was used. While the intensity of the total markers was severely reduced with increased addition of inhibitors, no change was seen in the unaffected assays targeting methylation and Chromosome Y markers.

Example 4

Identification of PCR Primer Dimer Formation

Successful quantification of CCFF DNA depends on factors such as, for example, specificity and efficiency. Nonspecific products and inefficient primer association with target, for example, can affect the quality of the data. PCR primer design where the chosen primers are specific for the desired target sequence, bind at positions that avoid secondary structure, and minimize the occurrence of primer-dimer formation can lead to a successful CCFF DNA quantification assay. Appropriate reaction conditions can also improve the efficiency of amplification. Specificity and efficiency also can be addressed through, for example, optimization of the detection method, magnesium concentration, annealing temperature, enzyme concentration, PCR product length, etc.

Figure 8:
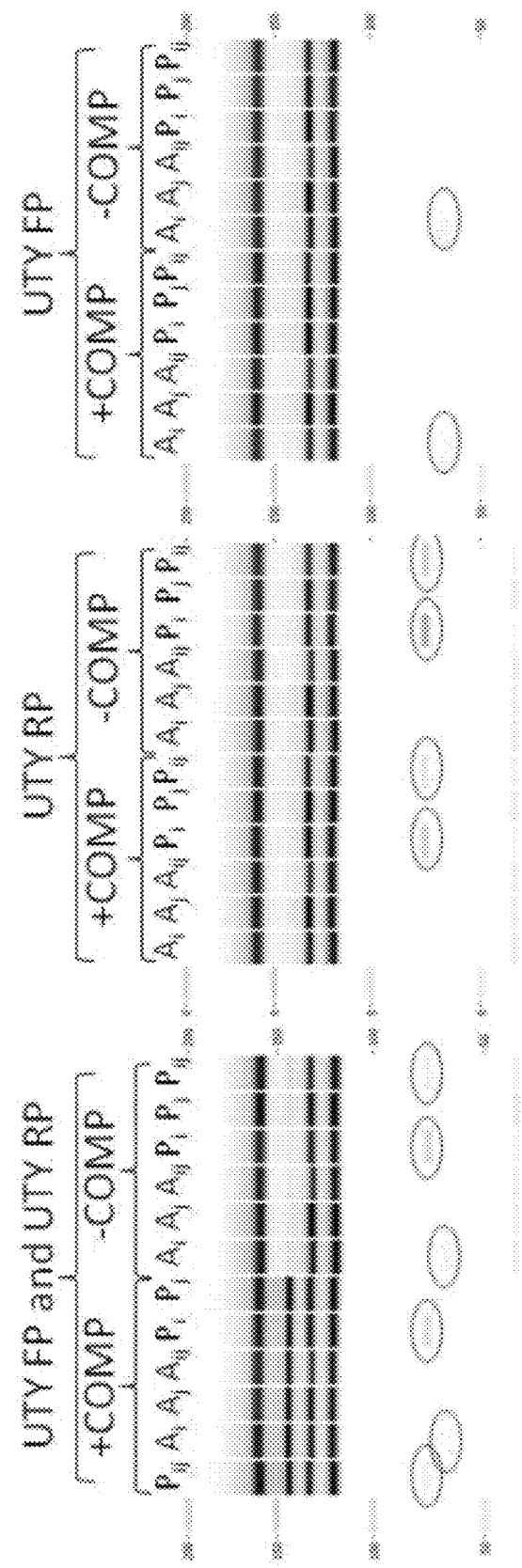
FIG. 8 shows the identification of primer dimer formation. Multiplex inhibitory PCR was performed using different combinations of PCR primers, inhibitor and competitor oligonucleotides. Different combinations of PCR primers and oligonucleotides were analyzed for primer dimer formation. By using the competitor as the only template for the PCR, four fragments at 115 bp, 126 bp, 141 bp and 156 bp were expected. Two template independent products were identified: 1) a 70 bp product generated from the interaction between the POP5 forward inhibitor with the UTY reverse primer and 2) a 60 bp product from the APOE forward inhibitor with the UTY forward primer. P=POP, A=APOE, i=Forward PCR primer only, j=Reverse PCR primer only, ij=Both Primers present.

To ensure sensitive and specific quantification of fetal DNA as well as robust and efficient amplification for both DNA and competitor oligonucleotides, a set of experiments were performed to identify potential primer-dimer formation. In this setup, the primer dimer potential of all PCR primers used was tested. The experiments included amplification with competitor oligonucleotides, inhibitor oligonucleotides, and forward primers and reverse primers only. Details for each experiment are presented below in Table 11, Table 12, and Table 13 below. By using the competitor as the only template for the PCR, four fragments at 115 bp, 126 bp, 141 bp and 156 bp were expected. As shown in FIG. 8, two template independent products were identified. The PCR primers specific to the UTY gene located on chromosome Y were identified to interact with the inhibitor oligonucleotides of the total markers. Specifically, the POP5 forward inhibitor interacted with the UTY reverse primer (generating a 70 bp product), and the APOE forward inhibitor interacted with the UTY forward primer (generating a 60 bp product), but only in the absence of the APOE reverse inhibitor. Each occurrence of primer dimer formation is circled in FIG. 8. Because of this primer dimer formation, the UTY PCR primers were removed from the fetal DNA quantification assay. Following the removal of UTY PCR primers, there was no sign of any primer dimer formation in the electropherogram.

TABLE 11

Primer Dimer Formation (FIG. 8, left panel)

| | 1 | 2 | 3 | 4 | 5 | 6 | 7 | 8 | 9 | 10 | 11 | 12 |
|---|---|---|---|---|---|---|---|---|---|---|---|---|
| DNA | − | − | − | − | − | − | − | − | − | − | − | − |
| Master mix | + | + | + | + | + | + | + | + | + | + | + | + |
| UTY Competitor | + | + | + | + | + | + | − | − | − | − | − | − |
| UTY Forward PCR primer | + | + | + | + | + | + | + | + | + | + | + | + |
| UTY Reverse PCR primer | + | + | + | + | + | + | + | + | + | + | + | + |
| Pop5 Forward inhibitor (Pi) | + | − | − | − | + | − | − | − | − | + | − | + |
| Pop5 Reverse inhibitor (Pj) | + | − | − | − | + | − | − | − | − | + | + | + |
| ApoE Forward inhibitor (Aj) | − | + | − | + | − | + | − | + | − | − | − | − |
| ApoE Reverse inhibitor (Aj) | − | − | + | + | − | − | − | + | + | − | − | − |
| Primer Dimer | + | + | − | − | + | − | + | − | − | + | − | + |

Table 11: Master mix includes PCR primers (FP and RP) for UTY; (FP and RP) for Tbx3, Sox14, Pop5, ApoE, Dig1 and Dig2. DDX3Y primers were omitted.

TABLE 12

Primer Dimer Formation (FIG. 8, middle panel)

| | 1 | 2 | 3 | 4 | 5 | 6 | 7 | 8 | 9 | 10 | 11 | 12 |
|---|---|---|---|---|---|---|---|---|---|---|---|---|
| DNA | − | − | − | − | − | − | − | − | − | − | − | − |
| Master mix | + | + | + | + | + | + | + | + | + | + | + | + |
| UTY Competitor | + | + | + | + | + | + | − | − | − | − | − | − |
| UTY Forward PCR primer | − | − | − | − | − | − | − | − | − | − | − | − |
| UTY | + | + | + | + | + | + | + | + | + | + | + | + |

TABLE 12-continued

Primer Dimer Formation (FIG. 8, middle panel)

|  | 1 | 2 | 3 | 4 | 5 | 6 | 7 | 8 | 9 | 10 | 11 | 12 |
|---|---|---|---|---|---|---|---|---|---|---|---|---|
| Reverse PCR primer Pop5 | – | – | – | + | – | + | – | – | – | + | – | + |
| Forward inhibitor Pop5 | – | – | – | – | + | + | – | – | – | – | + | + |
| Reverse inhibitor ApoE Forward inhibitor | + | – | + | – | – | – | + | – | + | – | – | – |
| ApoE Reverse inhibitor | – | + | + | – | – | – | + | + | – | – | – | – |
| Primer Dimer | – | – | – | + | – | + | – | – | – | + | – | + |

Table 12: Master mix includes PCR primers (RP) for UTY; (FP and RP) for Tbx3, Sox14, Pop5, ApoE, Dig1 and Dig2. DDX3Y primers were omitted.

TABLE 13

Primer Dimer Formation (FIG. 8, right panel)

|  | 1 | 2 | 3 | 4 | 5 | 6 | 7 | 8 | 9 | 10 | 11 | 12 |
|---|---|---|---|---|---|---|---|---|---|---|---|---|
| DNA | – | – | – | – | – | – | – | – | – | – | – | – |
| Master mix | + | + | + | + | + | + | + | + | + | + | + | – |
| UTY Competitor | + | + | + | + | + | + | – | – | – | – | – | – |
| UTY Forward PCR primer | + | + | + | + | + | + | + | + | + | + | + | + |
| UTY Reverse PCR primer | – | – | – | – | – | – | – | – | – | – | – | – |
| Pop5 Forward inhibitor | – | – | – | + | – | + | – | – | – | + | – | + |
| Pop5 Reverse inhibitor | – | – | – | – | + | + | – | – | – | – | + | + |
| ApoE Forward inhibitor | + | – | + | – | – | – | + | – | + | – | – | – |
| ApoE Reverse inhibitor | – | + | + | – | – | – | – | + | + | – | – | – |
| Primer Dimer | + | – | – | – | – | + | – | – | – | – | – | – |

Table 13: Master mix includes PCR primers (FP) for UTY; (FP and RP) for Tbx3, Sox14, Pop5 ApoE, Dig1 and Dig2. DDX3Y primers were omitted.

Example 5

Genomic Model System

Figure 9A:
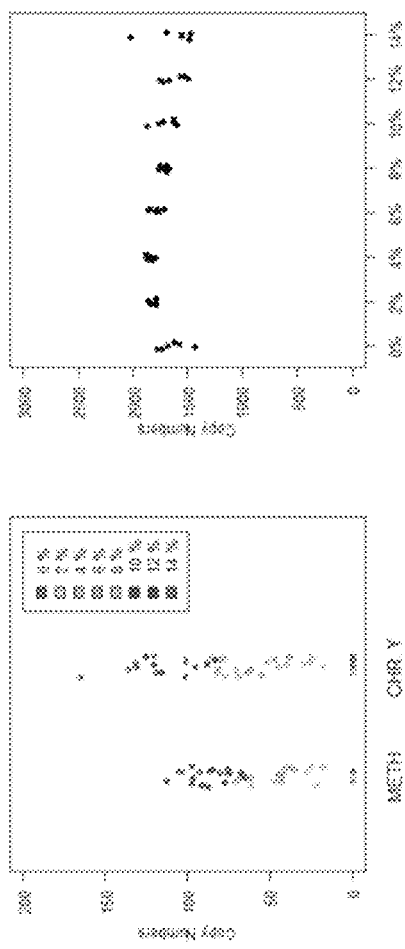
FIG. 9A, FIG. 9B, FIG. 9C and FIG. 9D show copy number quantification. DNA samples isolated from the blood of non-pregnant women mixed with different amounts of male placental DNA (0, 40, 80, 120, 160, 200, 240 and 280 copies). Each dilution was analyzed in six parallel reactions. Copy numbers were calculated using the ratio of each DNA/Competitor peak.
Figure 9B:
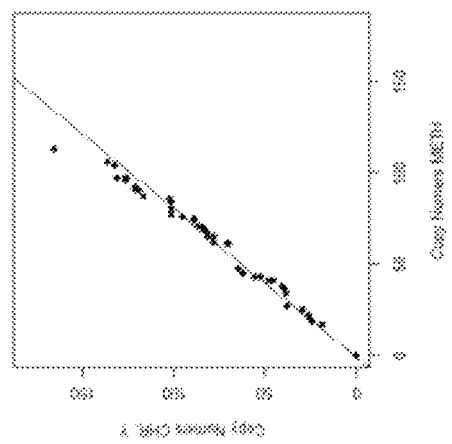
Figure 9C:
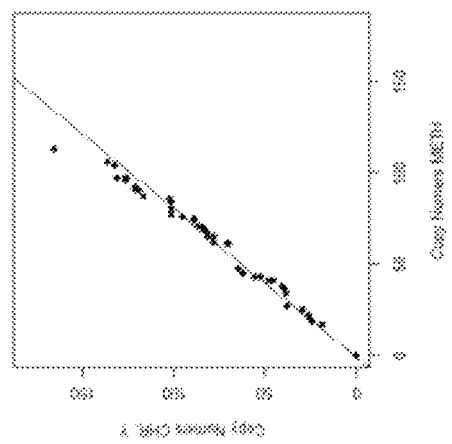
Figure 9D:
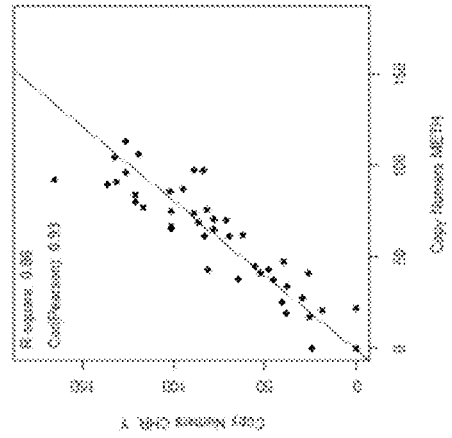

To determine the sensitivity and accuracy of the method, a model system was developed to simulate circulating cell free DNA samples isolated from plasma. The samples contained approximately 2000 genomic copies where the bulk was DNA isolated from maternal PBMC, and were spiked with different amounts of either male or female placental DNA. The samples were spiked with 0, 40, 80, 120, 160, 200, 240 or 280 placental copies generating samples with a placental fraction ranging from 0 to 14%. Each dilution was analyzed in six parallel reactions. Copy numbers were calculated using the ratio of each DNA marker/competitor peak. FIG. 9A presents a strip chart showing the calculated placental copy numbers using either the methylation or chromosome Y specific markers. The results indicate a correlation between placental fraction in the samples and the calculated copy number for a given peak for both methylation and Y specific markers. FIG. 9B presents a strip chart showing the calculated copy numbers for total DNA. Each dilution contained a constant total number of genomes, which was reflected in the calculated copy number values. As shown in FIG. 9C, a correlation between calculated copy numbers based on methylation markers and chromosome Y markers was observed. The copy numbers of placental DNA spiked into maternal non-methylated DNA in varying amounts was calculated by using the ratios obtained from the methylation assays and the Y-chromosome markers compared to the respective competitors. The model system showed high correlation between the methylation-based quantification and chromosome Y-specific sequences (rho=0.93 (Pearson correlation)). In FIG. 9D, a Q-Q plot comparing the calculated placental copy numbers using the methylation or chromosome Y markers is presented. A Q-Q plot ("Q" stands for quantile) is a probability plot, which is a graphical method for comparing two probability distributions by plotting their quantiles against each other. If the two distributions being compared are similar, the points in the Q-Q plot will approximately lie on the line y=x. If the distributions are linearly related, the points in the Q-Q plot will approximately lie on a line, but not necessarily on the line y=x. As shown in FIG. 9D, the two distributions lie on the y=x line, and thus were similar.

Example 6

CpG Methylated Model System

Figure 10:
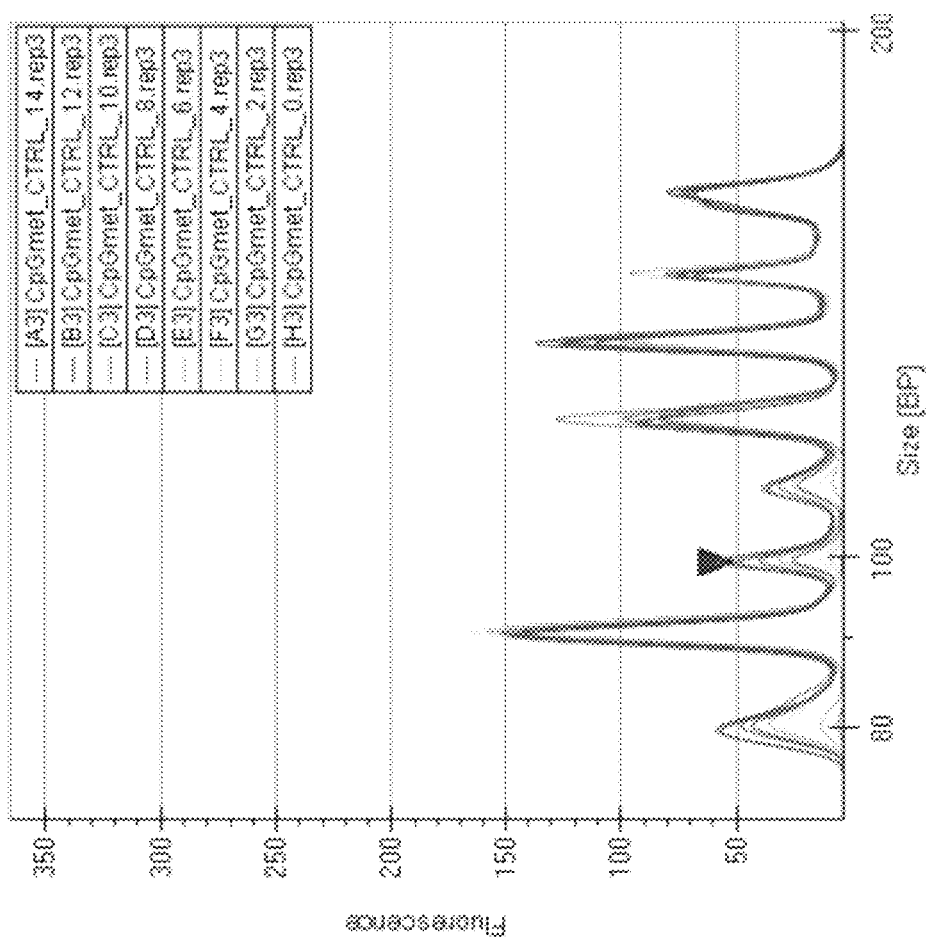
FIG. 10 shows the detection of CpG methylated DNA. A model system was developed to simulate degraded and circulating cell free DNA samples isolated from plasma. These samples contained approximately 2000 genomic copies where the bulk was DNA isolated from maternal PBMC to which different amounts of either male CpG methylated DNA were spiked. The samples were spiked with 0, 40, 80, 120, 160, 200, 240 or 280 placental copies generating samples with a placental fraction ranging from 0 to 14%. The arrowhead points to a peak generated by a 93 bp amplification product which corresponds to Y chromosome DNA.

To determine the sensitivity and accuracy of the digestion control, a model system was developed to simulate degraded and circulating cell free DNA samples isolated from plasma. These samples contained approximately 2000 genomic copies where the bulk was DNA isolated from maternal PBMC, and were spiked with different amounts of male CpG methylated DNA. The samples were spiked with 0, 40, 80, 120, 160, 200, 240 or 280 placental copies generating samples with a placental fraction ranging from 0 to 14%. As shown in FIG. 10, a distinct peak was seen at approximately 110 bp in all samples where CpG methylated DNA was spiked into the reaction. As all DNA was methylated in the spiked in DNA, the restriction was incomplete and the peak generated could be quantified. The peak heights obtained for the digestion control showed linearity with the methylation peak and the chromosome Y peak thereby validating the digestion controls.

Example 7

Plasma-Derived DNA

Figure 16:
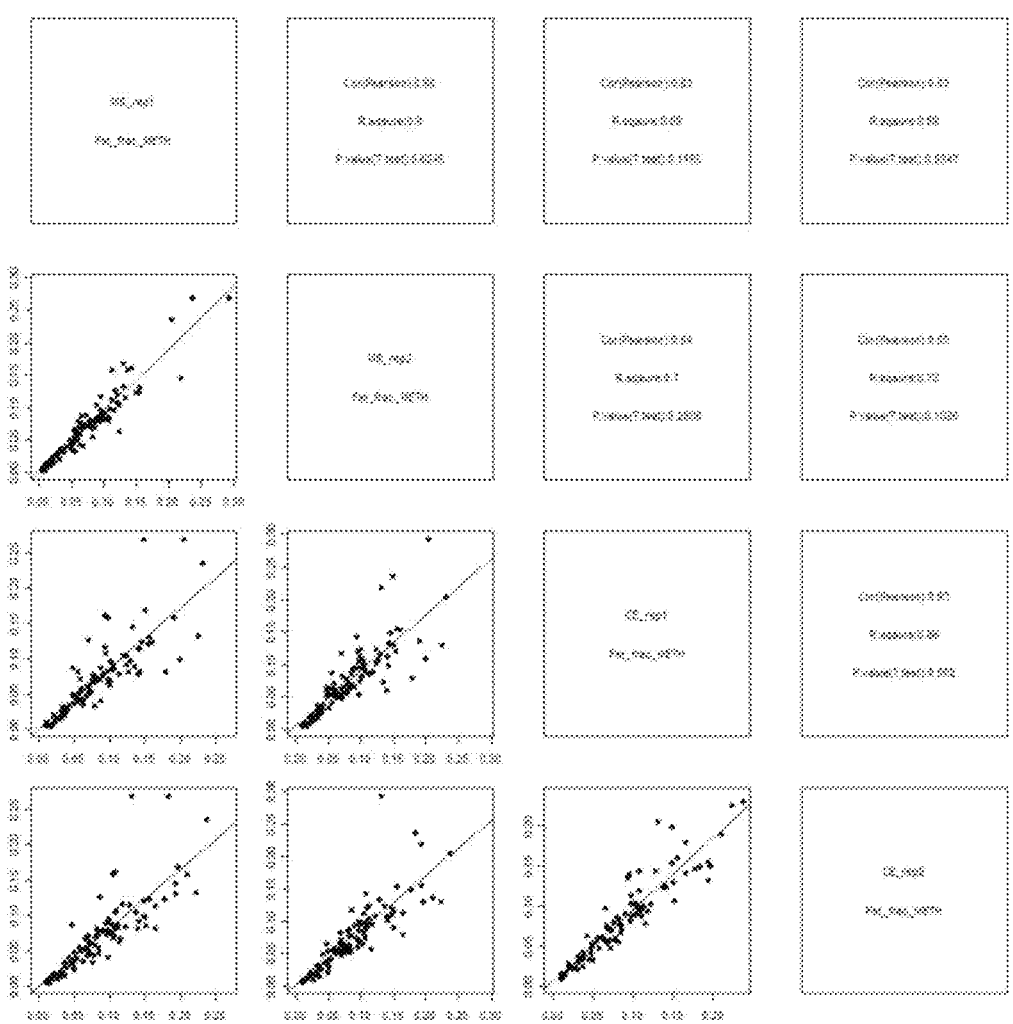
FIG. 16 show a correlation plots for the minority species copy numbers obtained using either the MASSARRAY or capillary electrophoresis method. Each sample was analyzed in duplicate for each method. All correlation coefficients were above 0.9 using Pearson correlation indicating very good correlation between both methods and replicates. A paired T.test generated p-values indicating no significant different between the methods.
Figure 17:
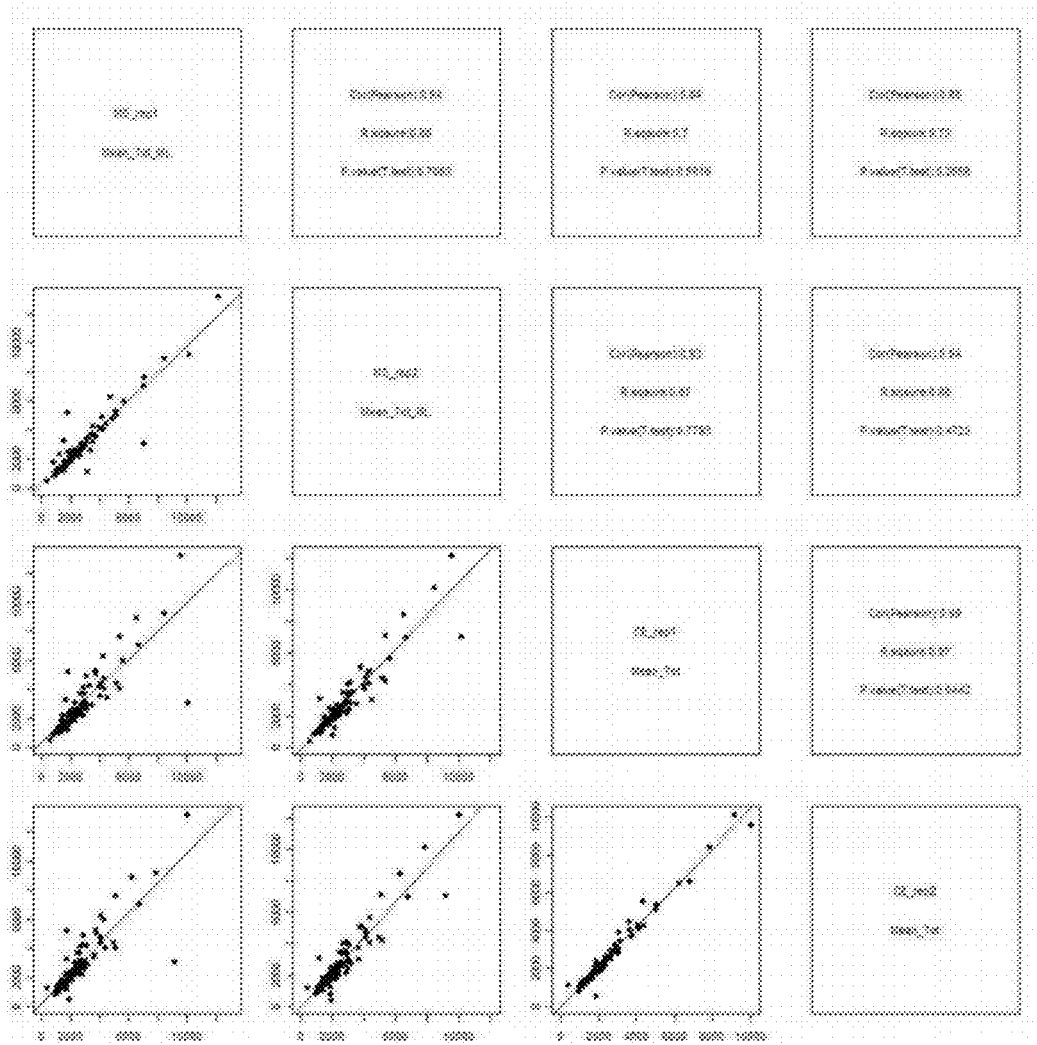
FIG. 17 shows correlation plots for the minority species copy numbers obtained using either the MASSARRAY or capillary electrophoresis method. Each sample was analyzed in duplicate for each method. A paired T.test generated p-values above 0.05 indicating no significant different between the methods.

To investigate the sensitivity and accuracy of the methods for fetal DNA quantification in clinical samples, 96 plasma samples obtained from pregnant women were analyzed. The DNA samples which were obtained from 4 ml extractions were eluted in 55 microliters and used in four parallel reactions: two reactions for Capillary Based FQA and two reactions using a MassARRAY based FQA. The results obtained with the capillary electrophoresis-based FQA provided herein were compared to the MASSARRAY based FQAs. Paired correlation between the calculated copy numbers and minority fractions obtained using the mean of the methylation markers and total DNA were calculated. The given values indicated minimal difference between the two different measurements, thus validating the accuracy and stability of the method (see FIGS. 16 and 17).

Figure 11:
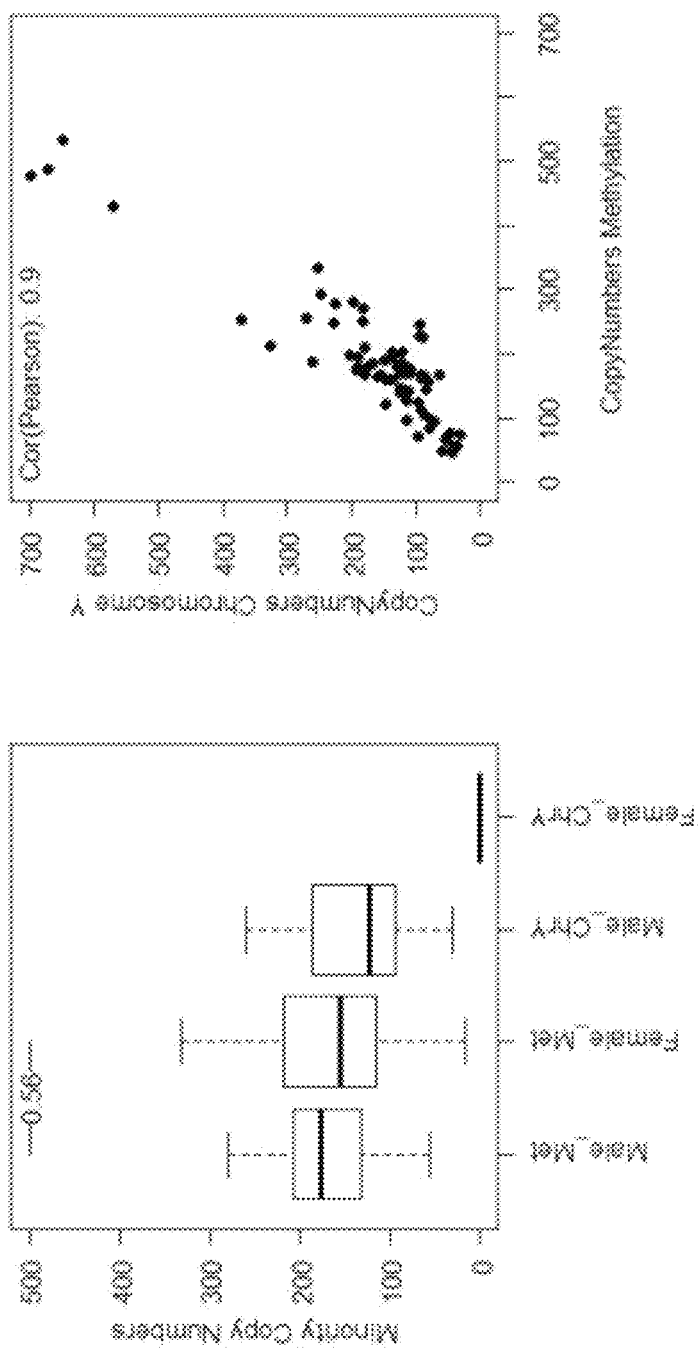
FIG. 11A shows a comparison between male and female pregnancies. A box plot of the fetal fraction of male versus female DNA samples obtained in DNA samples isolated from 96 pregnant women is presented. The upper and lower whiskers represent the 5th and 95th percentiles. The upper, middle, and lower bars represent the 25th, 50th, 75th percentiles. No significant difference was observed between male (n=36) and female (n=60) samples for the methylation markers (p-value greater than 0.05.
FIG. 11B presents a paired correlation between the calculated fetal copy numbers obtained using the methylation markers versus the Y-chromosome markers for the male samples. The given values indicated minimal difference between the two different measurements, thus validating the accuracy and stability of the method. (p=0.9, Pearson correlation).
Figure 12:
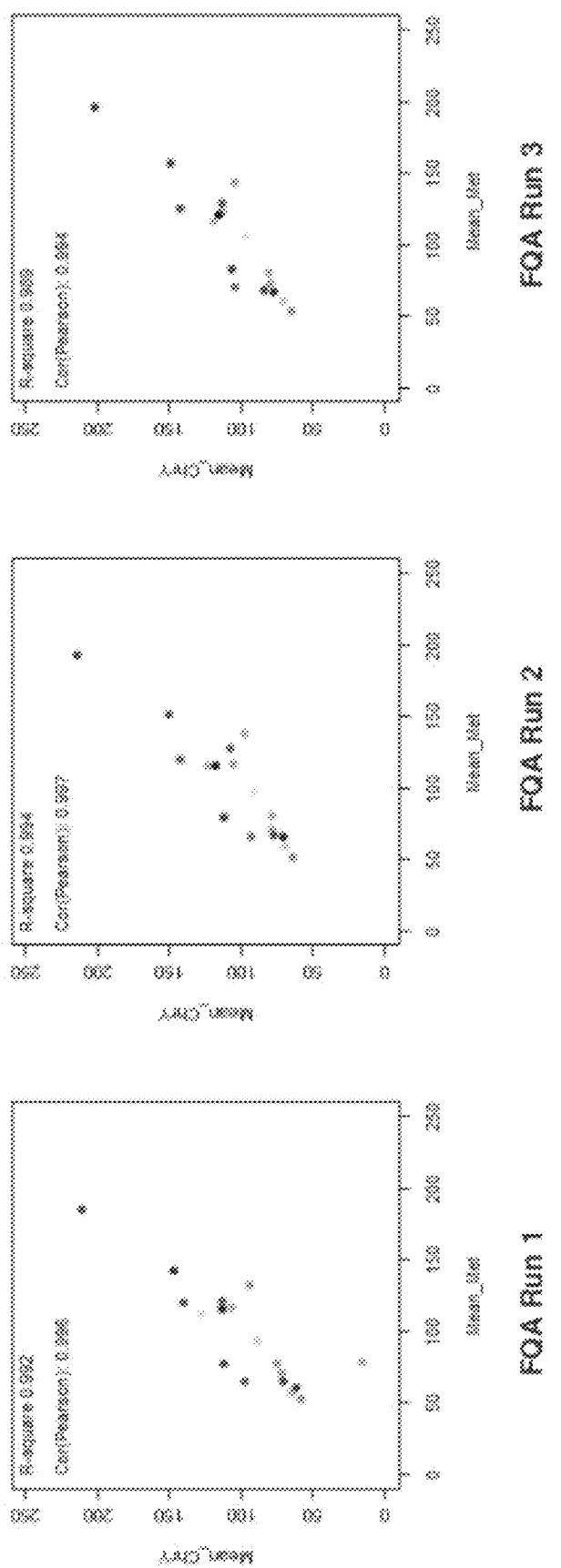
FIG. 12 shows a comparison between three consecutive FQA runs using capillary electrophoresis. Paired correlation between the calculated fetal fractions obtained using the mean of the methylation markers versus the mean from the Y-chromosome markers for the male samples is shown. The given values indicated minimal difference between the three different measurements, thus validating the accuracy and stability of the method.

The data was analyzed as shown in FIG. 11 and FIG. 12. As shown in FIG. 11A, a comparison was made between male and female pregnancies. A box plot of the fetal fraction of male versus female DNA samples (of the 96 DNA samples) was generated. The upper and lower whiskers represent the 5th and 95th percentiles. The upper, middle, and lower bars represent the 25th, 50th, 75th percentiles. No significant difference was observed between male (n=36) and female (n=60) samples for the methylation markers (p-value>0.05). FIG. 11B presents a paired correlation between the calculated fetal copy numbers obtained using the methylation markers versus the Y-chromosome markers for the male samples. The given values indicated minimal difference between the two different measurements, thus validating the accuracy and stability of the method. (p=0.9, Pearson correlation).

Additional analysis of the data above included a comparison of three consecutive capillary electrophoresis runs. The results are presented in FIG. 12. Paired correlation between the calculated fetal fractions obtained using the mean of the methylation markers versus the mean from the Y-chromosome markers for the male samples is shown. The given values indicated minimal difference between the three different measurements, thus validating the accuracy and stability of the method.

Example 8

Post PCR Optimization

In this example, electrophoresis was used to visualize and quantify the multiple amplicons generated in the PCR and identify any nonspecific peaks in the electropherogram. Since the specificity of the assay is dependent on the PCR primers, novel structures such as primer-dimer formation and non-specific amplification of either genomic DNA present in the reaction or the competitor oligonucleotide can lead to noise in the electropherogram. A clean electropherogram containing only the expected peaks can provide a more reassuring impression than an electropherogram containing unspecific peaks.

Figure 13A:
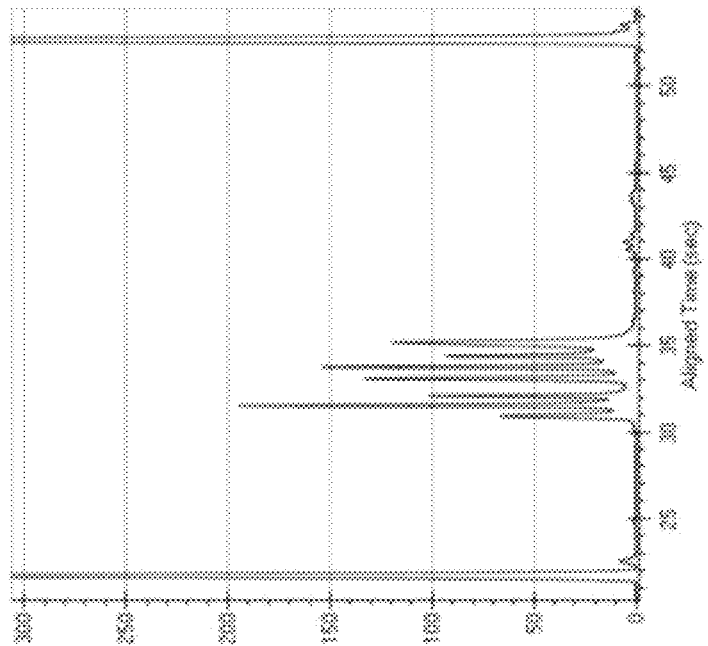
FIG. 13A and FIG. 13B shows the results of post PCR treatment with Exonuclease I. The FQA assay was performed in duplicate and analyzed using capillary electrophoresis.
Figure 13B:
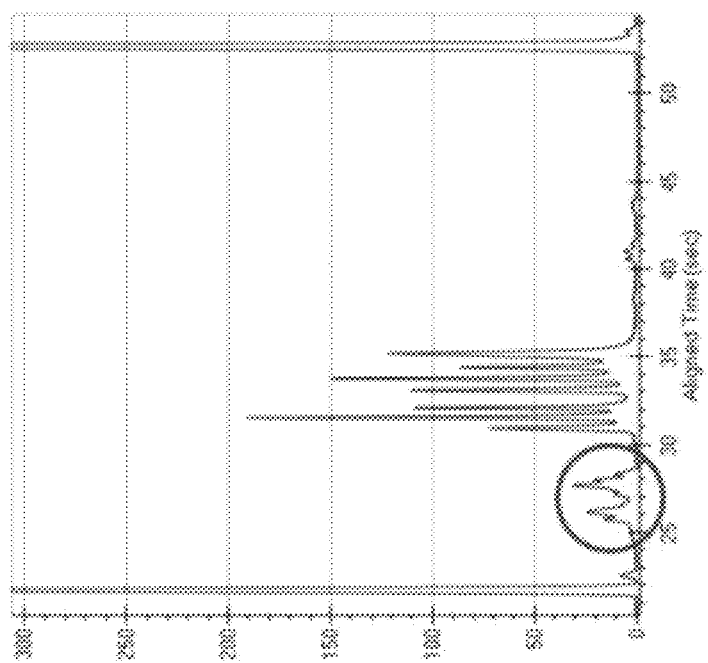

As shown in FIG. 13A, nonspecific peaks corresponding to the PCR primers were detected in the electropherogram (circled in FIG. 13A). To remove all remaining single stranded PCR primers the post-PCR sample was treated with 2.5 U Exonuclease I for 15 minutes at 41° C. The assay was performed in duplicate. As shown in FIG. 13B, the exonuclease removed all PCR primers. Furthermore, because the annealing/elongation step of the PCR is performed at 68° C. the specificity of the PCR primers is excellent and no primer dimers were formed. These structures, if they were present, would be readily identified in the electropherogram because they are double stranded and would escape the single strand specific exonuclease.

Example 9

Calculation of Fraction and Copy Number of a Minority Nucleic Acid

To demonstrate a determination of minority nucleic acid fractions using the capillary-based FQA, mixed samples with predetermined ratios of minority to majority nucleic acid were used. Minority fractions based SOX14 and TBX3 methylation markers in mixed DNA samples containing 0 to 10% minority species were determined. Each sample contained either 1500 or 3000 total copies (minority and majority) in the following ratios: 0%:100%, 1%:99%, 2%:98%, 3%:97%, 4%:96%, 5%:95%, 6%:94%, 7%:93%, 8%:92%, 9%:91%, and 10%:90% minority to majority. To calculate the fraction of the minority nucleic acid in the sample relative to the total amount of the nucleic acid in the sample, the following equation was applied:

The fraction of minority nucleic acid=(Concentration of the minority nucleic acid)/[(Concentration of total nucleic acid)×k)], where k is the damping coefficient by which the majority nucleic acid amplification product is modulated. K was determined experimentally based on the ratio of total primers to inhibitor used in the amplification reaction. The concentrations of the total and minority nucleic acid species were obtained in a readout generated by capillary electrophoresis. Each sample was analyzed using the capillary-based FQA assay in 8 replicates and the results are shown in FIG. 14A (1500 total copies) and FIG. 14B (3000 total copies). The expected minority fractions correlated well with the observed minority fractions for each type of sample.

To demonstrate a determination of minority nucleic acid copy number using the capillary-based FQA, mixed samples with predetermined copy numbers of minority nucleic acid were used. Minority copy numbers based SOX14 and TBX3 methylation markers in DNA samples containing 0 to 10% minority species (i.e. 0 to 150 minority species copies in FIG. 15A and 0 to 300 minority species copies in FIG. 15B) were determined. Each sample contained either 1500 or 3000 total copies (minority and majority) in the following ratios: 0%:100%, 1%:99%, 2%:98%, 3%:97%, 4%:96%, 5%:95%, 6%:94%, 7%:93%, 8%:92%, 9%:91%, and 10%:90% minority to majority. To calculate the copy number of the minority nucleic acid in the sample, the following equation was applied:

Copy number (minority nucleic acid species)=[(Concentration of the minority nucleic acid)/(Concentration of the minority competitor)]×C, where C is the number of competitor oligonucleotides added to the amplification reaction. The concentrations of the minority nucleic acid and minority competitor were obtained in a readout generated by capillary electrophoresis. Each sample was analyzed using the capillary-based FQA assay in 8 replicates and the results are shown in FIG. 15A (1500 total copies) and FIG. 15B (3000 total copies). The expected minority copy numbers correlated well with the observed minority copy numbers for each type of sample.

Example 10

Differentially Methylated Genomic Regions

In this example, additional genomic DNA targets for the determination of methylated or unmethylated nucleic acid are presented. The regions listed in Table 14 (non-chromosome 21 regions) and Table 15 (chromosome 21 regions) below exhibit different levels of DNA methylation in a significant portion of the examined CpG dinucleotides within the defined region and are thus described as being differentially methylated regions (DMR) when comparing DNA derived from placenta tissue and peripheral blood mononuclear cells (PBMC). Differential DNA methylation of CpG sites was determined using a paired T Test with those sites considered differentially methylated if the p-value when comparing placental tissue to PBMC is p<0.05. The definition of each column is listed below.

Region Name: Each region is named by the gene(s) residing within the area defined or nearby. Regions where no gene name is listed but rather only contain a locus have no refseq genes in near proximity.

Gene Region: For those regions contained either in close proximity to or within a gene, the gene region further explains the relationship of this region to the nearby gene.

Chrom: The chromosome on which the DMR is located using the hg18 build of the UCSC genome browser (World Wide Web URL genome.ucsc.edu).

Start: The starting position of the DMR as designated by the hg18 build of the UCSC genome browser World Wide Web URL genome.ucsc.edu).

End: The ending position of the DMR as designated by the hg18 build of the UCSC genome browser (World Wide Web URL genome.ucsc.edu).

Microarray Analysis: Describes whether this region was also/initially determined to be differentially methylated by microarray analysis. The methylated fraction of ten paired placenta and PBMC samples was isolated using the MBD-Fc protein. The two tissue fractions were then labeled with either ALEXA FLUOR 555-aha-dCTP (PBMC) or ALEXA FLUOR 647-aha-dCTP (placental) using the BioPrime Total Genomic Labeling System™ and hybridized to Agilent® CpG Island microarrays. Many regions examined in these studies were not contained on the initial microarray.

EPITYPER 8 Samples: Describes whether this region was analyzed and determined to be differentially methylated in eight paired samples of placenta and peripheral blood mononuclear cells (PBMC) using EPITYPER technology. Regions that were chosen for examination were based on multiple criteria. First, regions were selected based on data from the Microarray Analysis. Secondly, a comprehensive examination of all CpG islands located on chromosome 21 was undertaken. Finally, selected regions on chromosome 21 which had lower CpG frequency than those located in CpG islands were examined.

EPITYPER 73 Samples: Describes whether this region was subsequently analyzed using EPITYPER technology in a sample cohort consisting of 73 paired samples of placenta and PBMC. All regions selected for analysis in this second sample cohort were selected on the basis of the results from the experimentation described in the EPITYPER 8 column. All regions in this additional cohort exhibited a methylation profile similar to that determined in the EPITYPER 8 Samples analysis.

Previously Validated EPITYPER: Describes whether this region or a portion of this region was validated using EPITYPER during previous experimentation.

Relative Methylation Placenta to Maternal: Describes the direction of differential methylation. Regions labeled as "hypermethylation" are more methylated within the designated region in placenta samples relative to PBMC and "hypomethylation" are more methylated within the designated region in PBMC samples.

Region Length (bp): Length of the DMR using the hg18 build of the UCSC genome browser (World Wide Web URL genome.ucsc.edu).

TABLE 14

Differentially Methylated Genomic Regions (non-Chromosome 21)

| Region Name | Gene Region | Chrom | Start | End | Microarray Analysis | EPITYPER 8 Samples | EPITYPER 73 Samples | Previously Validated EPITYPER | Relative Methylation Placenta to Maternal | Region Length (bp) |
|---|---|---|---|---|---|---|---|---|---|---|
| TFAP2E | Intron | chr1 | 35815000 | 35816200 | YES | YES | NO | NO | Hypermethylation | 1200 |
| LRRC8D | Intron/Exon | chr1 | 90081350 | 90082250 | YES | YES | NO | NO | Hypermethylation | 900 |
| TBX15 | Promoter | chr1 | 119333500 | 119333700 | YES | YES | NO | NO | Hypermethylation | 200 |
| C1orf51 | Upstream | chr1 | 148520900 | 148521300 | YES | YES | NO | NO | Hypermethylation | 400 |
| chr1: 179553900-179554600 | Intergenic | chr1 | 179553900 | 179554600 | YES | YES | NO | NO | Hypermethylation | 700 |
| ZFP36L2 | Exon | chr2 | 43304900 | 43305100 | YES | YES | NO | NO | Hypermethylation | 200 |
| SIX2 | Downstream | chr2 | 45081000 | 45086000 | YES | YES | NO | YES | Hypermethylation | 5000 |
| chr2: 137238500-137240000 | Intergenic | chr2 | 137238500 | 137240000 | YES | YES | NO | NO | Hypermethylation | 1500 |
| MAP1D | Intron/Exon | chr2 | 172652800 | 172653600 | YES | YES | NO | NO | Hypermethylation | 800 |
| WNT6 | Intron | chr2 | 219444250 | 219444290 | YES | YES | NO | NO | Hypermethylation | 40 |
| INPP5D | Promoter | chr2 | 233633200 | 233633700 | YES | YES | YES | NO | Hypermethylation | 500 |
| chr2: 241211100-241211600 | Intergenic | chr2 | 241211100 | 241211600 | YES | YES | YES | NO | Hypermethylation | 500 |
| WNT5A | Intron | chr3 | 55492550 | 55492850 | YES | YES | NO | NO | Hypermethylation | 300 |
| chr3: 138971600-138972200 | Intergenic | chr3 | 138971600 | 138972200 | YES | YES | YES | YES | Hypermethylation | 600 |
| ZIC4 | Intron | chr3 | 148598200 | 148599000 | YES | YES | NO | NO | Hypermethylation | 800 |
| FGF12 | Intron/Exon | chr3 | 193608500 | 193610500 | YES | YES | NO | NO | Hypermethylation | 2000 |
| GP5 | Exon | chr3 | 195598400 | 195599200 | YES | YES | NO | NO | Hypermethylation | 800 |
| MSX1 | Upstream | chr4 | 4910550 | 4911100 | YES | YES | NO | NO | Hypermethylation | 550 |
| NKX3-2 | Intron/Exon | chr4 | 13152500 | 13154500 | YES | YES | NO | NO | Hypermethylation | 2000 |
| chr4: 111752000-111753000 | Intergenic | chr4 | 111752000 | 111753000 | YES | YES | YES | NO | Hypermethylation | 1000 |
| SFRP2 | Promoter | chr4 | 154928800 | 154930100 | YES | YES | NO | NO | Hypermethylation | 1300 |
| chr4: 174664300-174664800 | Intergenic | chr4 | 174664300 | 174664800 | YES | YES | NO | NO | Hypermethylation | 500 |
| chr4: 174676300-174676800 | Intergenic | chr4 | 174676300 | 174676800 | YES | YES | NO | NO | Hypermethylation | 500 |
| SORBS2 | Intron | chr4 | 186796900 | 186797500 | YES | YES | NO | NO | Hypermethylation | 600 |
| chr5: 42986900-42988200 | Intergenic | chr5 | 42986900 | 42988200 | YES | YES | NO | NO | Hypermethylation | 1300 |
| chr5: 72712000-72714100 | Intergenic | chr5 | 72712000 | 72714100 | YES | YES | NO | NO | Hypermethylation | 2100 |
| chr5: 72767550-72767800 | Intergenic | chr5 | 72767550 | 72767800 | YES | YES | NO | NO | Hypermethylation | 250 |
| NR2F1 | Intron/Exon | chr5 | 92955000 | 92955250 | YES | YES | NO | NO | Hypermethylation | 250 |

TABLE 14-continued

Differentially Methylated Genomic Regions (non-Chromosome 21)

| Region Name | Gene Region | Chrom | Start | End | Microarray Analysis | EPI-TYPER 8 Samples | EPI-TYPER 73 Samples | Previously Validated EPI-TYPER | Relative Methylation Placenta to Maternal | Region Length (bp) |
|---|---|---|---|---|---|---|---|---|---|---|
| PCDHGA1 | Intron | chr5 | 140850500 | 140852500 | YES | YES | YES | NO | Hypermethylation | 2000 |
| chr6: 10489100-10490200 | Intergenic | chr6 | 10489100 | 10490200 | YES | YES | YES | NO | Hypermethylation | 1100 |
| FOXP4 | Intron | chr6 | 41636200 | 41637000 | YES | YES | NO | YES | Hypermethylation | 800 |
| chr7: 19118400-19118700 | Intergenic | chr7 | 19118400 | 19118700 | YES | YES | NO | NO | Hypermethylation | 300 |
| chr7: 27258000-27258400 | Intergenic | chr7 | 27258000 | 27258400 | YES | YES | NO | NO | Hypermethylation | 400 |
| TBX20 | Upstream | chr7 | 35267500 | 35268300 | YES | YES | NO | NO | Hypermethylation | 800 |
| AGBL3 | Promoter | chr7 | 134321300 | 134322300 | YES | YES | NO | NO | Hypermethylation | 1000 |
| XPO7 | Downstream | chr8 | 21924000 | 21924300 | YES | YES | NO | NO | Hypermethylation | 300 |
| chr8: 41543400-41544000 | Intergenic | chr8 | 41543400 | 41544000 | YES | YES | NO | NO | Hypermethylation | 600 |
| GDF6 | Exon | chr8 | 97225400 | 97227100 | YES | YES | NO | NO | Hypermethylation | 1700 |
| OSR2 | Intron/Exon | chr8 | 100029000 | 100031000 | YES | YES | YES | YES | Hypermethylation | 2000 |
| GLIS3 | Intron/Exon | chr9 | 4288000 | 4290000 | YES | YES | NO | YES | Hypermethylation | 2000 |
| NOTCH1 | Intron | chr9 | 138547600 | 138548400 | YES | YES | YES | NO | Hypermethylation | 800 |
| EGFL7 | Upstream | chr9 | 138672350 | 138672850 | YES | YES | NO | NO | Hypermethylation | 500 |
| CELF2 | Intron/Exon | chr10 | 11246700 | 11247900 | YES | YES | NO | NO | Hypermethylation | 1200 |
| HHEX | Intron | chr10 | 94441000 | 94441800 | YES | YES | NO | NO | Hypermethylation | 800 |
| DOCK1/FAM196A | Intron/Exon | chr10 | 128883000 | 128883500 | YES | YES | NO | NO | Hypermethylation | 500 |
| PAX6 | Intron | chr11 | 31782400 | 31783500 | YES | YES | NO | NO | Hypermethylation | 1100 |
| FERMT3 | Intron/Exon | chr11 | 63731200 | 63731700 | YES | YES | YES | NO | Hypermethylation | 500 |
| PKNOX2 | Intron | chr11 | 124541200 | 124541800 | YES | YES | NO | NO | Hypermethylation | 600 |
| KIRREL3 | Intron | chr11 | 126375150 | 126375300 | YES | YES | NO | NO | Hypermethylation | 150 |
| BCAT1 | Intron | chr12 | 24946700 | 24947600 | YES | YES | NO | NO | Hypermethylation | 900 |
| HOXC13 | Intron/Exon | chr12 | 52625000 | 52625600 | YES | YES | NO | NO | Hypermethylation | 600 |
| TBX5 | Promoter | chr12 | 113330500 | 113332000 | YES | YES | NO | NO | Hypermethylation | 1500 |
| TBX3 | Upstream | chr12 | 113609000 | 113609500 | YES | YES | NO | YES | Hypermethylation | 500 |
| chr12: 113622100-113623000 | Intergenic | chr12 | 113622100 | 113623000 | YES | YES | YES | NO | Hypermethylation | 900 |
| chr12: 113657800-113658300 | Intergenic | chr12 | 113657800 | 113658300 | YES | YES | NO | NO | Hypermethylation | 500 |
| THEM233 | Promoter | chr12 | 118515500 | 118517500 | YES | YES | NO | YES | Hypermethylation | 2000 |
| NCOR2 | Intron/Exon | chr12 | 123516200 | 123516800 | YES | YES | YES | NO | Hypermethylation | 600 |
| THEM132C | Intron | chr12 | 127416300 | 127416700 | YES | YES | NO | NO | Hypermethylation | 400 |
| PTGDR | Promoter | chr14 | 51804000 | 51805200 | YES | YES | NO | NO | Hypermethylation | 1200 |
| ISL2 | Intron/Exon | chr15 | 74420000 | 74422000 | YES | YES | NO | YES | Hypermethylation | 2000 |
| chr15: 87750000-87751000 | Intergenic | chr15 | 87750000 | 87751000 | YES | YES | NO | NO | Hypermethylation | 1000 |
| chr15: 87753000-87754100 | Intergenic | chr15 | 87753000 | 87754100 | YES | YES | NO | NO | Hypermethylation | 1100 |
| NR2F2 | Upstream | chr15 | 94666000 | 94667500 | YES | YES | YES | NO | Hypermethylation | 1500 |
| chr16: 11234300-11234900 | Intergenic | chr16 | 11234300 | 11234900 | YES | YES | NO | NO | Hypermethylation | 600 |
| SPN | Exon | chr16 | 29582800 | 29583500 | YES | YES | YES | NO | Hypermethylation | 700 |
| chr16: 85469900-85470200 | Intergenic | chr16 | 85469900 | 85470200 | YES | YES | NO | NO | Hypermethylation | 300 |
| SLFN11 | Promoter | chr17 | 30725100 | 30725600 | YES | YES | NO | NO | Hypermethylation | 500 |
| DLX4 | Upstream | chr17 | 45396800 | 45397800 | YES | YES | NO | YES | Hypermethylation | 1000 |
| SLC38A10 (MGC15523) | Intron | chr17 | 76873800 | 76874300 | YES | YES | YES | NO | Hypermethylation | 500 |
| S1PR4 | Exon | chr19 | 3129900 | 3131100 | YES | YES | YES | YES | Hypermethylation | 1200 |
| MAP2K2 | Intron | chr19 | 4059700 | 4060300 | YES | YES | YES | NO | Hypermethylation | 600 |
| UHRF1 | Intron | chr19 | 4867300 | 4867800 | YES | YES | YES | NO | Hypermethylation | 500 |
| DEDD2 | Exon | chr19 | 47395300 | 47395900 | YES | YES | YES | NO | Hypermethylation | 600 |
| CDC42EP1 | Exon | chr22 | 36292300 | 36292800 | YES | YES | YES | NO | Hypermethylation | 500 |

TABLE 15

Differentially Methylated Genomic Regions (Chromosome 21)

| Region Name | Gene Region | Chrom | Start | End | Microarray Analysis | EPI-TYPER 8 Samples | EPI-TYPER 73 Samples | Previously Validated EPI-TYPER | Relative Methylation Placenta to Maternal | Region Length (bp) |
|---|---|---|---|---|---|---|---|---|---|---|
| chr21: 9906600-9906800 | Intergenic | chr21 | 9906600 | 9906800 | NO | YES | NO | NO | Hypomethylation | 200 |
| chr21: 9907000-9907400 | Intergenic | chr21 | 9907000 | 9907400 | NO | YES | NO | NO | Hypomethylation | 400 |
| chr21: 9917800-9918450 | Intergenic | chr21 | 9917800 | 9918450 | NO | YES | NO | NO | Hypomethylation | 650 |
| TPTE | Promoter | chr21 | 10010000 | 10015000 | NO | YES | NO | NO | Hypomethylation | 5000 |
| chr21: 13974500-13976000 | Intergenic | chr21 | 13974500 | 13976000 | NO | YES | NO | NO | Hypomethylation | 1500 |
| chr21: 13989500-13992000 | Intergenic | chr21 | 13989500 | 13992000 | NO | YES | NO | NO | Hypomethylation | 2500 |
| chr21: 13998500-14000100 | Intergenic | chr21 | 13998500 | 14000100 | NO | YES | NO | NO | Hypomethylation | 1600 |
| chr21: 14017000-14018500 | Intergenic | chr21 | 14017000 | 14018500 | NO | YES | NO | NO | Hypomethylation | 1500 |
| chr21: 14056400-14058100 | Intergenic | chr21 | 14056400 | 14058100 | NO | YES | NO | NO | Hypomethylation | 1700 |
| chr21: 14070250-14070550 | Intergenic | chr21 | 14070250 | 14070550 | NO | YES | NO | NO | Hypomethylation | 300 |
| chr21: 14119800-14120400 | Intergenic | chr21 | 14119800 | 14120400 | NO | YES | NO | NO | Hypomethylation | 600 |

TABLE 15-continued

Differentially Methylated Genomic Regions (Chromosome 21)

| Region Name | Gene Region | Chrom | Start | End | Micro-array Analysis | EPI-TYPER 8 Samples | EPI-TYPER 73 Samples | Previously Validated EPI-TYPER | Relative Methylation Placenta to Maternal | Region Length (bp) |
|---|---|---|---|---|---|---|---|---|---|---|
| chr21: 14304800-14306100 | Intergenic | chr21 | 14304800 | 14306100 | NO | YES | NO | NO | Hypermethylation | 1300 |
| chr21: 15649340-15649450 | Intergenic | chr21 | 15649340 | 15649450 | NO | YES | YES | NO | Hypermethylation | 110 |
| C21orf34 | Intron | chr21 | 16881500 | 16883000 | NO | YES | NO | NO | Hypomethylation | 1500 |
| BTG3 | Intron | chr21 | 17905300 | 17905500 | NO | YES | NO | NO | Hypomethylation | 200 |
| CHODL | Promoter | chr21 | 18539000 | 18539800 | NO | YES | YES | NO | Hypermethylation | 800 |
| NCAM2 | Upstream | chr21 | 21291500 | 21292100 | NO | YES | NO | NO | Hypomethylation | 600 |
| chr21: 23574000-23574600 | Intergenic | chr21 | 23574000 | 23574600 | NO | YES | NO | NO | Hypomethylation | 600 |
| chr21: 24366920-24367060 | Intergenic | chr21 | 24366920 | 24367060 | NO | YES | NO | NO | Hypomethylation | 140 |
| chr21: 25656000-25656900 | Intergenic | chr21 | 25656000 | 25656900 | NO | YES | NO | NO | Hypomethylation | 900 |
| MIR155HG | Promoter | chr21 | 25855800 | 25857200 | NO | YES | YES | NO | Hypermethylation | 1400 |
| CYYR1 | Intron | chr21 | 26830750 | 26830950 | NO | YES | NO | NO | Hypomethylation | 200 |
| chr21: 26938800-26939200 | Intergenic | chr21 | 26938800 | 26939200 | NO | YES | NO | NO | Hypomethylation | 400 |
| GRIK1 | Intron | chr21 | 30176500 | 30176750 | NO | YES | NO | NO | Hypomethylation | 250 |
| chr21: 30741350-30741600 | Intergenic | chr21 | 30741350 | 30741600 | NO | YES | NO | NO | Hypomethylation | 250 |
| TIAM1 | Intron | chr21 | 31426800 | 31427300 | NO | YES | YES | NO | Hypermethylation | 500 |
| TIAM1 | Intron | chr21 | 31475300 | 31475450 | NO | YES | NO | NO | Hypermethylation | 150 |
| TIAM1 | Intron | chr21 | 31621050 | 31621350 | NO | YES | YES | NO | Hypermethylation | 300 |
| SOD1 | Intron | chr21 | 31955000 | 31955300 | NO | YES | NO | NO | Hypomethylation | 300 |
| HUNK | Intron/Exon | chr21 | 32268700 | 32269100 | NO | YES | YES | NO | Hypermethylation | 400 |
| chr21: 33272200-33273300 | Intergenic | chr21 | 33272200 | 33273300 | NO | YES | NO | NO | Hypomethylation | 1100 |
| OLIG2 | Promoter | chr21 | 33314000 | 33324000 | YES | YES | NO | YES | Hypermethylation | 10000 |
| OLIG2 | Downstream | chr21 | 33328000 | 33328500 | YES | YES | NO | NO | Hypomethylation | 500 |
| RUNX1 | Intron | chr21 | 35185000 | 35186000 | NO | YES | NO | NO | Hypomethylation | 1000 |
| RUNX1 | Intron | chr21 | 35320300 | 35320400 | NO | YES | NO | NO | Hypomethylation | 100 |
| RUNX1 | Intron | chr21 | 35321200 | 35321600 | NO | YES | NO | NO | Hypomethylation | 400 |
| RUNX1 | Intron/Exon | chr21 | 35340000 | 35345000 | NO | YES | YES | NO | Hypermethylation | 5000 |
| chr21: 35499200-35499700 | Intergenic | chr21 | 35499200 | 35499700 | NO | YES | YES | NO | Hypermethylation | 500 |
| chr21: 35822800-35823500 | Intergenic | chr21 | 35822800 | 35823500 | NO | YES | YES | NO | Hypermethylation | 700 |
| CBR1 | Promoter | chr21 | 36364000 | 36364500 | NO | YES | NO | NO | Hypermethylation | 500 |
| DOPEY2 | Downstream | chr21 | 36589000 | 36590500 | NO | YES | NO | NO | Hypomethylation | 1500 |
| SIM2 | Promoter | chr21 | 36988000 | 37005000 | YES | YES | YES | YES | Hypermethylation | 17000 |
| HLCS | Intron | chr21 | 37274000 | 37275500 | YES | YES | YES | NO | Hypermethylation | 1500 |
| DSCR6 | Upstream | chr21 | 37300200 | 37300400 | YES | YES | NO | YES | Hypermethylation | 200 |
| DSCR3 | Intron | chr21 | 37551000 | 37553000 | YES | YES | YES | NO | Hypermethylation | 2000 |
| chr21: 37841100-37841800 | Intergenic | chr21 | 37841100 | 37841800 | NO | YES | YES | NO | Hypermethylation | 700 |
| ERG | Intron | chr21 | 38791400 | 38792000 | NO | YES | YES | NO | Hypermethylation | 600 |
| chr21: 39278700-39279800 | Intergenic | chr21 | 39278700 | 39279800 | NO | YES | YES | NO | Hypermethylation | 1100 |
| C21orf129 | Exon | chr21 | 42006000 | 42006250 | NO | YES | YES | NO | Hypermethylation | 250 |
| C2CD2 | Intron | chr21 | 42188900 | 42189500 | NO | YES | YES | NO | Hypermethylation | 600 |
| UMODL1 | Upstream | chr21 | 42355500 | 42357500 | NO | YES | YES | NO | Hypermethylation | 2000 |
| UMODL1/C21orf128 | Intron | chr21 | 42399200 | 42399900 | NO | YES | NO | NO | Hypomethylation | 700 |
| ABCG1 | Intron | chr21 | 42528400 | 42528600 | YES | YES | NO | NO | Hypomethylation | 200 |
| chr21: 42598300-42599600 | Intergenic | chr21 | 42598300 | 42599600 | YES | YES | NO | NO | Hypermethylation | 1300 |
| chr21: 42910000-42911000 | Intergenic | chr21 | 42910000 | 42911000 | NO | YES | NO | NO | Hypomethylation | 1000 |
| PDE9A | Upstream | chr21 | 42945500 | 42946000 | NO | YES | NO | NO | Hypomethylation | 500 |
| PDE9A | Intron | chr21 | 42961400 | 42962700 | NO | YES | NO | NO | Hypomethylation | 1300 |
| PDE9A | Intron | chr21 | 42977400 | 42977600 | NO | YES | NO | NO | Hypomethylation | 200 |
| PDE9A | Intron/Exon | chr21 | 42978200 | 42979800 | YES | YES | NO | NO | Hypomethylation | 1600 |
| PDE9A | Intron | chr21 | 43039800 | 43040200 | NO | YES | YES | NO | Hypermethylation | 400 |
| chr21: 43130800-43131500 | Intergenic | chr21 | 43130800 | 43131500 | NO | YES | NO | NO | Hypomethylation | 700 |
| U2AF1 | Intron | chr21 | 43395500 | 43395800 | NO | YES | NO | NO | Hypermethylation | 300 |
| U2AF1 | Intron | chr21 | 43398000 | 43398450 | NO | YES | YES | NO | Hypermethylation | 450 |
| chr21: 43446600-43447600 | Intergenic | chr21 | 43446600 | 43447600 | NO | YES | NO | NO | Hypomethylation | 1000 |
| CRYAA | Intron/Exon | chr21 | 43463000 | 43466100 | NO | YES | NO | NO | Hypomethylation | 3100 |
| chr21: 43545000-43546000 | Intergenic | chr21 | 43545000 | 43546000 | YES | YES | NO | NO | Hypomethylation | 1000 |
| chr21: 43606000-43606500 | Intergenic | chr21 | 43606000 | 43606500 | NO | YES | NO | NO | Hypomethylation | 500 |
| chr21: 43643000-43644300 | Intergenic | chr21 | 43643000 | 43644300 | YES | YES | YES | YES | Hypermethylation | 1300 |
| C21orf125 | Upstream | chr21 | 43689100 | 43689300 | NO | YES | NO | NO | Hypermethylation | 200 |
| C21orf125 | Downstream | chr21 | 43700700 | 43701700 | NO | YES | NO | NO | Hypermethylation | 1000 |
| HSF2BP | Intron/Exon | chr21 | 43902500 | 43903800 | YES | YES | NO | NO | Hypermethylation | 1300 |
| AGPAT3 | Intron | chr21 | 44161100 | 44161400 | NO | YES | YES | NO | Hypermethylation | 300 |
| chr21: 44446500-44447500 | Intergenic | chr21 | 44446500 | 44447500 | NO | YES | NO | NO | Hypomethylation | 1000 |
| TRPM2 | Intron | chr21 | 44614500 | 44615000 | NO | YES | NO | NO | Hypomethylation | 500 |
| C21orf29 | Intron | chr21 | 44750400 | 44751000 | NO | YES | NO | NO | Hypomethylation | 600 |
| C21orf29 | Intron | chr21 | 44950000 | 44955000 | NO | YES | YES | NO | Hypermethylation | 5000 |
| ITGB2 | Intron/Exon | chr21 | 45145500 | 45146100 | NO | YES | NO | NO | Hypomethylation | 600 |
| POFUT2 | Downstream | chr21 | 45501000 | 45503000 | NO | YES | NO | NO | Hypomethylation | 2000 |
| chr21: 45571500-45573700 | Intergenic | chr21 | 45571500 | 45573700 | NO | YES | NO | NO | Hypomethylation | 2200 |
| chr21: 45609000-45610600 | Intergenic | chr21 | 45609000 | 45610600 | NO | YES | NO | NO | Hypomethylation | 1600 |
| COL18A1 | Intron | chr21 | 45670000 | 45677000 | YES | YES | NO | YES | Hypomethylation | 7000 |
| COL18A1 | Intron/Exon | chr21 | 45700500 | 45702000 | NO | YES | NO | NO | Hypomethylation | 1500 |
| COL18A1 | Intron/Exon | chr21 | 45753000 | 45755000 | YES | YES | NO | YES | Hypomethylation | 2000 |
| chr21: 45885000-45887000 | Intergenic | chr21 | 45885000 | 45887000 | NO | YES | NO | NO | Hypomethylation | 2000 |

TABLE 15-continued

Differentially Methylated Genomic Regions (Chromosome 21)

| Region Name | Gene Region | Chrom | Start | End | Micro-array Analysis | EPI-TYPER 8 Samples | EPI-TYPER 73 Samples | Previously Validated EPI-TYPER | Relative Methylation Placenta to Maternal | Region Length (bp) |
|---|---|---|---|---|---|---|---|---|---|---|
| PCBP3 | Intron | chr21 | 46111000 | 46114000 | NO | YES | NO | NO | Hypomethylation | 3000 |
| PCBP3 | Intron/Exon | chr21 | 46142000 | 46144500 | NO | YES | NO | NO | Hypomethylation | 2500 |
| COL6A1 | Intron/Exon | chr21 | 46227000 | 46233000 | NO | YES | NO | NO | Hypomethylation | 6000 |
| COL6A1 | Intron/Exon | chr21 | 46245000 | 46252000 | NO | YES | NO | NO | Hypomethylation | 7000 |
| chr21: 46280500-46283000 | Intergenic | chr21 | 46280500 | 46283000 | NO | YES | NO | NO | Hypomethylation | 2500 |
| COL6A2 | Intron | chr21 | 46343500 | 46344200 | NO | YES | NO | NO | Hypomethylation | 700 |
| COL6A2 | Intron/Exon | chr21 | 46368000 | 46378000 | NO | YES | NO | NO | Hypomethylation | 10000 |
| C21orf56 | Intron/Exon | chr21 | 46426700 | 46427500 | NO | YES | NO | NO | Hypomethylation | 800 |
| C21orf57 | Intron | chr21 | 46541568 | 46541861 | NO | YES | NO | NO | Hypermethylation | 293 |
| C21orf57 | Exon | chr21 | 46541872 | 46542346 | NO | YES | NO | NO | Hypermethylation | 474 |
| C21orf57 | Downstream | chr21 | 46542319 | 46542665 | NO | YES | NO | NO | Hypermethylation | 346 |
| C21orf58 | Intron | chr21 | 46546914 | 46547404 | NO | YES | NO | NO | Hypomethylation | 490 |
| PRMT2 | Downstream | chr21 | 46911000 | 46913000 | YES | YES | NO | YES | Hypermethylation | 2000 |
| ITGB2 | Intron | chr21 | 45170700 | 45171100 | NO | YES | YES | NO | Hypermethylation | 400 |

Example 11

Examples of Sequences

Provided hereafter are non-limiting examples of certain nucleotide and amino acid sequences.

TABLE 16

Examples of Sequences

| Name | Type | SEQ ID NO | Sequence |
|---|---|---|---|
| TBX3_FP | NA | 1 | CTTTGTCTCTGCGTGCCCGG |
| TBX3_RP | NA | 2 | CGCATGGCCGGCGCCAGAGT |
| SOX14_FP | NA | 3 | CCACGGAATCCCGGCTCTGT |
| SOX14_RP | NA | 4 | CTTCCTAGTGTGAGAACCGGCAAC |
| POP5_FP | NA | 5 | TTGGACCACCAGTTTAGACTGAACTGTGAA |
| POP5_RP | NA | 6 | AGTTGGGTAGGAGTGAGGTGGTATGGCTA |
| APOE_FP | NA | 7 | TTGGAGACAGTTTCTCCTTCCCCAGAC |
| APOE_RP | NA | 8 | AGTTGGCAGCAACGCAGCCCACAG |
| UTY_FP | NA | 9 | TTTCGTGATATTGATGCCGCCCTTCCCATCGC |
| UTY_RP | NA | 10 | TTTCGTGATATTGTCTGTGCTGGGTGTTTTTGCAG |
| DDX3Y_FP | NA | 11 | TTTCGTGATATTCCAAGTTTCAAAAAATCCTGAGTCCACAAT |
| DDX3Y_RP | NA | 12 | TTTCGTGATATGACTTACTGCTCACTGAATTTTGGAGTC |
| DIGctrl1_FP | NA | 13 | CTTCGATAAAAATGATTGCACTCGTGCCCCTTCTTTCTT |
| DIGctrl1_RP | NA | 14 | CTTCGATAAAAATGATTGAGGGGAACCCGGGAGGAT |
| DIGctrl2_FP | NA | 15 | CTTCGATAAAAATGATTGGACAGGCCTTTGCAACAAGGAT |
| DIGctrl2_RP | NA | 16 | CTTCGATAAAAATGATTGGCCTGTTAACCAACCGGGAG |
| POP5_FP_Inhibitor | NA | 17 | TTGGACCACCAGTTTAGACTGAACTGTGAATACAC |
| POP5_RP_Inhibitor | NA | 18 | TTGGGTAGGAGTGAGGTGGTATGGCTATCTGC |
| APOE_FP_Inhibitor | NA | 19 | TTGGAGACAGTTTCTCCTTCCCCAGACACTAT |
| APOE_RP_Inhibitor | NA | 20 | TTGGCAGCAACGCAGCCCACAGCAATG |

TABLE 16-continued

Examples of Sequences

| Name | Type | SEQ ID NO | Sequence |
|---|---|---|---|
| TBX3 Competitor | NA | 21 | CTTTGTCTCTGCGTGCCCGGCAATTCGGATGTTCGTCAAGGACGCGCCCCCT CCCGGTGGGTGATAAACCGATTAAGTTCATCAAGTCTGATCCACTCTGGCGCC GGCCATGCG |
| SOX14 Competitor | NA | 22 | CCACGGAATCCCGGCTCTGTGCAGTTTTCTGGTCGTGTTCAACATGCGCCCAG GTTCCGGGGCTTGGGCATGACTTCGTGATAAAAGATTCGTTGCCGGTTCTCAC ACTAGGAAG |
| POP5 Competitor | NA | 23 | CCACCAGTTTAGACTGAACTGTGAACGCTTGGCTTCCATAAGCAGATGGGTGT CACCAATTGAAAATCACTCTTAAGGATATTCGCGATGAGTAGCCATACCACCTC ACTCCTAC |
| APOE Competitor | NA | 24 | GACAGTTTCTCCTTCCCCAGACTGACTGCCTATGATGTTTATCCTGGCCAATCA CAGGCAGGAAGATGAAGGTCTGATAAAGGAAAGGATACTCGTTCTGTGGGCTG CGTTGCTG |
| UTY Competitor | NA | 25 | GATGCCGCCCTTCCCATCGCTCTCTTCCCCTTCATCAGTATTTTACCAATGACC AAATCAAAGAAATGACTCGCAAGGTTAGAGCGTATCGCAACTGCAAAAACACCC AGCACAGACA |
| DDX3Y Competitor | NA | 26 | CCTTCTGCGGACCTGTTCTTTCACCTCCCTAACCTGAGCAGCGTTACCATGATG TTATTTCTTCATTTGGAGGTAAAACCTCTTAAGATTGTATTCAAACCACCGTGGA TCGCTCACG |
| DIGctrl1 Competitor | NA | 27 | CACTCGTGCCCCTTCTTTCTTCTTATGTTCATCCCGTCAACATTCAACTCCGGC GCCTGCCCCCTCCACATCCCGCATAGCTTGCAAAATACGTGGCCTTACATCCT CCCGGGTTCCCCT |
| DIGctrl2 Competitor | NA | 28 | GACAGGCCTTTGCAACAAGGATCTAACCCTAATGAGCTTAATCAAGATACGGCC GAAGCCACACCGTGCGCCTCAGGAAACACTGACGTTCTTACTGACCCTCCCGG TTGGTTAACAGGC |
| TBX3 genomic target | NA | 29 | CTTTGTCTCTGCGTGCCCGGCGCGCCCCCCTCCCGGTGGGTGATAAACCCACT CTGGCGCCGGCCATGCG |
| SOX14 genomic target | NA | 30 | CCACGGAATCCCGGCTCTGTGTGCGCCCAGGTTCCGGGGCTTGGGCGTTGCC GGTTCTCACACTAGGAAG |
| POP5 genomic target | NA | 31 | CCACCAGTTTAGACTGAACTGTGAACGTGTCACCAATTGAAAATCAGTAGCCAT ACCACCTCACTCCTAC |
| APOE genomic target | NA | 32 | GACAGTTTCTCCTTCCCCAGACTGGCCAATCACAGGCAGGAAGATGAAGGTTC TGTGGGCTGCGTTGCTG |
| UTY genomic target | NA | 33 | GATGCCGCCCTTCCCATCGCTCTCTTCCCCTTCAAGCGTATCGCAACTGCAAAA ACACCCAGCACAGACA |
| DDX3Y genomic target | NA | 34 | CCTTCTGCGGACCTGTTCTTTCACCTCCCTAACCTGAAGATTGTATTCAAACCA CCGTGGATCGCTCACG |
| DIGctrl1 genomic target (POP5) | NA | 35 | CACTCGTGCCCCTTCTTTCTTCCTCCGGCGCCTGCCCCCTCCACATCCCGCCA TCCTCCCGGGTTCCCCT |
| DIGctrl2 genomic target (LDHA) | NA | 36 | GACAGGCCTTTGCAACAAGGATCACGGCCGAAGCCACACCGTGCGCCTCCCT CCCGGTTGGTTAACAGGC |
| SRY Competitor | NA | 37 | GTGCAACTGGACAACAGGTTGTACAGGGATGACTGTTTTATGATAATCCCAATG CTTTGCGTGACTATTTTCGTGATATTGGGTACGAAAGCCACACACTCAAGAATG GAGCACCAGC |
| SRY genomic target | NA | 38 | GTGCAACTGGACAACAGGTTGTACAGGGATGACTCGAAAGCCACACACTCAAG AATGGAGCACCAGC |

Example 12

Examples of Embodiments

A1. A method for determining the amount of a minority nucleic acid species in a sample comprising:

(a) contacting under amplification conditions a nucleic acid sample comprising a minority species and a majority species, the combination of the minority species and the majority species comprising total nucleic acid in the sample, with:

(i) a first set of amplification primers that specifically amplify a first region in sample nucleic acid comprising a feature that (1) is present in the minority nucleic acid species and is not present in the majority nucleic acid species, or (2) is not present in the minority nucleic acid species and is present in the majority nucleic acid species, (ii) a second set of amplification primers that amplify a second region in the sample nucleic acid allowing for a determination of total nucleic acid in the sample, wherein the first region and the second region are different, and (iii) one or more inhibitory oligonucleotides that reduce the amplification of the second region, thereby generating minority nucleic acid amplification products and total nucleic acid amplification products, wherein the total nucleic acid amplification products are reduced relative to total amplification products that would be generated if no inhibitory oligonucleotide was present;

(b) separating the minority nucleic acid amplification products and total nucleic acid amplification products, thereby generating separated minority nucleic acid amplification products and total nucleic acid amplification products; and (c) determining the fraction of the minority nucleic acid species in the sample based on the amount of each of the separated minority nucleic acid amplification products and total nucleic acid amplification products.

A1.1 The method of embodiment A1 or A1.1, wherein the fraction of the minority nucleic acid species in the sample is relative to the total amount of the nucleic acid in the sample.

A2. The method of embodiment A1, wherein the feature that is present in the minority nucleic acid species and not present in the majority nucleic acid species is methylation.

A3. The method of embodiment A2, wherein the first region is methylated.

A4. The method of embodiment A3, wherein the second region is unmethylated.

A5. The method of any one of embodiments A1 to A4, further comprising contacting the nucleic acid sample with one or more restriction enzymes prior to (a).

A6. The method of embodiment A5, wherein the one or more restriction enzymes are methylation sensitive.

A7. The method of embodiment A6, wherein the restriction enzymes are HhaI and HpaII.

A8. The method of any one of embodiments A1 to A7, further comprising contacting under amplification conditions the nucleic acid sample with a third set of amplification primers that amplify a third region in the sample nucleic acid allowing for a determination of the presence or absence of fetal specific nucleic acid.

A9. The method of embodiment A8, wherein the fetal specific nucleic acid is Y chromosome nucleic acid.

A10. The method of any one of embodiments A1 to A9, further comprising contacting under amplification conditions the nucleic acid sample with a fourth set of amplification primers that amplify a fourth region in the sample nucleic acid allowing for a determination of the amount of digested or undigested nucleic acid, as an indicator of digestion efficiency.

A11. The method of embodiment A10, wherein the first, second, third and fourth regions each comprise one or more genomic loci.

A12. The method of embodiment A11, wherein the genomic loci are the same length.

A13. The method of embodiment A12, wherein the genomic loci are about 50 base pairs to about 200 base pairs.

A14. The method of embodiment A13, wherein the genomic loci are about 60 base pairs to about 80 base pairs.

A15. The method of embodiment A14, wherein the genomic loci are about 70 base pairs.

A16. The method of embodiment A1, wherein the first region comprises one or more loci that are differentially methylated between the minority and majority species.

A17. The method of embodiment A1, wherein the first region comprises loci within the TBX3 and SOX14 genes.

A18. The method of embodiment A17, wherein the loci for the first region each comprise independently SEQ ID NO:29 and SEQ ID NO:30.

A19. The method of embodiment A1, wherein the second region comprises one or more loci which do not contain a restriction site for a methylation-sensitive restriction enzyme.

A20. The method of embodiment A1, wherein the second region comprises loci within the POP5 and APOE genes.

A21. The method of embodiment A20, wherein the loci for the second region each comprise independently SEQ ID NO:31 and SEQ ID NO:32.

A22. The method of embodiment A9, wherein the third region comprises one or more loci within chromosome Y.

A23. The method of embodiment A9, wherein the third region comprises a locus within the DDX3Y gene.

A24. The method of embodiment A23, wherein the locus for the third region comprises SEQ ID NO:34.

A25. The method of embodiment A10, wherein the fourth region comprises one or more loci present in every genome in the sample and unmethylated in all species.

A26. The method of embodiment A10, wherein the fourth region comprises loci within the POP5 or LDHA genes.

A27. The method of embodiment A26, wherein the loci for the fourth region each comprise independently SEQ ID NO:35 and SEQ ID NO:36.

A28. The method of embodiment A1, wherein the first and second sets of amplification primers each comprise one or more pairs of forward and reverse primers.

A29. The method of embodiment A10, wherein the third and fourth sets of amplification primers each comprise one or more pairs of forward and reverse primers.

A30. The method of embodiment A28 or A29, wherein one or more amplification primer pairs further comprise a 5' tail.

A31. The method of embodiment A30, wherein the 5' tail is a distinct length for each amplification primer set.

A32. The method of any one of embodiments A28 to A31, wherein the amplification primers each comprise independently SEQ ID NOs:1 to 8 and SEQ ID NOs:11 to 16.

A33. The method of embodiment A1, wherein an inhibitory oligonucleotide of the one or more inhibitory oligonucleotides comprises a nucleotide sequence complementary to a nucleotide sequence in the second region.

A34. The method of embodiment A33, wherein the inhibitory oligonucleotide and a primer in the second set of amplification primers are complementary to the same nucleotide sequence in the second region.

A35. The method of embodiment A33 or A34, wherein the inhibitory oligonucleotide comprises one or more 3' mismatched nucleotides.

A36. The method of embodiment A35, wherein the inhibitory oligonucleotides each comprise independently SEQ ID NO:17, SEQ ID NO:18, SEQ ID NO:19, and SEQ ID NO:20.

A37. The method of any one of embodiments A1 to A36, further comprising contacting under amplification conditions the nucleic acid sample with one or more first competitor oligonucleotides that compete with the first region for hybridization of primers of the first amplification primer set.

A38. The method of any one of embodiments A1 to A37, further comprising contacting under amplification conditions the nucleic acid sample with one or more second competitor oligonucleotides that compete with the second region for hybridization of primers of the second amplification primer set.

A39. The method of any one of embodiments A8 to A38, further comprising contacting under amplification conditions the nucleic acid sample with one or more third competitor oligonucleotides that compete with the third region for hybridization of primers of the third amplification primer set.

A40. The method of any one of embodiments A10 to A39, further comprising contacting under amplification conditions the nucleic acid sample with one or more fourth competitor oligonucleotides that compete with the fourth region for hybridization of primers of the fourth amplification primer set.

A41. The method of any one of embodiments A37 to A40, wherein the competitor oligonucleotides comprise a stuffer sequence.

A42. The method of embodiment A41, wherein the stuffer sequence length is constant for one or more of the first competitor oligonucleotides, second competitor oligonucleotides, third competitor oligonucleotides and fourth competitor oligonucleotides.

A43. The method of embodiment A41, wherein the stuffer sequence length is variable for one or more of the first competitor oligonucleotides, second competitor oligonucleotides, third competitor oligonucleotides and fourth competitor oligonucleotides.

A44. The method of embodiment A42 or A43, wherein the stuffer sequence is from a non-human genome.

A45. The method of embodiment A44, wherein the stuffer sequence is from the PhiX 174 genome.

A46. The method of any one of embodiments A37 to A45, wherein the competitor oligonucleotide is about 100 to about 150 base pairs long.

A47. The method of embodiment A46, wherein the competitor oligonucleotide is about 115 to about 120 base pairs long.

A48. The method of embodiment A47, wherein the first and second competitor oligonucleotide is about 115 base pairs long.

A49. The method of embodiment A47, wherein the third competitor oligonucleotide is about 118 base pairs long.

A50. The method of embodiment A47, wherein the fourth competitor oligonucleotide is about 120 base pairs long.

A51. The method of embodiment A48, wherein the one or more first competitor oligonucleotides each comprise independently SEQ ID NO:21 and SEQ ID NO:22.

A52. The method of embodiment A48, wherein the one or more second competitor oligonucleotides each comprise independently SEQ ID NO:23 and SEQ ID NO:24.

A53. The method of embodiment A49, wherein the third competitor oligonucleotide comprises SEQ ID NO:26.

A54. The method of embodiment A50, wherein the one or more fourth competitor oligonucleotides each comprise independently SEQ ID NO:27 and SEQ ID NO:28.

A55. The method of any one of embodiments A37 to A54, wherein one or more competitor oligonucleotides comprise a detectable label.

A56. The method of embodiment A55, wherein the detectable label is a fluorophore.

A57. The method of embodiment A56, wherein the fluorophore is different for each competitor oligonucleotide.

A58. The method of any one of embodiments A37 to A57, wherein a predetermined copy number of each competitor oligonucleotide is used.

A59. The method of embodiment A58, further comprising determining the copy number of the minority nucleic acid species based on the amount of competitor oligonucleotide used.

A60. The method of embodiment A59, further comprising determining the copy number of the majority nucleic acid species.

A61. The method of any one of embodiments A1 to A60, wherein the sample nucleic acid is extracellular nucleic acid.

A62. The method of any one embodiments A1 to A61, wherein the minority nucleic acid species is fetal DNA.

A63. The method of any one of embodiments A1 to A62, wherein the majority nucleic acid species is maternal DNA.

A64. The method of any one of embodiments A1 to A63, wherein the nucleic acid sample is obtained from a pregnant female subject.

A65. The method of embodiment A64, wherein the subject is human.

A66. The method of any one of embodiments A1 to A65, wherein the sample nucleic acid is from plasma.

A67. The method of any one of embodiments A1 to A65, wherein the sample nucleic acid is from serum.

A68. The method of any one of embodiments A1 to A67, wherein the amplification is in a single reaction vessel.

A69. The method of any one of embodiments A1 to A68, wherein two or more of the amplification products are different lengths.

A70. The method of any one of embodiments A1 to A69, wherein the amplification is by polymerase chain reaction (PCR).

A71. The method of any one of embodiments A1 to A70, further comprising contacting the amplification products with an exonuclease prior to (b).

A72. The method of any one of embodiments A1 to A71, wherein the separation of amplification products is based on length.

A73. The method of any one of embodiments A1 to A72, wherein the separation is performed using electrophoresis.

A74. The method of embodiment A73, wherein the electrophoresis is capillary electrophoresis.

A75. The method of any of embodiments A1 to A74, further comprising determining whether the nucleic acid sample is utilized for a sequencing reaction.

A76. The method of embodiment A75, wherein the sequencing reaction is a reversible terminator-based sequencing reaction.

A77. The method of any of embodiments A1 to A76, further comprising determining whether sequencing information obtained for a nucleic acid sample is used for a diagnostic determination.

B1. A method for determining the copy number of a minority nucleic acid species in a sample comprising:
 (a) contacting under amplification conditions a nucleic acid sample comprising a minority species and a majority species, the combination of the minority species and the majority species comprising total nucleic acid in the sample, with:
  (i) a first set of amplification primers that specifically amplify a first region in sample nucleic acid comprising a feature that (1) is present in the minority nucleic acid species and is not present in the majority nucleic acid species, or (2) is not present in the minority nucleic acid species and is present in the majority nucleic acid species,
  (ii) a second set of amplification primers that amplify a second region in the sample nucleic acid allowing for a determination of the total nucleic acid in the sample, wherein the first region and the second region are different, (iii) one or more first competitor oligonucleotides that compete with the first region for hybridization of primers of the first amplification primer set, and (iv) one or more second competitor oligonucleotides that compete with the second region for hybridization of primers of the second amplification primer set, thereby generating amplification products, wherein two or more of the amplification products are different lengths;

(b) separating the minority nucleic acid amplification products, total nucleic acid amplification products, and competitor amplification products, thereby generating separated minority nucleic acid amplification products, total nucleic acid amplification products, and competitor amplification products; and (c) determining the copy number of the minority nucleic acid species in the sample based on the separated amplification products.

B2. The method of embodiment B1, wherein the feature that is present in the minority nucleic acid species and not present in the majority nucleic acid species is methylation.

B3. The method of embodiment B2, wherein the first region is methylated.

B4. The method of embodiment B3, wherein the second region is unmethylated.

B5. The method of any one of embodiments B1 to B4, further comprising contacting the nucleic acid sample with one or more restriction enzymes prior to (a).

B6. The method of embodiment B5, wherein the one or more restriction enzymes are methylation sensitive.

B7. The method of embodiment B6, wherein the restriction enzymes are HhaI and HpaII.

B8. The method of any one of embodiments B1 to B7, further comprising contacting under amplification conditions the nucleic acid sample with a third set of amplification primers that amplify a third region in the sample nucleic acid allowing for a determination of the presence or absence of fetal specific nucleic acid.

B9. The method of embodiment B8, wherein the fetal specific nucleic acid is Y chromosome nucleic acid.

B10. The method of any one of embodiments B1 to B9, further comprising contacting under amplification conditions the nucleic acid sample with a fourth set of amplification primers that amplify a fourth region in the sample nucleic acid allowing for a determination of the amount of digested or undigested nucleic acid, as an indicator of digestion efficiency.

B11. The method of embodiment B10, wherein the first, second, third and fourth regions each comprise one or more genomic loci.

B12. The method of embodiment B11, wherein the genomic loci are the same length.

B13. The method of embodiment B12, wherein the genomic loci are about 50 base pairs to about 200 base pairs.

B14. The method of embodiment B13, wherein the genomic loci are about 60 base pairs to about 80 base pairs.

B15. The method of embodiment B14, wherein the genomic loci are about 70 base pairs.

B16. The method of embodiment B1, wherein the first region comprises one or more loci that are differentially methylated between the minority and majority species.

B17. The method of embodiment B1, wherein the first region comprises loci within the TBX3 and SOX14 genes.

B18. The method of embodiment B17, wherein the loci for the first region each comprise independently SEQ ID NO:29 and SEQ ID NO:30.

B19. The method of embodiment B1, wherein the second region comprises one or more loci which do not contain a restriction site for a methylation-sensitive restriction enzyme.

B20. The method of embodiment B1, wherein the second region comprises loci within the POP5 and APOE genes.

B21. The method of embodiment B20, wherein the loci for the second region each comprise independently SEQ ID NO:31 and SEQ ID NO:32.

B22. The method of embodiment B9, wherein the third region comprises one or more loci within chromosome Y.

B23. The method of embodiment B9, wherein the third region comprises a locus within the DDX3Y gene.

B24. The method of embodiment B23, wherein the locus for the third region comprises SEQ ID NO:34.

B25. The method of embodiment B10, wherein the fourth region comprises one or more loci present in every genome in the sample and unmethylated in all species.

B26. The method of embodiment B10, wherein the fourth region comprises loci within the POP5 or LDHA genes.

B27. The method of embodiment B26, wherein the loci for the fourth region each comprise independently SEQ ID NO:35 and SEQ ID NO:36.

B28. The method of embodiment B1, wherein the first and second sets of amplification primers each comprise one or more pairs of forward and reverse primers.

B29. The method of embodiment B10, wherein the third and fourth sets of amplification primers each comprise one or more pairs of forward and reverse primers.

B30. The method of embodiment B28 or B29, wherein one or more amplification primer pairs further comprise a 5' tail.

B31. The method of embodiment B30, wherein the 5' tail is a distinct length for each amplification primer set.

B32. The method of any one of embodiments B28 to B31, wherein the amplification primers each comprise independently SEQ ID NOs:1 to 8 and SEQ ID NOs:11 to 16.

B33. The method of any one of embodiments B1 to B32, further comprising contacting under amplification conditions the nucleic acid sample with one or more inhibitory oligonucleotides that reduce the amplification of the second region.

B34. The method of embodiment B33, wherein an inhibitory oligonucleotide of the one or more inhibitory oligonucleotides comprises a nucleotide sequence complementary to a nucleotide sequence in the second region.

B35. The method of embodiment B34, wherein the inhibitory oligonucleotide and a primer in the second set of amplification primers are complementary to the same nucleotide sequence in the second region.

B36. The method of embodiment B34 or B35, wherein the inhibitory oligonucleotide comprises one or more 3' mismatched nucleotides.

B37. The method of embodiment B36, wherein the inhibitory oligonucleotides each comprise independently SEQ ID NO:17, SEQ ID NO:18, SEQ ID NO:19, and SEQ ID NO:20.

B38. The method of any one of embodiments B1 to B37, further comprising determining the fraction of the minority nucleic acid species in the sample based on the amount of each of the separated minority and total nucleic acid amplification products.

B38.1 The method of embodiment B38, wherein the fraction of the minority nucleic acid species in the sample is relative to the total amount of the nucleic acid in the sample.

B39. The method of any one of embodiments B8 to B38.1, further comprising contacting under amplification conditions the nucleic acid sample with one or more third competitor oligonucleotides that compete with the third region for hybridization of primers of the third amplification primer set.

B40. The method of any one of embodiments B10 to B39, further comprising contacting under amplification conditions the nucleic acid sample with one or more fourth competitor oligonucleotides that compete with the fourth region for hybridization of primers of the fourth amplification primer set.

B41. The method of any one of embodiments B1 to B40, wherein the competitor oligonucleotides comprise a stuffer sequence.

B42. The method of embodiment B41, wherein the stuffer sequence length is constant for one or more of the first competitor oligonucleotides, second competitor oligonucleotides, third competitor oligonucleotides and fourth competitor oligonucleotides.

B43. The method of embodiment B41, wherein the stuffer sequence length is variable for one or more of the first competitor oligonucleotides, second competitor oligonucleotides, third competitor oligonucleotides and fourth competitor oligonucleotides.

B44. The method of embodiments B42 or B43, wherein the stuffer sequence is from a non-human genome.

B45. The method of embodiment B44, wherein the stuffer sequence is from the PhiX 174 genome.

B46. The method of any one of embodiments B1 to B45, wherein the competitor oligonucleotide is about 100 to about 150 base pairs long.

B47. The method of embodiment B46, wherein the competitor oligonucleotide is about 115 to about 120 base pairs long.

B48. The method of embodiment B47, wherein the first and second competitor oligonucleotide is about 115 base pairs long.

B49. The method of embodiment B47, wherein the third competitor oligonucleotide is about 118 base pairs long.

B50. The method of embodiment B47, wherein the fourth competitor oligonucleotide is about 120 base pairs long.

B51. The method of embodiment B48, wherein the one or more first competitor oligonucleotides each comprise independently SEQ ID NO:21 and SEQ ID NO:22.

B52. The method of embodiment B48, wherein the one or more second competitor oligonucleotides each comprise independently SEQ ID NO:23 and SEQ ID NO:24.

B53. The method of embodiment B49, wherein the third competitor oligonucleotide comprises SEQ ID NO:26.

B54. The method of embodiment B50, wherein the one or more fourth competitor oligonucleotides each comprise independently SEQ ID NO:27 and SEQ ID NO:28.

B55. The method of any one of embodiments B1 to B54, wherein one or more competitor oligonucleotides comprise a detectable label.

B56. The method of embodiment B55, wherein the detectable label is a fluorophore.

B57. The method of embodiment B56, wherein the fluorophore is different for each competitor oligonucleotide.

B58. The method of any one of embodiments B1 to B57, wherein a predetermined copy number of each competitor oligonucleotide is used.

B59. The method of embodiment B58, wherein the copy number of the minority nucleic acid species is determined based on the amount of competitor oligonucleotide used.

B60. The method of embodiment B59, wherein the copy number of the majority nucleic acid species is determined.

B61. The method of any one of embodiments B1 to B60, wherein the sample nucleic acid is extracellular nucleic acid.

B62. The method of any one embodiments B1 to B61, wherein the minority nucleic acid species is fetal DNA.

B63. The method of any one of embodiments B1 to B62, wherein the majority nucleic acid species is maternal DNA.

B64. The method of any one of embodiments B1 to B63, wherein the nucleic acid sample is obtained from a pregnant female subject.

B65. The method of embodiment B64, wherein the subject is human.

B66. The method of any one of embodiments B1 to B65, wherein the sample nucleic acid is from plasma.

B67. The method of any one of embodiments B1 to B65, wherein the sample nucleic acid is from serum.

B68. The method of any one of embodiments B1 to B67, wherein the amplification is in a single reaction vessel.

B69. The method of any one of embodiments B1 to B68, wherein the amplification is by polymerase chain reaction (PCR).

B70. The method of any one of embodiments B1 to B69, further comprising contacting the amplification products with an exonuclease prior to (b).

B71. The method of any one of embodiments B1 to B70, wherein the separation of amplification products is based on length.

B72. The method of any one of embodiments B1 to B71, wherein the separation is performed using electrophoresis.

B73. The method of embodiment B72, wherein the electrophoresis is capillary electrophoresis.

B74. The method of any of embodiments B1 to B73, further comprising determining whether the nucleic acid sample is utilized for a sequencing reaction.

B75. The method of embodiment B74, wherein the sequencing reaction is a reversible terminator-based sequencing reaction.

B76. The method of any of embodiments B1 to B75, further comprising determining whether sequencing information obtained for a nucleic acid sample is used for a diagnostic determination.

C1. A method for determining the amount of a minority nucleic acid species in a sample comprising:
(a) contacting under amplification conditions a nucleic acid sample comprising a minority species and a majority species, the combination of the minority species and the majority species comprising total nucleic acid in the sample, with:
  (i) a first set of amplification primers that specifically amplify a first region in sample nucleic acid comprising a feature that (1) is present in the minority nucleic acid species and is not present in the majority nucleic acid species, or (2) is not present in the minority nucleic acid species and is present in the majority nucleic acid species,
  (ii) a second set of amplification primers that amplify a second region in the sample nucleic acid allowing for a determination of total nucleic acid in the sample, wherein the first region and the second region are different,
  (iii) one or more inhibitory oligonucleotides that reduce the amplification of the second region,
  (iv) one or more first competitor oligonucleotides that compete with the first region for hybridization of primers of the first amplification primer set, and
  (v) one or more second competitor oligonucleotides that compete with the second region for hybridization of primers of the second amplification primer set, thereby generating minority nucleic acid amplification products, total nucleic acid amplification products and competitor amplification products, wherein two or more of the amplification products are different lengths and the total nucleic acid amplification products are reduced relative to total amplification products that would be generated if no inhibitory oligonucleotide was present;

(b) separating the amplification products, thereby generating separated minority nucleic acid amplification products, total nucleic acid amplification products, and competitor amplification products; and (c) determining the amount of the minority nucleic acid species in the sample based on the separated amplification products.

C2. The method of embodiment C1, wherein the feature that is present in the minority nucleic acid species and not present in the majority nucleic acid species is methylation.

C3. The method of embodiment C2, wherein the first region is methylated.

C4. The method of embodiment C3, wherein the second region is unmethylated.

C5. The method of any one of embodiments C1 to C4, further comprising contacting the nucleic acid sample with one or more restriction enzymes prior to (a).

C6. The method of embodiment C5, wherein the one or more restriction enzymes are methylation sensitive.

C7. The method of embodiment C6, wherein the restriction enzymes are HhaI and HpaII.

C8. The method of any one of embodiments C1 to C7, further comprising contacting under amplification conditions the nucleic acid sample with a third set of amplification primers that amplify a third region in the sample nucleic acid allowing for a determination of the presence or absence of fetal specific nucleic acid.

C9. The method of embodiment C8, wherein the fetal specific nucleic acid is Y chromosome nucleic acid.

C10. The method of any one of embodiments C1 to C9, further comprising contacting under amplification conditions the nucleic acid sample with a fourth set of amplification primers that amplify a fourth region in the sample nucleic acid allowing for a determination of the amount of digested or undigested nucleic acid, as an indicator of digestion efficiency.

C11. The method of embodiment C10, wherein the first, second, third and fourth regions each comprise one or more genomic loci.

C12. The method of embodiment C11, wherein the genomic loci are the same length.

C13. The method of embodiment C12, wherein the genomic loci are about 50 base pairs to about 200 base pairs.

C14. The method of embodiment C13, wherein the genomic loci are about 60 base pairs to about 80 base pairs.

C15. The method of embodiment C14, wherein the genomic loci are about 70 base pairs.

C16. The method of embodiment C1, wherein the first region comprises one or more loci that are differentially methylated between the minority and majority species.

C17. The method of embodiment C1, wherein the first region comprises loci within the TBX3 and SOX14 genes.

C18. The method of embodiment C17, wherein the loci for the first region each comprise independently SEQ ID NO:29 and SEQ ID NO:30.

C19. The method of embodiment C1, wherein the second region comprises one or more loci which do not contain a restriction site for a methylation-sensitive restriction enzyme.

C20. The method of embodiment C1, wherein the second region comprises loci within the POP5 and APOE genes.

C21. The method of embodiment C20, wherein the loci for the second region each comprise independently SEQ ID NO:31 and SEQ ID NO:32.

C22. The method of embodiment C9, wherein the third region comprises one or more loci within chromosome Y.

C23. The method of embodiment C9, wherein the third region comprises a locus within the DDX3Y gene.

C24. The method of embodiment C23, wherein the locus for the third region comprises SEQ ID NO:34.

C25. The method of embodiment C10, wherein the fourth region comprises one or more loci present in every genome in the sample and unmethylated in all species.

C26. The method of embodiment C10, wherein the fourth region comprises loci within the POP5 or LDHA genes.

C27. The method of embodiment C26, wherein the loci for the fourth region each comprise independently SEQ ID NO:35 and SEQ ID NO:36.

C28. The method of embodiment C1, wherein the first and second sets of amplification primers each comprise one or more pairs of forward and reverse primers.

C29. The method of embodiment C10, wherein the third and fourth sets of amplification primers each comprise one or more pairs of forward and reverse primers.

C30. The method of embodiment C28 or C29, wherein one or more amplification primer pairs further comprise a 5' tail.

C31. The method of embodiment C30, wherein the 5' tail is a distinct length for each amplification primer set.

C32. The method of any one of embodiments C28 to C31, wherein the amplification primers each comprise independently SEQ ID NOs:1 to 8 and SEQ ID NOs:11 to 16.

C33. The method of embodiment C1, wherein an inhibitory oligonucleotide of the one or more inhibitory oligonucleotides comprises a nucleotide sequence complementary to a nucleotide sequence in the second region.

C34. The method of embodiment C33, wherein the inhibitory oligonucleotide and a primer in the second set of amplification primers are complementary to the same nucleotide sequence in the second region.

C35. The method of embodiment C33 or C34, wherein the inhibitory oligonucleotide comprises one or more 3' mismatched nucleotides.

C36. The method of embodiment C35, wherein the inhibitory oligonucleotides each comprise independently SEQ ID NO:17, SEQ ID NO:18, SEQ ID NO:19, and SEQ ID NO:20.

C37. The method of any one of embodiments C1 to C36, wherein the amount of the minority nucleic acid determined is the fraction of the minority nucleic acid species in the sample based on the amount of each of the separated minority and total nucleic acid amplification products.

C37.1 The method of embodiment C37, wherein the fraction of the minority nucleic acid species in the sample is relative to the total amount of the nucleic acid in the sample.

C38. The method of any one of embodiments C8 to C37.1, further comprising contacting under amplification conditions the nucleic acid sample with one or more third competitor oligonucleotides that compete with the third region for hybridization of primers of the third amplification primer set.

C39. The method of any one of embodiments C10 to C38, further comprising contacting under amplification conditions the nucleic acid sample with one or more fourth competitor oligonucleotides that compete with the fourth region for hybridization of primers of the fourth amplification primer set.

C40. The method of any one of embodiments C1 to C39, wherein the competitor oligonucleotides comprise a stuffer sequence.

C41. The method of embodiment C40, wherein the stuffer sequence length is constant for one or more of the first competitor oligonucleotides, second competitor oligonucleotides, third competitor oligonucleotides and fourth competitor oligonucleotides.

C42. The method of embodiment C40, wherein the stuffer sequence length is variable for one or more of the first competitor oligonucleotides, second competitor oligonucleotides, third competitor oligonucleotides and fourth competitor oligonucleotides.

C43. The method of embodiment C41 or C42, wherein the stuffer sequence is from a non-human genome.

C44. The method of embodiment C43, wherein the stuffer sequence is from the PhiX 174 genome.

C45. The method of any one of embodiments C1 to C44, wherein the competitor oligonucleotide is about 100 to about 150 base pairs long.

C46. The method of embodiment C45, wherein the competitor oligonucleotide is about 115 to about 120 base pairs long.

C47. The method of embodiment C46, wherein the first and second competitor oligonucleotide is about 115 base pairs long.

C48. The method of embodiment C46, wherein the third competitor oligonucleotide is about 118 base pairs long.

C49. The method of embodiment C46, wherein the fourth competitor oligonucleotide is about 120 base pairs long.

C50. The method of embodiment C47, wherein the one or more first competitor oligonucleotides each comprise independently SEQ ID NO:21 and SEQ ID NO:22.

C51. The method of embodiment C47, wherein the one or more second competitor oligonucleotides each comprise independently SEQ ID NO:23 and SEQ ID NO:24.

C52. The method of embodiment C48, wherein the third competitor oligonucleotide comprises SEQ ID NO:26.

C53. The method of embodiment C49, wherein the one or more fourth competitor oligonucleotides each comprise independently SEQ ID NO:27 and SEQ ID NO:28.

C54. The method of any one of embodiments C1 to C53, wherein one or more competitor oligonucleotides comprise a detectable label.

C55. The method of embodiment C54, wherein the detectable label is a fluorophore.

C56. The method of embodiment C55, wherein the fluorophore is different for each competitor oligonucleotide.

C57. The method of any one of embodiments C1 to C56, wherein a predetermined copy number of each competitor oligonucleotide is used.

C58. The method of embodiment C57, wherein the amount of the minority nucleic acid determined is the copy number of the minority nucleic acid species based on the amount of competitor oligonucleotide used.

C59. The method of embodiment C58, further comprising determining the copy number of the majority nucleic acid species.

C60. The method of any one of embodiments C1 to C59, wherein the sample nucleic acid is extracellular nucleic acid.

C61. The method of any one embodiments C1 to C60, wherein the minority nucleic acid species is fetal DNA.

C62. The method of any one of embodiments C1 to C61, wherein the majority nucleic acid species is maternal DNA.

C63. The method of any one of embodiments C1 to C62, wherein the nucleic acid sample is obtained from a pregnant female subject.

C64. The method of embodiment C63, wherein the subject is human.

C65. The method of any one of embodiments C1 to C64, wherein the sample nucleic acid is from plasma.

C66. The method of any one of embodiments C1 to C64, wherein the sample nucleic acid is from serum.

C67. The method of any one of embodiments C1 to C66, wherein the amplification is in a single reaction vessel.

C68. The method of any one of embodiments C1 to C67, wherein the amplification is by polymerase chain reaction (PCR).

C69. The method of any one of embodiments C1 to C68, further comprising contacting the amplification products with an exonuclease prior to (b).

C70. The method of any one of embodiments C1 to C69, wherein the separation of amplification products is based on length.

C71. The method of any one of embodiments C1 to C70, wherein the separation is performed using electrophoresis.

C72. The method of embodiment C71, wherein the electrophoresis is capillary electrophoresis.

C73. The method of any of embodiments C1 to C72, further comprising determining whether the nucleic acid sample is utilized for a sequencing reaction.

C74. The method of embodiment C73, wherein the sequencing reaction is a reversible terminator-based sequencing reaction.

C75. The method of any of embodiments C1 to C74, further comprising determining whether sequencing information obtained for a nucleic acid sample is used for a diagnostic determination.

D1. A method for determining the amount of fetal nucleic acid in a sample comprising:

(a) contacting under amplification conditions a nucleic acid sample comprising fetal nucleic acid and maternal nucleic acid, the combination of the fetal species and the maternal species comprising total nucleic acid in the sample, with:

(i) a first set of amplification primers that specifically amplify a first region in sample nucleic acid having a feature that (1) is present in the fetal nucleic acid and is not present in the maternal nucleic acid, or (2) is not present in the fetal nucleic acid and is present in the maternal nucleic acid, (ii) a second set of amplification primers that amplify a second region in the sample nucleic acid allowing for a determination of the total nucleic acid in the sample, (iii) one or more inhibitory oligonucleotides that reduce the amplification of the second region, (iv) a third set of amplification primers that amplify a third region in the sample nucleic acid allowing for a determination of the presence or absence of Y chromosome nucleic acid, (v) a fourth set of amplification primers that amplify a fourth region in the sample nucleic acid allowing for a determination of the amount of digested or undigested nucleic acid, as an indicator of digestion efficiency, wherein the first, second, third and fourth regions are different, (vi) one or more first competitor oligonucleotides that compete with the first region for hybridization of primers of the first amplification primer set, (vii) one or more second competitor oligonucleotides that compete with the second region for hybridization of primers of the second amplification primer set, (viii) one or more third competitor oligonucleotides that compete with the third region for hybridization of primers of the third amplification primer set, and (ix) one or more fourth competitor oligonucleotides that compete with the fourth region for hybridization of primers of the fourth amplification primer set, thereby generating fetal nucleic acid amplification products, total nucleic acid amplification products, Y chromosome nucleic acid amplification products, digestion efficiency indicator amplification products, and competitor amplification products, wherein two or more of the amplification products are different lengths and the total nucleic acid amplification products are reduced relative to total amplification products that would be generated if no inhibitory oligonucleotide was present;

(b) separating the amplification products, thereby generating separated fetal nucleic acid amplification products, total nucleic acid amplification products, Y chromosome nucleic acid amplification products, digestion efficiency indicator amplification products, and competitor amplification products; and (c) determining the amount of the fetal nucleic acid in the sample based on the separated amplification products.

D2. The method of embodiment D1, wherein the feature that is present in the fetal nucleic acid and not present in the maternal nucleic acid is methylation.

D3. The method of embodiment D2, wherein the first region is methylated.

D4. The method of embodiment D3, wherein the second region is unmethylated.

D5. The method of any one of embodiments D1 to D4, further comprising contacting the nucleic acid sample with one or more restriction enzymes prior to (a).

D6. The method of embodiment D5, wherein the one or more restriction enzymes are methylation sensitive.

D7. The method of embodiment D6, wherein the restriction enzymes are HhaI and HpaII.

D8. The method of any one of embodiments D1 to D7, wherein the first, second, third and fourth regions each comprise one or more genomic loci.

D9. The method of embodiment D8, wherein the genomic loci are the same length.

D10. The method of embodiment D9, wherein the genomic loci are about 50 base pairs to about 200 base pairs.

D11. The method of embodiment D10, wherein the genomic loci are about 60 base pairs to about 80 base pairs.

D12. The method of embodiment D11, wherein the genomic loci are about 70 base pairs.

D13. The method of embodiment D1, wherein the first region comprises one or more loci that are differentially methylated between the fetal and maternal nucleic acid.

D14. The method of embodiment D1, wherein the first region comprises loci within the TBX3 and SOX14 genes.

D15. The method of embodiment D14, wherein the loci for the first region each comprise independently SEQ ID NO:29 and SEQ ID NO:30.

D16. The method of embodiment D1, wherein the second region comprises one or more loci which do not contain a restriction site for a methylation-sensitive restriction enzyme.

D17. The method of embodiment D1, wherein the second region comprises loci within the POP5 and APOE genes.

D18. The method of embodiment D17, wherein the loci for the second region each comprise independently SEQ ID NO:31 and SEQ ID NO:32.

D19. The method of embodiment D1, wherein the third region comprises one or more loci within chromosome Y.

D20. The method of embodiment D1, wherein the third region comprises a locus within the DDX3Y gene.

D21. The method of embodiment D20, wherein the locus for the third region comprises SEQ ID NO:34.

D22. The method of embodiment D1, wherein the fourth region comprises one or more loci present in every genome in the sample and unmethylated in fetal and maternal nucleic acid.

D23. The method of embodiment D1, wherein the fourth region comprises loci within the POP5 or LDHA genes.

D24. The method of embodiment D23, wherein the loci for the fourth region each comprise independently SEQ ID NO:35 and SEQ ID NO:36.

D25. The method of embodiment D1, wherein the first and second sets of amplification primers each comprise one or more pairs of forward and reverse primers.

D26. The method of embodiment D1, wherein the third and fourth sets of amplification primers each comprise one or more pairs of forward and reverse primers.

D27. The method of embodiment D25 or D26, wherein one or more amplification primer pairs further comprise a 5' tail.

D28. The method of embodiment D27, wherein the 5' tail is a distinct length for each amplification primer set.

D29. The method of any one of embodiments D25 to D28, wherein the amplification primers each comprise independently SEQ ID NOs:1 to 8 and SEQ ID NOs:11 to 16.

D30. The method of embodiment D1, wherein an inhibitory oligonucleotide of the one or more inhibitory oligonucleotides comprises a nucleotide sequence complementary to a nucleotide sequence in the second region.

D31. The method of embodiment D30, wherein the inhibitory oligonucleotide and a primer in the second set of amplification primers are complementary to the same nucleotide sequence in the second region.

D32. The method of embodiment D30 or D31, wherein the inhibitory oligonucleotide comprises one or more 3' mismatched nucleotides.

D33. The method of embodiment D32, wherein the inhibitory oligonucleotides each comprise independently SEQ ID NO:17, SEQ ID NO:18, SEQ ID NO:19, and SEQ ID NO:20.

D34. The method of any one of embodiments D1 to D33, wherein the amount of the fetal nucleic acid determined is the fraction of the fetal nucleic acid in the sample based on the amount of each of the separated fetal and total nucleic acid amplification products.

D34.1 The method of embodiment D34, wherein the fraction of fetal nucleic acid is relative to the total amount of nucleic acid in the sample.

D35. The method of any one of embodiments D1 to D34.1, wherein the competitor oligonucleotides comprise a stuffer sequence.

D36. The method of embodiment D35, wherein the stuffer sequence length is constant for one or more of the first competitor oligonucleotides, second competitor oligonucleotides, third competitor oligonucleotides and fourth competitor oligonucleotides.

D37. The method of embodiment D35, wherein the stuffer sequence length is variable for one or more of the first competitor oligonucleotides, second competitor oligonucleotides, third competitor oligonucleotides and fourth competitor oligonucleotides.

D38. The method of embodiments D36 or D37, wherein the stuffer sequence is from a non-human genome.

D39. The method of embodiment D38, wherein the stuffer sequence is from the PhiX 174 genome.

D40. The method of any one of embodiments D1 to D39, wherein the competitor oligonucleotide is about 100 to about 150 base pairs long.

D41. The method of embodiment D40, wherein the competitor oligonucleotide is about 115 to about 120 base pairs long.

D42. The method of embodiment D41, wherein the first and second competitor oligonucleotide is about 115 base pairs long.

D43. The method of embodiment D41, wherein the third competitor oligonucleotide is about 118 base pairs long.

D44. The method of embodiment D41, wherein the fourth competitor oligonucleotide is about 120 base pairs long.

D45. The method of embodiment D42, wherein the one or more first competitor oligonucleotides each comprise independently SEQ ID NO:21 and SEQ ID NO:22.

D46. The method of embodiment D42, wherein the one or more second competitor oligonucleotides each comprise independently SEQ ID NO:23 and SEQ ID NO:24.

D47. The method of embodiment D43, wherein the third competitor oligonucleotide comprises SEQ ID NO:26.

D48. The method of embodiment D44, wherein the one or more fourth competitor oligonucleotides each comprise independently SEQ ID NO:26 and SEQ ID NO:27.

D49. The method of any one of embodiments D1 to D48, wherein one or more competitor oligonucleotides comprise a detectable label.

D50. The method of embodiment D49, wherein the detectable label is a fluorophore.

D51. The method of embodiment D50, wherein the fluorophore is different for each competitor oligonucleotide.

D52. The method of any one of embodiments D1 to D51, wherein a predetermined copy number of each competitor oligonucleotide is used.

D53. The method of embodiment D52, wherein the amount of the fetal nucleic acid determined is the copy number of the fetal nucleic acid based on the amount of competitor oligonucleotide used.

D54. The method of embodiment D53, further comprising determining the copy number of the maternal nucleic acid.

D55. The method of any one of embodiments D1 to D54, wherein the sample nucleic acid is extracellular nucleic acid.

D56. The method of any one of embodiments D1 to D55, wherein the nucleic acid sample is obtained from a pregnant female subject.

D57. The method of embodiment D56, wherein the subject is human.

D58. The method of any one of embodiments D1 to D57, wherein the sample nucleic acid is from plasma.

D59. The method of any one of embodiments D1 to D57, wherein the sample nucleic acid is from serum.

D60. The method of any one of embodiments D1 to D59, wherein the amplification is in a single reaction vessel.

D61. The method of any one of embodiments D1 to D60, wherein the amplification is by polymerase chain reaction (PCR).

D62. The method of any one of embodiments D1 to D61, further comprising contacting the amplification products with an exonuclease prior to (b).

D63. The method of any one of embodiments D1 to D62, wherein the separation of amplification products is based on length.

D64. The method of any one of embodiments D1 to D63, wherein the separation is performed using electrophoresis.

D65. The method of embodiment D64, wherein the electrophoresis is capillary electrophoresis.

D66. The method of any of embodiments D1 to D65, further comprising determining whether the nucleic acid sample is utilized for a sequencing reaction.

D67. The method of embodiment D66, wherein the sequencing reaction is a reversible terminator-based sequencing reaction.

D68. The method of any of embodiments D1 to D67, further comprising determining whether sequencing information obtained for a nucleic acid sample is used for a diagnostic determination.

E1. A composition comprising a mixture of two or more amplified target nucleic acids distinguishable by length, wherein each amplicon comprises a first sequence identical to a target nucleic acid and one or more second sequences of variable length that are not identical to a target nucleic acid, wherein the target nucleic acids each comprise independently:
 (a) a first region comprising a feature that (i) is present in a minority nucleic acid and is not present in a majority nucleic acid species, or (ii) is not present in a minority nucleic acid species and is present in a majority nucleic acid species, and
 (b) a second region allowing for a determination of total nucleic acid in the sample, wherein the first and second regions are different.

E2. The composition of embodiment E1, wherein the first region and the second region are differentially methylated.

E3. The composition of embodiment E1 or E2, wherein the target nucleic acid further comprises a third region allowing for a determination of the presence or absence of Y chromosome nucleic acid.

E4. The composition of any one of embodiments E1 to E3, wherein the target nucleic acid further comprises a fourth region allowing for a determination of the amount of digested or undigested nucleic acid, as an indicator of digestion efficiency.

E5. The composition of any one of embodiments E1 to E4, wherein the target nucleic acid comprises one or more independent genomic DNA target sequences.

E6. The composition of embodiment E5, wherein the genomic DNA target sequences are the same length.

E7. The composition of embodiment E6, wherein the genomic DNA target sequences each comprise independently SEQ ID NOs:29 to 32 and SEQ ID NOs:34 to 36.

E8. The composition of any one of embodiments E1 to E7, wherein the target nucleic acid further comprises one or more independent competitor oligonucleotides.

E9. The composition of embodiment E8, wherein the one or more competitor oligonucleotides comprise a stuffer sequence.

E10. The composition of embodiment E9, wherein the competitor oligonucleotides each comprise independently SEQ ID NOs:21 to 24 and SEQ ID NOs:26 to 28.

F1. A kit for determining the amount of a minority nucleic acid species in a sample which contains a minority species and a majority species, the combination of the minority species and the majority species comprising total nucleic acid in the sample, comprising:
 (a) a first set of amplification primers that specifically amplify a first region in sample nucleic acid comprising a feature that (i) is present in the minority nucleic acid species and is not present in the majority nucleic acid species, or (ii) is not present in the minority nucleic acid species and is present in the majority nucleic acid species,
 (b) a second set of amplification primers that amplify a second region in the sample nucleic acid allowing for a determination of total nucleic acid in the sample, wherein the first region and the second region are different, and
 (c) one or more inhibitory oligonucleotides that reduce the amplification of the second region.

F2. The kit of embodiment F1, further comprising a third set of amplification primers that amplify a third region in the sample nucleic acid allowing for a determination of the presence or absence of Y chromosome nucleic acid.

F3. The kit of embodiments F1 or F2, further comprising a fourth set of amplification primers that amplify a fourth region in the sample nucleic acid allowing for a determination of the amount of digested or undigested nucleic acid, as an indicator of digestion efficiency.

F4. The kit of any one of embodiments F1 to F3, further comprising one or more first competitor oligonucleotides that compete with the first region for hybridization of primers of the first amplification primer set.

F5. The kit of any one of embodiments F1 to F4, further comprising one or more second competitor oligonucleotides that compete with the second region for hybridization of primers of the second amplification primer set.

F6. The kit of any one of embodiments F2 to F5, further comprising one or more third competitor oligonucleotides that compete with the third region for hybridization of primers of the third amplification primer set.

F7. The kit of any one of embodiments F3 to F6, further comprising one or more fourth competitor oligonucleotides that compete with the fourth region for hybridization of primers of the fourth amplification primer set.

F8. The kit of any one of embodiments F1 to F7, further comprising one or more methylation sensitive restriction enzymes.

F9. The kit of any of embodiments F1 to F8, further comprising instructions or a location for carrying out a method for determining the amount of a minority nucleic acid species in a sample comprising:

(a) contacting under amplification conditions a nucleic acid sample comprising a minority species and a majority species, the combination of the minority species and the majority species comprising total nucleic acid in the sample, with:
  (i) a first set of amplification primers that specifically amplify a first region in sample nucleic acid comprising a feature that (1) is present in the minority nucleic acid species and is not present in the majority nucleic acid species, or (2) is not present in the minority nucleic acid species and is present in the majority nucleic acid species,
  (ii) a second set of amplification primers that amplify a second region in the sample nucleic acid allowing for a determination of total nucleic acid in the sample, wherein the first region and the second region are different, and
  (iii) one or more inhibitory oligonucleotides that reduce the amplification of the second region, thereby generating minority nucleic acid amplification products and total nucleic acid amplification products, wherein the total nucleic acid amplification products are reduced relative to total amplification products that would be generated if no inhibitory oligonucleotide was present;

(b) separating the amplification products, thereby generating separated minority amplification products and total nucleic acid amplification products; and (c) determining the fraction of the minority nucleic acid species in the sample based on the amount of each of the separated minority amplification products and total nucleic acid amplification products.

F9.1 The kit of embodiment F9, wherein the fraction of the minority nucleic acid species in the sample is relative to the total amount of the nucleic acid in the sample.

F10. The kit of any one of embodiments F1 to F9.1, wherein the inhibitory oligonucleotide comprises one or more 3' mismatched nucleotides.

F11. The kit of embodiment F9 or F10, wherein the method further comprises contacting under amplification conditions the nucleic acid with third set of amplification primers that amplify a third region in the sample nucleic acid allowing for a determination of the presence or absence of Y chromosome nucleic acid.

F12. The kit of any one of embodiments F9 to F11, wherein the method further comprises contacting under amplification conditions the nucleic acid with a fourth set of amplification primers that amplify a fourth region in the sample nucleic acid allowing for a determination of the amount of digested or undigested nucleic acid, as an indicator of digestion efficiency.

F13. The kit of any one of embodiments F9 to F12, wherein the method further comprises contacting under amplification conditions the nucleic acid with one or more first competitor oligonucleotides that compete with the first region for hybridization of primers of the first amplification primer set.

F14. The kit of any one of embodiments F9 to F13, wherein the method further comprises contacting under amplification conditions the nucleic acid with one or more second competitor oligonucleotides that compete with the second region for hybridization of primers of the second amplification primer set.

F15. The kit of any one of embodiments F11 to F14, wherein the method further comprises contacting under amplification conditions the nucleic acid with one or more third competitor oligonucleotides that compete with the third region for hybridization of primers of the third amplification primer set.

F16. The kit of any one of embodiments F12 to F15, wherein the method further comprises contacting under amplification conditions the nucleic acid with one or more fourth competitor oligonucleotides that compete with the fourth region for hybridization of primers of the fourth amplification primer set.

F17. The kit of any one of embodiments F4 to F16, wherein a predetermined copy number of each competitor oligonucleotide is used.

F18. The kit of embodiment F17, wherein the amount of the minority nucleic acid determined is the copy number of the minority nucleic acid species based on the amount of competitor oligonucleotide used.

F19. The kit of any one embodiments F1 to F18, wherein the minority nucleic acid species is fetal DNA and the majority nucleic acid species is maternal DNA.

F20. The kit of any one of embodiments F1 to F19, wherein the first region is methylated and the second region is unmethylated.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for determining the amount of a minority nucleic acid species in a sample comprising:
   (a) contacting under amplification conditions a nucleic acid sample comprising a minority species and a majority species, the combination of the minority species and the majority species comprising total nucleic acid in the sample, with:
      (i) a first set of amplification primers that specifically amplify a first region in sample nucleic acid comprising a feature that (1) is present in the minority nucleic acid species and is not present in the majority nucleic acid species, or (2) is not present in the minority nucleic acid species and is present in the majority nucleic acid species,
      (ii) a second set of amplification primers that amplify a second region in the sample nucleic acid allowing for a determination of total nucleic acid in the sample, wherein the first region and the second region are different, and
      (iii) one or more inhibitory oligonucleotides, each comprising a nucleotide sequence complementary to a nucleotide sequence in the second region, wherein the one or more inhibitory oligonucleotides (1) hybridize to the second region but are not extended and (2) reduce the amplification of the second region; thereby generating minority nucleic acid amplification products and total nucleic acid amplification products, wherein the total nucleic acid amplification products are reduced relative to total amplification products that would be generated if no inhibitory oligonucleotide was present, whereby the total nucleic acid amplification products do not dominate the minority nucleic acid amplification products;
   (b) separating the minority nucleic acid amplification products and total nucleic acid amplification products, thereby generating separated minority nucleic acid amplification products and total nucleic acid amplification products; and
   (c) determining the fraction of the minority nucleic acid species in the sample based on the amount of each of the separated minority nucleic acid amplification products and total nucleic acid amplification products.

2. The method of claim 1, further comprising contacting the nucleic acid sample with one or more methylation sensitive restriction enzymes prior to (a).

3. The method of claim 1, wherein the first and second regions each comprise one or more genomic loci, wherein the first region comprises one or more loci that are differentially methylated between the minority species and majority species and the second region comprises one or more loci which do not contain a restriction site for a methylation-sensitive restriction enzyme.

4. The method of claim 1, wherein the first and second amplification primer sets comprise one or more primer pairs comprising a 5' tail having a distinct length for each amplification primer set.

5. The method of claim 1, further comprising contacting under amplification conditions the nucleic acid sample with one or more first competitor oligonucleotides that compete with the first region for hybridization of primers of the first amplification primer set.

6. The method of claim 5, further comprising contacting under amplification conditions the nucleic acid sample with one or more second competitor oligonucleotides that compete with the second region for hybridization of primers of the second amplification primer set.

7. The method of claim 6, wherein the competitor oligonucleotides comprise a stuffer sequence comprising a nucleotide sequence from a non-human genome.

8. The method of claim 5, further comprising determining the copy number of the minority nucleic acid based on a predetermined copy number of competitor oligonucleotide used.

9. The method of claim 1, wherein the amplification is in a single reaction vessel.

10. The method of claim 1, wherein the separation of amplification products is performed using electrophoresis.

11. The method of claim 1, wherein the sample nucleic acid is extracellular nucleic acid.

12. A method for determining the copy number of a minority nucleic acid species in a sample comprising:
   (a) contacting under amplification conditions a nucleic acid sample comprising a minority species and a majority species, the combination of the minority species and the majority species comprising total nucleic acid in the sample, with:
      (i) a first set of amplification primers that specifically amplify a first region in sample nucleic acid comprising a feature that (1) is present in the minority nucleic acid species and is not present in the majority nucleic acid species, or (2) is not present in the minority nucleic acid species and is present in the majority nucleic acid species,
      (ii) a second set of amplification primers that amplify a second region in the sample nucleic acid allowing for a determination of the total nucleic acid in the sample, wherein the first region and the second region are different,
      (iii) one or more first competitor oligonucleotides that compete with the first region for hybridization of primers of the first amplification primer set, and
      (iv) one or more second competitor oligonucleotides that compete with the second region for hybridization of primers of the second amplification primer set, thereby generating minority nucleic acid amplification products, total nucleic acid amplification products, first competitor amplification products and second competitor amplification products, wherein each of the minority nucleic acid, total nucleic acid, first competitor and second competitor amplification products are of different lengths;
   (b) separating the minority nucleic acid amplification products, total nucleic acid amplification products, and competitor amplification products, thereby generating separated minority nucleic acid amplification products, total nucleic acid amplification products, and competitor amplification products; and
   (c) determining the copy number of the minority nucleic acid species in the sample based on the separated amplification products.

13. The method of claim 12, further comprising contacting the nucleic acid sample with one or more methylation sensitive restriction enzymes prior to (a).

14. The method of claim 12, wherein the first and second regions each comprise one or more genomic loci, wherein the first region comprises one or more loci that are differentially methylated between the minority species and majority species and the second region comprises one or more loci which do not contain a restriction site for a methylation-sensitive restriction enzyme.

15. The method of claim 12, wherein the first and second amplification primer sets comprise one or more primer pairs comprising a 5' tail having a distinct length for each amplification primer set.

16. The method of claim 12, further comprising contacting under amplification conditions the nucleic acid sample with one or more inhibitory oligonucleotides that reduce the amplification of the second region.

17. The method of claim 12, further comprising determining the fraction of the minority nucleic acid in the sample based on the amount of each of the separated minority and total nucleic acid amplification products.

18. The method of claim 12, wherein the competitor oligonucleotides comprise a stuffer sequence comprising a nucleotide sequence from a non-human genome.

19. The method of claim 12, wherein the amplification is in a single reaction vessel.

20. The method of claim 12, wherein the separation of amplification products is performed using electrophoresis.

21. The method of claim 12, wherein the sample nucleic acid is extracellular nucleic acid.

22. The method of claim 1, wherein the inhibitory oligonucleotide comprises one or more 3' mismatched nucleotides.

23. The method of claim 16, wherein the inhibitory oligonucleotide comprises one or more 3' mismatched nucleotides.

* * * * *

```
                        SEQUENCE LISTING

<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctttgtctct gcgtgcccgg                                            20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgcatggccg gcgccagagt                                            20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccacggaatc ccggctctgt                                            20

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cttcctagtg tgagaaccgg caac                                       24

<210> SEQ ID NO 5
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 5
ttggaccacc agtttagact gaactgtgaa                                          30

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agttgggtag gagtgaggtg gtatggcta                                           29

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttggagacag tttctccttc cccagac                                             27

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agttggcagc aacgcagccc acag                                                24

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tttcgtgata ttgatgccgc ccttcccatc gc                                       32

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tttcgtgata ttgtctgtgc tgggtgtttt tgcag                                    35

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
```

```
                                primer

<400> SEQUENCE: 11
tttcgtgata ttccaagttt caaaaaatcc tgagtccaca at                    42

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttcgtgata tgacttactg ctcactgaat tttggagtc                        39

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cttcgataaa aatgattgca ctcgtgcccc ttctttctt                        39

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cttcgataaa aatgattgag gggaacccgg gaggat                           36

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cttcgataaa aatgattgga caggcctttg caacaaggat                       40

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cttcgataaa aatgattggc ctgttaacca accgggag                         38

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 17
ttggaccacc agtttagact gaactgtgaa tacac                          35

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttgggtagga gtgaggtggt atggctatct gc                             32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttggagacag tttctccttc cccagacact at                             32

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttggcagcaa cgcagcccac agcaatg                                   27

<210> SEQ ID NO 21
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
ctttgtctct gcgtgcccgg caattcggat gttcgtcaag gacgcgcccc cctcccggtg    60
ggtgataaac cgattaagtt catcaagtct gatccactct ggcgccggcc atgcg        115

<210> SEQ ID NO 22
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ccacggaatc ccggctctgt gcagtttrct ggtcgtgttc aacatgcgcc caggttccgg    60
ggcttgggca tgacttcgtg ataaaagatt cgttgccggt tctcacacta ggaag        115

<210> SEQ ID NO 23
<211> LENGTH: 115
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 23
ccaccagttt agactgaact gtgaacgctt ggcttccata agcagatggg tgtcaccaat    60
tgaaaatcac tcttaaggat attcgcgatg agtagccata ccacctcact cctac    115

<210> SEQ ID NO 24
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gacagtttct ccttccccag actgactgcc tatgatgttt atcctggcca atcacaggca    60
ggaagatgaa ggtctgataa aggaaaggat actcgttctg tgggctgcgt tgctg    115

<210> SEQ ID NO 25
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gatgccgccc ttcccatcgc tctcttcccc ttcatcagta ttttaccaat gaccaaatca    60
aagaaatgac tcgcaaggtt agagcgtatc gcaactgcaa aaacacccag cacagaca    118

<210> SEQ ID NO 26
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ccttctgcgg acctgttctt tcacctccct aacctgagca gcgttaccat gatgttattt    60
cttcatttgg aggtaaaacc tcttaagatt gtattcaaac caccgtggat cgctcacg    118

<210> SEQ ID NO 27
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
cactcgtgcc ccttctttct tcttatgttc atcccgtcaa cattcaactc cggcgcctgc    60 ccctccaca tcccgcatag cttgcaaaat acgtggcctt acatcctccc gggttccct    120

<210> SEQ ID NO 28
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gacaggcctt tgcaacaagg atctaaccct aatgagctta atcaagatac ggccgaagcc    60

```
acaccgtgcg cctcaggaaa cactgacgtt cttactgacc ctcccggttg gttaacaggc    120
```

<210> SEQ ID NO 29
<211> LENGTH: 70
<212> TYPE: DNA
<213> ORGANISM: Homo sapiens

<400> SEQUENCE: 29

```
ctttgtctct gcgtgcccgg cgcgccccc tcccggtggg tgataaaccc actctggcgc    60
cggccatgcg                                                          70
```

<210> SEQ ID NO 30
<211> LENGTH: 70
<212> TYPE: DNA
<213> ORGANISM: Homo sapiens

<400> SEQUENCE: 30

```
ccacggaatc ccggctctgt gtgcgcccag gttccggggc ttgggcgttg ccggttctca    60
cactaggaag                                                          70
```

<210> SEQ ID NO 31
<211> LENGTH: 70
<212> TYPE: DNA
<213> ORGANISM: Homo sapiens

<400> SEQUENCE: 31

```
ccaccagttt agactgaact gtgaacgtgt caccaattga aaatcagtag ccataccacc    60
tcactcctac                                                          70
```

<210> SEQ ID NO 32
<211> LENGTH: 70
<212> TYPE: DNA
<213> ORGANISM: Homo sapiens

<400> SEQUENCE: 32

```
gacagtttct ccttccccag actggccaat cacaggcagg aagatgaagg ttctgtgggc    60
tgcgttgctg                                                          70
```

<210> SEQ ID NO 33
<211> LENGTH: 70
<212> TYPE: DNA
<213> ORGANISM: Homo sapiens

<400> SEQUENCE: 33

```
gatgccgccc ttcccatcgc tctcttcccc ttcaagcgta tcgcaactgc aaaaacaccc    60
agcacagaca                                                          70
```

<210> SEQ ID NO 34
<211> LENGTH: 70
<212> TYPE: DNA
<213> ORGANISM: Homo sapiens

<400> SEQUENCE: 34

```
ccttctgcgg acctgttctt tcacctccct aacctgaaga ttgtattcaa accaccgtgg    60
atcgctcacg                                                          70
```

<210> SEQ ID NO 35
<211> LENGTH: 70
<212> TYPE: DNA
<213> ORGANISM: Homo sapiens

```
<400> SEQUENCE: 35
cactcgtgcc ccttctttct tcctccggcg cctgccccct ccacatcccg ccatcctccc    60
gggttcccct                                                           70

<210> SEQ ID NO 36
<211> LENGTH: 70
<212> TYPE: DNA
<213> ORGANISM: Homo sapiens

<400> SEQUENCE: 36
gacaggcctt tgcaacaagg atcacggccg aagccacacc gtgcgcctcc ctcccggttg    60
gttaacaggc                                                           70

<210> SEQ ID NO 37
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gtgcaactgg acaacaggtt gtacagggat gactgtttta tgataatccc aatgctttgc    60
gtgactattt tcgtgatatt gggtacgaaa gccacacact caagaatgga gcaccagc    118

<210> SEQ ID NO 38
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gtgcaactgg acaacaggtt gtacagggat gactcgaaag ccacacactc aagaatggag    60
caccagc                                                              67
```